(12) United States Patent
Smolke et al.

(10) Patent No.: US 10,752,903 B2
(45) Date of Patent: *Aug. 25, 2020

(54) BENZYLISOQUINOLINE ALKALOID (BIA) PRECURSOR PRODUCING MICROBES, AND METHODS OF MAKING AND USING THE SAME

(71) Applicant: The Board of Trustees of the Leland Stanford Junior University, Stanford, CA (US)

(72) Inventors: Christina D. Smolke, Menlo Park, CA (US); Catherine Thodey, Mountain View, CA (US); Isis Trenchard, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/567,354

(22) PCT Filed: May 4, 2016

(86) PCT No.: PCT/US2016/030808
§ 371 (c)(1),
(2) Date: Oct. 17, 2017

(87) PCT Pub. No.: WO2016/179296
PCT Pub. Date: Nov. 10, 2016

(65) Prior Publication Data
US 2018/0163212 A1 Jun. 14, 2018

Related U.S. Application Data

(60) Provisional application No. 62/156,701, filed on May 4, 2015.

(51) Int. Cl.
| | |
|---|---|
| *C12N 15/52* | (2006.01) |
| *C12P 17/12* | (2006.01) |
| *C12P 13/22* | (2006.01) |
| *C12N 15/81* | (2006.01) |
| *C12N 15/79* | (2006.01) |
| *C07D 217/22* | (2006.01) |
| *C07D 217/18* | (2006.01) |

(52) U.S. Cl.
CPC ............ *C12N 15/52* (2013.01); *C12N 15/79* (2013.01); *C12N 15/81* (2013.01); *C12P 13/22* (2013.01); *C12P 17/12* (2013.01); *C12Y 114/16002* (2013.01); *C12Y 401/01028* (2013.01); *C07D 217/18* (2013.01); *C07D 217/22* (2013.01)

(58) Field of Classification Search
CPC ........ C12N 15/52; C12N 15/79; C12N 15/81; C12P 13/22; C12P 17/122; C07D 217/18; C07D 217/22; C12Y 401/01028; C12Y 114/16002
See application file for complete search history.

(56) References Cited

U.S. PATENT DOCUMENTS

| | | |
|---|---|---|
| 7,037,674 B1 | 5/2006 | Kutchan et al. |
| 7,045,290 B2 | 5/2006 | Lindquist et al. |
| 7,193,127 B1 | 3/2007 | Kutchan et al. |
| 7,390,642 B2 | 6/2008 | Kutchan et al. |
| 7,514,251 B2 | 4/2009 | Kutchan et al. |
| 7,767,428 B2 | 8/2010 | Kutchan et al. |
| 8,318,474 B1 | 11/2012 | Smolke et al. |
| 8,710,226 B2 | 4/2014 | Patel et al. |
| 8,735,111 B2 | 5/2014 | Vanhercke |
| 8,975,063 B2 | 3/2015 | Smolke et al. |
| 8,993,280 B2 | 3/2015 | Sato et al. |
| 9,200,261 B2 | 12/2015 | Winzer et al. |
| 9,322,039 B2 | 4/2016 | Smolke et al. |
| 9,376,696 B1 | 6/2016 | Smolke et al. |
| 9,447,444 B2 | 9/2016 | Winzer et al. |
| 9,458,481 B2 | 10/2016 | Winzer et al. |

(Continued)

FOREIGN PATENT DOCUMENTS

| | | |
|---|---|---|
| EP | 1512748 A1 | 3/2005 |
| EP | 1837396 | 9/2007 |

(Continued)

OTHER PUBLICATIONS

Broun et al., Catalytic plasticity of fatty acid modification enzymes underlying chemical diversity of plant lipids. Science, 1998, vol. 282: 1315-1317. (Year: 1998).*

Devos et al., Practical limits of function prediction. Proteins: Structure, Function, and Genetics. 2000, vol. 41: 98-107. (Year: 2000).*

Nakagawa et al., Bioengineering of Isoquinoline alkaloid production in microbial systems. Adv. Botanical Res., 2013, vol. 68, Chapter 7: 183-203. (Year: 2013).*

Nakagawa et al., (R,S)-Tetrahydropapaveroline production by stepwise fermentation using engineered *Escherichia coli*. Nature Scientific Reports, 2014, vol. 4: 6695, pp. 1-8. (Year: 2014).*

(Continued)

*Primary Examiner* — Ganapathirama Raghu
(74) *Attorney, Agent, or Firm* — Bret E. Field; Bozicevic, Field & Francis LLP

(57) ABSTRACT

Methods and engineered yeast cells for generating a benzylisoquinoline alkaloid product are provided herein. A method comprises providing engineered yeast cells and a feedstock to a reactor. In the reactor, the engineered yeast cells are subjected to fermentation by incubating the engineered yeast cells for a time period to produce a solution comprising the BIA product and cellular material. The solution comprises not more than one class of molecule selected from the group of protoberberine, morphinan, isopavine, aporphine, and benzylisoquinoline. Additionally, at least one separation unit is used to separate the BIA product from the cellular material to provide the product stream comprising the BIA product.

12 Claims, 18 Drawing Sheets

(56) References Cited

U.S. PATENT DOCUMENTS

| | | |
|---|---|---|
| 9,534,241 B2 | 1/2017 | Smolke et al. |
| 9,725,732 B2 | 8/2017 | Winzer et al. |
| 9,862,979 B2 | 1/2018 | Winzer et al. |
| 9,926,329 B2 | 3/2018 | Huntley et al. |
| 10,006,010 B2 | 6/2018 | Winzer et al. |
| 10,017,799 B2 | 7/2018 | Smolke et al. |
| 2004/0038352 A1 | 2/2004 | Maier |
| 2005/0106588 A1 | 5/2005 | Kutchan et al. |
| 2005/0139490 A1 | 6/2005 | Chou et al. |
| 2005/0277179 A1 | 12/2005 | Takai et al. |
| 2006/0185032 A1 | 8/2006 | Kutchan et al. |
| 2007/0199090 A1 | 8/2007 | Apuya et al. |
| 2008/0102499 A1 | 5/2008 | Templeton et al. |
| 2008/0176754 A1 | 7/2008 | Smolke et al. |
| 2008/0196123 A1 | 8/2008 | Kutchan et al. |
| 2010/0075385 A1 | 3/2010 | Kutchan et al. |
| 2010/0184166 A1 | 7/2010 | Sato et al. |
| 2013/0130340 A1 | 5/2013 | Yan et al. |
| 2013/0340119 A1 | 12/2013 | Plesch et al. |
| 2014/0013465 A1 | 1/2014 | Coombs et al. |
| 2014/0273109 A1 | 9/2014 | Smolke et al. |
| 2015/0267233 A1 | 9/2015 | Smolke et al. |
| 2016/0201101 A1 | 7/2016 | Facchini et al. |
| 2016/0304923 A1 | 10/2016 | Smolke et al. |
| 2016/0312256 A1 | 10/2016 | Facchini et al. |
| 2016/0319314 A1 | 11/2016 | Smolke et al. |
| 2016/0340704 A1 | 11/2016 | Martin et al. |
| 2017/0058305 A1 | 3/2017 | Facchini |
| 2017/0130250 A1 | 5/2017 | Facchini |
| 2017/0198299 A1 | 7/2017 | Winzer et al. |
| 2017/0267686 A1 | 9/2017 | Facchini |
| 2017/0280647 A1 | 10/2017 | Fist et al. |
| 2017/0306301 A1 | 10/2017 | Martin et al. |
| 2017/0362617 A1 | 12/2017 | Peralta-Yahya et al. |
| 2018/0163212 A1 | 6/2018 | Smolke et al. |
| 2018/0251801 A1 | 9/2018 | Aharoni et al. |

FOREIGN PATENT DOCUMENTS

| | | | |
|---|---|---|---|
| JP | H05504252 A | 7/1993 | |
| JP | 2009/225669 | 10/2009 | |
| JP | WO 2012/039438 * | 3/2012 | ............ C12P 17/12 |
| JP | 2014525255 | 9/2014 | |
| WO | WO2000058333 A1 | 10/2000 | |
| WO | WO2002101052 A2 | 12/2002 | |
| WO | WO2005021763 A2 | 3/2005 | |
| WO | WO2006015887 A2 | 2/2006 | |
| WO | WO 2008/067070 A2 | 6/2008 | |
| WO | WO 2008/067070 A3 | 10/2008 | |
| WO | WO 2008/153094 A1 | 12/2008 | |
| WO | WO2009122436 A2 | 10/2009 | |
| WO | WO 2011/058446 | 5/2011 | |
| WO | WO2011161431 A2 | 12/2011 | |
| WO | WO 2012/039438 A1 | 3/2012 | |
| WO | WO 2012/135389 A2 | 10/2012 | |
| WO | WO 2013/136057 A2 | 9/2013 | |
| WO | WO 2014/143744 A2 | 9/2014 | |
| WO | N02018027324 A1 | 2/2015 | |
| WO | WO 2015/021561 A1 | 2/2015 | |
| WO | WO 2015/066642 A1 | 5/2015 | |
| WO | WO 2015/081437 A1 | 6/2015 | |
| WO | WO 2015/103711 A1 | 7/2015 | |
| WO | WO 2014/143744 A3 | 11/2015 | |
| WO | WO2015164960 A1 | 11/2015 | |
| WO | WO2015173590 | 11/2015 | |
| WO | WO2016049364 A2 | 3/2016 | |
| WO | WO 2016/081371 A1 | 5/2016 | |
| WO | WO2016149821 A1 | 9/2016 | |
| WO | WO2016179296 A1 | 11/2016 | |
| WO | WO2016207643 A1 | 12/2016 | |
| WO | WO2017083632 A1 | 5/2017 | |
| WO | N02017122011 A1 | 7/2017 | |
| WO | N02018000089 A1 | 1/2018 | |
| WO | N02018005553 A1 | 1/2018 | |
| WO | N02018029282 A1 | 2/2018 | |
| WO | N02018039749 A1 | 3/2018 | |
| WO | N02018136654 A1 | 7/2018 | |

OTHER PUBLICATIONS

Seffernick et al., Melamine deaminase and Atrazine chlorohydrolase: 98 percent identical but functionally different. J. Bacteriol., 2001, vol. 183 (8): 2405-2410. (Year: 2001).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Cautha SC., Model design of a *Saccharomyces cerevisiae* platform strain with improved tyrosine production capabilities. M.A.Sc., Thesis, 2012, Univ., of Toronto, Canada. (Year: 2012).*

Siddiqui et al., Advancing secondary metabolite biosynthesis in yeast with synthetic biology tools. FEMS Yeat Res., 2012, vol. 12: 144-170. (Year: 2012).*

Alcantara et al. "Sanguinarine Biosynthesis Is Associated with the Endoplasmic Reticulum in Cultured Opium Poppy Cells after Elicitor Treatment," Plant Physiology, Apr. 22, 2005, vol. 138, pp. 173-183.

Allen et al., "RNAi-Mediated Replacement of Morphine with the Nonnarcotic Alkaloid Reticuline in Opium Poppy", Nat. Biotechnol. (2004), 22:1559-1566.

Avalos et al., "Compartmentalization of Metabolic Pathways in Yeast Mitochondria Improves the Production of Branched-Chain Alcohols", Nat. Biotechnol. (2013), 31:335-341.

Backes et al., "Organization of Multiple Cytochrome P450s with NADPH-Cytochrome P450 Reductase in Membranes", Pharmacol. Ther. (2003), 98:221-233.

Bayer et al., "Synthesis of Methyl Halides from Biomass Using Engineered Microbes", J. Am. Chem. Soc. (2009), 131:6508-6515.

Beaudoin et al., "Isolation and Characterization of a cDNA Encoding (S)-cis-N-Methylstylopine 14-Hydroxylase from Opium Poppy, a Key Enzyme in Sanguinarine Biosynthesis", Biochem. Biophys. Res. Commun. (2013), 431:597-603.

Bitter, Grant A., "Heterologous Gene Expression in Yeast," Methods in Enzymology, vol. 152, pp. 673-684 (1987).

Branden et al. Introduction to Protein Structure, Garland Publishing Inc., New York, p. 247 (1991).

Bruce et al., "Microbial Degradation of the Morphine Alkaloids. Purification and Characterization of Morphine Dehydrogenase from Pseudomonas putida M10", Biochem. J. (1991), 274(3):875-880.

Cautha, Sarat C. "Model based design of a *Saccharomyces cerevisiae* platform strain with improved tyrosine production capabilities," Masters Thesis, Toronto, Canada, 72 pages (2012). Retrieved from the internet on Jan. 28, 2015 at: http://hdl.handle.net/1807/33358.

Chávez-Béjar et al. "Metabolic Engineering of *Escherichia coli* for L-Tyrosine Production by Expression of Genes Coding for the Chorismate Mutase Domain of the Native Chorismate Mutase-Prephenate Dehydratase and a Cyclohexadienyl Dehydrogenase from Zymomonas mobilis," Applied and Environmental Microbiology, American Society for Microbiology, US, vol. 74, No. 10, pp. 3284-3290 (Mar. 14, 2008).

Choi et al., "Molecular Cloning and Characterization of Coclaurine N-Methyltransferase from Cultured Cells of Coptis japonica", J. Biol. Chem. (2002), 277:830-835.

Cooper et al., "On the amine oxidases of Klebsiella aerogenes strain W70," FEMS Microbiol. Lett., 146(1):85-89 (1997).

Curran et al. "Metabolic engineering of muconic acid production in *Saccharomyces cerevisiae*," Metabolic Engineering, Academic Press, US, vol. 15, Nov. 17, 2012, pp. 55-66.

Diaz Chavez et al., "Characterization of two Methylenedioxy Bridge-Forming Cytochrome P450-Dependent Enzymes of Alkaloid Formation in the Mexican Prickly Poppy Argemone mexicana", Arch. Biochem. Biophys. (2011), 507:186-193.

Dumas et al., "11 Beta-Hydroxylase Activity in Recombinant Yeast Mitochondria. In vivo Conversion of 11-Deoxycortisol to Hydrocortisone", Eur. J. Biochem. (1996), 238:495-504.

(56) References Cited

OTHER PUBLICATIONS

Facchini et al., "Differential and Tissue-Specific Expression of a Gene Family for Tyrosine/Dopa Decarboxylase in Opium Poppy," J. Biol. Chem., 269(43):26684-26690 (1994).
Farhi et al., "Harnessing Yeast Subcellular Compartments for the Production of Plant Terpenoids", Metab. Eng. (2011), 13:474-481.
Farrow et al., "Dioxygenases Catalyze O-Demethylation and O,Odemethylenation with Widespread Roles in Benzylisoquinoline Alkaloid Metabolism in Opium Poppy", J. Biol. Chem. (2013), 288:28997-29012.
Fisinger et al., "Thebaine Synthase: a New Enzyme in the Morphine Pathway in Papaver somniferum", Natural Product Communications (2007), 2(3):249-253.
French et al., "Biological Production of Semisynthetic Opiates Using Genetically Engineered Bacteria", Biotechnology (N Y) (1995), 13:674-676.
French et al., "Purification and Characterization of Morphinone Reductase from Pseudomonas putida M10", Biochem. J. (1994), 301(1):97-103.
Fukuda et al. "Breeding of Brewing Yeast Producing a Large Amount of Beta-Phenylethyl Alcohol and Beta-Phenylethyl Acetate," Agricultural and Biological Chemistry, Tokyo, Japan, vol. 54, No. 1, pp. 269-271 (1990).
Fukuda et al. "Feedback-Insensitive Mutation of 3-Deoxy-D-Arabino-Hepturosonate-7-Phosphate Synthase Caused by a Single Nucleotide Substitution of ARO4 Structural Gene in *Saccharomyces cerevisiae*," Journal of Fermentation and Bioengineering, vol. 74, No. 2, pp. 117-119 (1992).
Fukuda et al. "Molecular Breeding of a Sake Yeast with a Mutated AR04 Gene Which Causes Both Resistance to o-Fluoro-DL-Phenylalanine and Increased Production of Beta-Phenethyl Alcohol," Journal of Fermentation and Bioengineering, vol. 73, No. 5, pp. 366-369 (1992).
Geissler et al., "Molecular Modeling and Site-Directed Mutagenesis Reveal the Benzylisoquinoline Binding Site of the Short-Chain Dehydrogenase/Reductase Salutaridine Reductase", Plant Physiol. (2007), 143(4):1493-503.
Gesell et al. "CVP719B1 Is Salutaridine Synthase. The C-C Phenol-coupling Enzyme of Morphine Biosynthesis in Opium Poppy", Journal of Biological Chemistry, vol. 284, No. 36, Sep. 4, 2009, pp. 24432-24442.
Gesell et al., "Heterologous Expression of Two FAD-Dependent Oxidases with (S) Tetrahydroprotoberberine Oxidase Activity from Argemone mexicana and Berberis wilsoniae in Insect Cells", Planta. (2011), 233:1185-1197.
Grothe et al., "Molecular Characterization of the Salutaridinol 7-O-Acetyltransferase Involved in Morphine Biosynthesis in Opium Poppy Papaver somniferum", J. Biol. Chem. (2001), 276:30717-30723.
Gustafsson et al. "Codon bias and heterologous protein expression," Trends in Biotechnology, vol. 22, No. 7, pp. 346-353 (Jul. 2004).
Hagel et al., "Benzylisoquinoline Alkaloid Metabolism: a Century of Discovery and a Brave New World", Plant Cell Physiol. (2013), 54:647-672.
Hagel et al., "Characterization of a Flavoprotein Oxidase from Opium Poppy Catalyzing the Final Steps in Sanguinarine and Papaverine Biosynthesis", J. Biol. Chem. (2012), 287:42972-42983.
Hagel et al., "Dioxygenases Catalyze the O-Demethylation Steps of Morphine Biosynthesis in Opium Poppy", Nat. Chem. Biol. (2010), 6:273-275.
Hartmann et al. "Evolution of feedback-inhibited beta/alpha barrel isoenzymes by gene duplication and a single mutation," PNAS, vol. 100, No. 3, pp. 862-867 (Feb. 4, 2003).
Hawkins et al. "Production of benzylisoquinoline alkaloids in *Saccharomyces cerevisiae*," Nature Chemical Biology, vol. 4, No. 9, pp. 564-573 (Aug. 10, 2008).
Hawkins et al. "Supplementary Text and Figures. Production of benzylisoquinoline alkaloids in *Saccharomyces cerevisiae*," Nature Chemical Biology, Aug. 10, 2008, 15 pages.
Hawkins, K. "Metabolic Engineering of *Saccharomyces cerevisiae* for the Production of Benzylisoquinoline Alkaloids," Ph.D. Thesis, California Institute of Technology, Pasadena, California, 2009, pp. 1-154.
Higashi et al., "Atomic Structure of Salutaridine Reductase from the Opium Poppy (*Papaver somniferum*)", J. Biol. Chem. (2011), 286:6532-6541.
Hinnen et al. "Chapter 10: Heterologous Gene Expression in Yeast," Yeast Genetic Engineering, Barr et al. eds., Butterworths, pp. 193-213 (1989).
Hiroi et al., "Dopamine Formation from Tyramine by CYP2D6," Biochemical & Biophysical Research Communications, 249:838-843 (1998).
Ikezawa et al., "Molecular Cloning and Characterization of CYP719, a Methylenedioxy Bridge-Forming Enzyme that Belongs to a Novel P450 Family, from Cultured Coptis japonica Cells", J. Biol. Chem. (2003), 278:38557-38565.
Ikezawa et al., "Molecular Cloning and Characterization of Methylenedioxy Bridge-Forming Enzymes Involved in Stylopine Biosynthesis in Eschscholzia californica", FEBS J. (2007), 274:1019-1035.
Iraqui et al., "Characterisation of *Saccharomyces cerevisiae* AR08 and AR09 genes encoding aromatic aminotransferases I and II reveals a new aminotransferase subfamily," Mol. Gen. Genet., 257(2):238-248 (1998).
Jensen et al., "Plant NADPH-Cytochrome P450 Oxidoreductases", Phytochemistry (2010). 71:132-141.
Kim et al., "Improvement of Reticuline Productivity from Dopamine by Using Engineered *Escherichia coli*", Biosci. Biotechnol. Biochem. (2013), 77(10):2166-2168.
Kocharin, Kanokarn, "Metabolic Engineering of *Saccharomyces cerevisiae* for Polyhydroxybutyrate Production" PhD Thesis, Apr. 2013, 168 pages.
Koopman et al. "De novo production of the flavonoid naringenin in engineered *Saccharomyces cerevisiae*," Microbial Cell Factories, Biomed Central, GB, vol. 11, No. 1, Dec. 8, 2012, p. 155 (15 pages).
Kushnirov, "Rapid and Reliable Protein Extraction from Yeast", Yeast (2000), 16:857-860.
Kutchan et al., "Molecular Genetics of Plant Alkaloid Biosynthesis," Alkaloids, 50:257-316 (1998).
Kutchan, Tony M. "Heterologous expression of alkaloid biosynthetic genes—a review", Gene, vol. 179, No. 1, Nov. 7, 1996, pp. 73-81.
Larkin et al., "Increasing Morphinan Alkaloid Production by Over-Expressing Codeinone Reductase in Transgenic Papaver somniferum", Plant Biotechnol. J. (2007), 5:26-37.
Lee et al. "Bacillus licheniformis APase I gene promoter: a strong well-regulated promoter in B. Subtilis," Journal of General Microbiology, vol. 137, pp. 1127-1133 (1991).
Lee et al. "Metabolic engineering of microorganisms: general strategies and drug production," Drug Discovery Today, vol. 14, No. 1/2, pp. 78-88 (Sep. 18, 2008).
Lenz et al., "Acetyl Coenzyme A:Salutaridinol-7-O Acetyltransferase from Papaver somniferum Plant Cell Cultures", J. Biol. Chem. (1995), 270:31091-31096.
Lenz et al., "Purification and Properties of Codeinone Reductase (NADPH) from Papaver somniferum Cell Cultures and Differentiated Plants", Eur. J. Biochem. (1995), 233:132-139.
Liscombe et al., "Targeted Metabolite and Transcript Profiling for Elucidating Enzyme Function: Isolation of Novel N Methyltransferases from Three Benzylisoquinoline Alkaloid-Producing Species", Plant J. (2009), 60:729-743.
Lütke-Eversloh et al. "L-Tyrosine production by deregulated strains of *Escherichia coli*," Applied Microbiology and Biotechnology, Springer, Berlin, DE, vol. 75, No. 1, Jan. 13, 2007, pp. 103-110.
Lütke-Eversloh et al. "Perspectives of biotechnological production of L-tyrosine and its applications," Applied Microbiology and Biotechnology, Springer, Berlin, DE, vol. 77, No. 4, Oct. 30, 2007, pp. 751-762.
Luttik et al. "Alleviation of feedback inhibition in *Saccharomyces cerevisiae* aromatic amino acid biosynthesis: Quantification of metabolic impact," Metabolic Engineering, vol. 10, pp. 141-153 (2008).

(56) References Cited

OTHER PUBLICATIONS

LV et al. "LC-MS-MS Simultaneous Determination of L-Dopa and Its Prodrug L-Dopa n-Pentyl Hydrochloride in Rat Plasma," Chromatographia, vol. 72, No. 3/4, pp. 239-243, (2010).
Minami et al., "Microbial Production of Plant Benzylisoquinoline Alkaloids", Proc. Natl. Acad. Sci. U S A (2008), 105:7393-7398.
Minami, H. "Fermentation Production of Plant Benzylisoquinoline Alkaloids in Microbes," Bioscience, Biotechnology, and Biochemistry, vol. 77, No. 8, pp. 1617-1622 (Aug. 7, 2013).
Mishra et al. "Wound Induced Tanscriptional Regulation of Benzylisoquinoline Pathway and Characterization of Wound Inducible PsWRKY Transcription Factor from Papaver somniferum," PLoS One, Jan. 30, 2013, vol. 8, No. 1, pp. 1-15.
Mizutani et al., "Diversification of P450 Genes During Land Plant Evolution", Annu. Rev. Plant Biol. (2010), 61:291-315.
Moerner et al., "Illuminating single molecules in condensed matter," Science, 283(5408):1670-1676 (1999).
Morishige et al., "Molecular Characterization of the Sadenosyl-L-Methionine:3'-Hydroxy-N-Methylcoclaurine 4'-O-Methyltransferase Involved in Isoquinoline Alkaloid Biosynthesis in Coptis japonica", J. Biol. Chem. (2000), 275:23398-23405.
Muñoz et al. "Metabolic engineering of Escherichia coli for improving L-3,4-dihydroxyphenylalanine (L-DOPA) synthesis from glucose," Journal of Industrial Microbiology and Biotechnology; vol. 38, No. 11, pp. 1845-1852 (Apr. 22, 2011).
Nakagawa et al. "A bacterial platform for fermentative production of plant alkaloids," Nature Communications, vol. 2, Article No. 326, 8 pages (May 24, 2011).
Nakagawa et al., "Bench-Top Fermentative Production of Plant Benzylisoquinoline Alkaloids Using a Bacterial Platform", Bioeng. Bugs (2012), 3:49-53.
Ng et al. "Production of 2,3-butanediol in Saccharomyces cerevisiae by in silica aided metabolic engineering," Microbial Cell Factories, Biomed Central, GB, vol. 11, No. 1, May 28, 2012, p. 68 (14 pages).
Olson et al. "Production of tyrosine from sucrose or glucose achieved by rapid genetic changes to phenylalanine-producing Escherichia coli strains," Applied Microbiology and Biotechnology, vol. 74, No. 5, pp. 1031-1040 (Jan. 11, 2007).
Onoyovwe et al., "Morphine Biosynthesis in Opium Poppy Involves Two Cell Types: Sieve Elements and Laticifers", Plant Cell (2013), 25(10): 4110-4122.
Ounaroon et al., "(R,S)-Reticuline 7-O-Methyltransferase and (R,S)-Norcoclaurine 6-O-Methyltransferase of Papaver somniferum—cDNA Cloning and Characterization of Methyl Transfer Enzymes of Alkaloid Biosynthesis in Opium Poppy", Plant J. (2003), 36:808-819.
Rueffer et al. "(S)-Norlaudanosoline Synthase—The 1st Enzyme in the Benzylisoquinoline Biosynthetic-Pathway," FEBS Letters, vol. 129, No. 1, pp. 5-9 (Jun. 1981).
Ruohonen et al. "Modifications to the ADH1 promoter of Saccharomyces cerevisiae for efficient production of heterologous proteins," Journal of Biotechnology, vol. 39, pp. 193-203 (1995).
Samanani et al., "Molecular cloning and characterization of norcoclaurine synthase, an enzyme catalyzing the first committed step in benzylisoquinoline alkaloid biosynthesis," Plant J., 40(2):302-313 (2004).
Sandig et al., "Regulation of Endoplasmic Reticulum Biogenesis in Response to Cytochrome P450 Overproduction", Drug Metab. Rev. (1999), 31:393-410.
Sato et al., "Purification and Characterization of S-adenosyl-L-methionine: norcoclaurine 6-O-methyltransferase from Cultured Coptis japonica Cells", Eur. J. Biochem. (1994), 225:125-131.
Schmidheini et al. "A Single Point Mutation Results in a Constitutively Activated and Feedback-Resistant Chorismate Mutase of Saccharornyces cerevisiae," Journal of Bacteriology, vol. 171, No. 3, pp. 1245-1253 (Mar. 1989).
Schmidt et al. "Poppy alkaloid profiling by electrospray tandem mass spectrometry and electrospray FT-ICR mass spectrometry after [ring-13C6]-tyramine feeding," Phytochemistry, vol. 68, No. 2, pp. 189-202 (2007).
Siddiqui et al., "Advancing Secondary Metabolite Biosynthesis in Yeast with Synthetic Biology Tools", FEMS Yeast Res. (2012), 12:144-170.
Single Molecule Detection and Manipulation Workshop, Apr. 17-18, 2000, 28 pages. Retrieved from http://www.nigms.nih.gov/news/reports/single_molecules.html.
Stewart et al., "A Chemist's Perspective on the Use of Genetically Engineered Microbes as Reagents for Organic Synthesis," Biotechnology and Genetic Engineering Reviews, 14:67-143 (1997).
Takemura et al., "Molecular Cloning and Characterization of a Cytochrome P450 in Sanguinarine Biosynthesis from Eschscholzia californica Cells", Phytochemistry (2013), 91:100-108.
Trenchard et al. "De novo production of the key branch point benzylisoquinoline alkaloid reticuline in yeast," Metab. Eng., Jul. 10, 2015, vol. 31, pp. 74-83.
Unterlinner et al., "Molecular Cloning and Functional Expression of Codeinone Reductase: the Penultimate Enzyme in Morphine Biosynthesis in the Opium Poppy Papaver somniferum", Plant J. (1999), 18:465-475.
Vuralhan et al., "Identification and characterization of phenylpyruvate decarboxylase genes in Saccharomyces cerevisiae," Appl. Environ. Microbial., 69(8):4534-4541 (2003).
Vuralhan, Z. "Engineering of aromatic amino acid metabolism in Saccharomyces cerevisiae," Ph. D. Thesis. Apr. 11, 2006, pp. 1-110.
Wijekoon et al., "Systematic Knockdown of Morphine Pathway Enzymes in Opium Poppy Using Virus-Induced Gene Silencing", Plant J. (2012), 69:1052-1063.
Zenk et al., "Benzylisoquinoline Biosynthesis by Cultivated Plant Cells and Isolated Enzymes," Journal of Natural Products, 48(5):725-738 (1985).
Zhang et al., "14-Hydroxylation of Opiates: Catalytic Direct Autoxidation of Codeinone to 14-Hydroxycodeinone", J. Am. Chem. Soc. (2005), 127:7286-7287.
Ziegler et al., "Removal of Substrate Inhibition and Increase in Maximal Velocity in the Short Chain Dehydrogenase/Reductase Salutaridine Reductase Involved in Morphine Biosynthesis", J. Biol. Chem. (2009), 284:26758-26767.
Zimmer et al., "Protein Quality—a Determinant of the Intracellular Fate of Membrane-Bound Cytochromes P450 in Yeast", DNA Cell Biol. (1997), 16:501-514.
European Patent Office, Search Results under Rule 164(2)(b) EPC dated May 18, 2017 in corresponding European Patent Application No. 14802992.9, 14 pages.
PCT/US2014/063738 International Preliminary Report on Patentability dated May 10, 2016, 18 pages.
PCT/US2014/063738 International Search Report dated Apr. 9, 2015, 8 pages.
PCT/US2014/063738 Written Opinion dated Apr. 9, 2015, 10 pages.
French et al., Bacterial morphinone reductase is related to Old Yellow Enzyme, Biochem J. Dec. 15, 1995;312 ( Pt 3):671-8.
Lister et al., Transformations of codeine to important semisynthetic opiate derivatives by Pseudomonas putida m10, FEMS Microbiol Lett. Dec. 1, 1999;181(1):137-44.
Runguphan et al., Redesign of a dioxygenase in morphine biosynthesis, Chem Biol. Jun. 22, 2012;19(6):674-8.
Sharafi et al., Metabolic engineering of morphinan alkaloids by over-expression of codeinone reductase in transgenic hairy roots of Papaver bracteatum, the Iranian poppy, Biotechnol Lett. Mar. 2013;35(3):445-53.
Walker et al., Mechanistic studies of morphine dehydrogenase and stabilization against covalent inactivation, Biochem J. Feb. 1, 2000;345 Pt 3:687-92.
Willey et al., Nucleotide sequence and over-expression of morphine dehydrogenase, a plasmid-encoded gene from Pseudomonas putida M10, Biochem J. Mar. 1, 1993; 290(Pt 2): 539-544.
Beaudoin "Characterization of Oxidative Enzymes Involved in the Biosynthesis of Benzylisoquinoline Alkaloids in Opium Poppy", Mar. 2015, University of Calgary, 409 pages.
Communication pursuant to Article 94(3) EPC issued for European patent application No. 14802992.9, dated Feb. 19, 2019, 8 pages.
U.S. Appl. No. 16/216,829, filed Dec. 11, 2018, Smolke et al.
U.S. Appl. No. 15/078,874, downloaded from USPTO.
U.S. Appl. No. 15/139,263, downloaded from USPTO.

(56) References Cited

OTHER PUBLICATIONS

U.S. Appl. No. 16/165,940 Office Action dated Dec. 17, 2018, 37 pages.
International search report and written opinion dated Aug. 4, 2016 for PCT Application No. PCT/US2016/030808, 13 pages.
U.S. Appl. No. 16/224,217, filed Dec. 18, 2018, Siddiqui, et al.
U.S. Appl. No. 16/165,940, filed Oct. 19, 2018, Smolke, et al.
European search report and search opinion dated Apr. 10, 2017 for EP Application No. 14729501.8, 12 pages.
International search report and written opinion dated Sep. 15, 2015 for PCT Application No. PCT/US2014/027833 (with publication), 131 pages.
International Search Report for PCT/US07/81974, dated Jul. 8, 2008, 3 pages.
Notice of allowance dated Oct. 14, 2016 for U.S. Appl. No. 14/211,611, 19 pages.
Notice of allowance dated Nov. 18, 2016 for U.S. Appl. No. 14/211,611, 7 pages.
Notice of allowance dated dated Nov. 7, 2014 for U.S. Appl. No. 11/875,814, 9 pages.
Office action dated Jul. 25, 2016 for U.S. Appl. No. 14/211,611, 28 pages.
Office action dated Dec. 10, 2015 for U.S. Appl. No. 14/211,611, 27 pages.
Office action dated dated Feb. 18, 2009 for U.S. Appl. No. 11/875,814, 17 pages.
Office action dated dated May 23, 2014 for U.S. Appl. No. 11/875,814, 13 pages.
Office action dated dated Dec. 3, 2013 for U.S. Appl. No. 11/875,814, 14 pages.
Office action dated dated Dec. 29, 2009 for U.S. Appl. No. 11/875,814, 12 pages.
U.S. Appl. No. 15/078,874 Office Action dated Feb. 16, 2018, 9 pages.
U.S. Appl. No. 15/139,263 Office Action dated Feb. 16, 2018, 18 pages.
U.S. Appl. No. 15/360,763 Notice of Allowance dated May 11, 2018, 10 pages.
U.S. Appl. No. 15/360,763 Office Action dated Apr. 10, 2018, 6 pages.
U.S. Appl. No. 15/360,763 Office Action dated Dec. 20, 2017, 5 pages.
U.S. Appl. No. 15/567,354 Office Action dated Jul. 19, 2018, 31 pages.
Kisselev, "Polypeptide Release Factors in Prokaryotes and Eukaryotes-:Same Function, Different Structure", Structure, vol. 10, Jan. 2002, 2 pages.
U.S. Appl. No. 16/191,247 Office Action dated Jan. 15, 2019, 34 pages.
U.S. Appl. No. 15/517,761 Office Action dated Feb. 26, 2019, 19 pages.
Winzer, et al. "A Papaver somniferum 10-gene cluster for synthesis of the anticancer alkaloid noscapine", Science. Jun. 29, 2012;336(6089):1704-8.
Examination report No. 1 for Australian patent application 2015350229, dated Jul. 19, 2018, .10 pages.
Communication, Extended European Search Report for European patent application No. 15861129.3, 10 pages.
Office Action dated May 15, 2019 for U.S. Appl. No. 16/165,940, 50 pages.
Axelsson et al., Cell separation, centrifugation. Enc. Indust. Biotechnol: Bioprocess, Bioseparation and Cell Technol.,. 2010, pp. 1-20; Ed., Flickinger M.C., John Wiley & Sons, Inc.

Smirnova et al., Optical isomerism and biological activity of pharmaceutical preparations. Moscow Univ. Chem. Bull., 2012, vol. 67(3): 95-102.
Soares EV., Flocculation in *Saccharomyces cerevisiae*: a review. J. Appl. Microbial., 2010, vol. 110: 1-18.
Office Action dated May 15, 2019 for U.S. Appl. No. 15/031,618, 20 pages.
Dang, et al. "CYP82Y1 Is N-Methylcanadine 1-Hydroxylase, a Key Noscapine Biosynthetic Enzyme in Opium Poppy", The Journal of Biological Chemistry vol. 289, No. 4, pp. 2013-2026, 2014.
Communication, The Extended European Search Report for European patent application No. 16793332.4, dated May 29, 2019, 12 pages.
Notice of Reasons for Rejection for Japanese Patent Application No. 2017-520348, dated Aug. 22, 2019, 5 pages.
Second Office Action for China patent application No. 201480068628.3, dated Oct. 21, 2019, 8 pages.
Uni ProtKB Database. AR01, AR02, AR07 & TYR 1. revtrieved from https://www.uniprot.org/uniprot/ on Oct. 28, 2019.
U.S. Office Action issued for U.S. Appl. No. 15/031,618, dated Nov. 1, 2019, 31 pages.
Farrow, et al. "Stereochemical inversion of (S)-reticuline by a cytochrome P450 fusion in opium poppy", Nat Chem Biol. Sep. 2015;11(9):728-32.
De-Eknamkul, et al. "Purification and properties of 1,2-dehydroreticuline reductase from Papaver somniferum seedlings", vol. 31, Issue 3, Mar. 1992, pp. 813-821.
Communication, The Extended European Search Report for European patent application No. 1679333.4, dated May 29, 2019, 12 pages.
Hirata, et al. "1,2-Dehydroreticuline synthase, the branch point enzyme opening the morphinan biosynthetic pathway", Phytochemistry, vol. 65, 2004, pp. 1039-1046.
Communication pursuant to Rule 164(1) EPC for European patent application No. 16793332.4, dated Feb. 28, 2019, 11 pages.
Examination Report Under section 18(3) for Great Britain application No. GB1707059.0, dated Sep. 27, 2019, 6 pages.
Search and Examination Report Under section 17 and18(3) for Great Britain application No. GB1518138.1, dated Sep. 30, 2019, 9 pages.
Examination report No. 2 for standard patent application for Australian patent application No. 2016261490, dated Sep. 27, 2019, 4 pages.
U.S. Office Action for U.S. Appl. No. 15/561,358, dated Sep. 9, 2019, 14 pages.
U.S. Office Action issued for U.S. Appl. No. 15/517,761, dated Dec. 23, 2019, 35 pages.
Dang, et al. "Cloning and characterization of canadine synthase involved in noscapine biosynthesis in opium poppy", FEBS Lett. Jan. 3, 2014;588(1):198-204.
Guo, et al. "Mini-review: In vitro Metabolic Engineering for Biomanufacturing of High-value Products", Comput Struct Biotechnol J. Jan. 19, 2017;15:161-167.
Liscombe, et al. "Molecular cloning and characterization of tetrahydroprotoberberine cis-N-methyltransferase, an enzyme involved in alkaloid biosynthesis in opium poppy", J Biol Chem. May 18, 2007;282(20).
Mitchell, et al. "Circular permutation of a synthetic eukaryotic chromosome with the telomerator", PNAS, 2014,111,17003-17010.
Saez-Vasquez, et al, "Genome Organization and Function: A View from Yeast and Arabidopsis", Molecular Plant, vol. 3, No. 4, pp. 678-690, Jul. 2010.

\* cited by examiner

A

B

BENZYLISOQUINOLINE ALKALOID (BIA) PRECURSOR PRODUCING MICROBES, AND METHODS OF MAKING AND USING THE SAME

CROSS-REFERENCE TO RELATED APPLICATIONS

Pursuant to 35 U.S.C. § 119(e), this application claims priority to the filing date of U.S. Provisional Patent Application Ser. No. 62/156,701 filed on May 4, 2015; the disclosure of which application is herein incorporated by reference.

Additionally, this application is related to: U.S. patent application Ser. No. 14/211,611 now published as US 2014-0273109, which application was filed on Mar. 14, 2014; PCT Application Serial No. PCT/US2014/027833 now published as WO2014/143744, which application was filed on Mar. 14, 2014; and PCT Application Serial No. PCT/US2014/063738, which application was filed Nov. 3, 2014; the disclosures of which applications are herein incorporated by reference.

GOVERNMENT RIGHTS

This invention was made with Government support under contract 1066100 awarded by the National Science Foundation and contract DAT007886A awarded by the National Institutes of Health. The Government has certain rights in the invention.

INTRODUCTION

Benzylisoquinoline alkaloids (BIAs) are a large group of secondary metabolites from plants and other organisms. These molecules have therapeutic functions in the human body, ranging from the established analgesic and antitussive properties of morphine and codeine, to novel activities against cancer and infection observed for molecules such as berberine and sanguinarine. Supply of all these BIA molecules so that they are available to researchers and physicians is of interest. The number of synthetic reactions and requirements for selective stereochemistry means that chemical synthesis of BIAs is low yielding and not a viable means for large-scale production. Instead, for the widely used drugs codeine and morphine, the opium poppy (*Papaver somniferum*) has been bred and developed as a production crop. Intermediates in morphine biosynthesis that find use as drugs and drug precursors do not accumulate because the plant metabolism is evolved to maximize pathway flux to the final opioids. Even for end product metabolites like morphine, accumulation occurs only within specialized cells in the buds and vascular tissue and requires harsh chemical processing of harvested plant material during the extraction process, which may yield less than 2% morphine by dry weight. As such, methods for preparing BIAs are of interest.

SUMMARY

Host cells that are engineered to produce benzylisoquinoline alkaloids (BIAs) that are of interest, such as norcoclaurine (NC) and norlaudanosoline (NL), are provided. BIAs of interest may include BIA precursors, BIAs, and modifications of BIAs. The host cells may have one or more modifications selected from: a feedback inhibition alleviating mutation in an enzyme gene; a transcriptional modulation modification of a biosynthetic enzyme gene; an inactivating mutation in an enzyme; and a heterologous coding sequence. Also provided are methods of producing a BIA of interest using the host cells and compositions, e.g., kits, systems etc., that find use in methods of the invention.

An aspect of the invention provides a method for forming a product stream having a benzylisoquinoline alkaloid (BIA) product. The method comprises providing engineered yeast cells and a feedstock including nutrients and water to a batch reactor, which engineered yeast cells have at least one modification selected from the group consisting of: a feedback inhibition alleviating mutation in a biosynthetic enzyme gene native to the cell; a transcriptional modulation modification of a biosynthetic enzyme gene native to the cell; and an inactivating mutation in an enzyme native to the cell. Additionally, the method comprises, in the batch reactor, subjecting the engineered yeast cells to fermentation by incubating the engineered yeast cells for a time period of at least about 5 minutes to produce a solution comprising the BIA product and cellular material. The method also comprises using at least one separation unit to separate the BIA product from the cellular material to provide said product stream comprising the BIA product.

In another aspect, the invention provides a method for forming a product stream having a BIA product. The method comprises providing engineered yeast cells and a feedstock including nutrients and water to a reactor. The method also comprises, in the reactor, subjecting the engineered yeast cells to fermentation by incubating the engineered yeast cells for a time period of at least about 5 minutes (e.g., 5 minute or longer) to produce a solution comprising cellular material and the BIA product, wherein the solution comprises not more than one class of molecule selected from the group of protoberberine, morphinan, isopavine, aporphine and bisbenzylisoquinoline. Additionally, the method comprises using at least one separation unit to separate the BIA product from the cellular material to provide the product stream comprising the BIA product.

Another aspect of the invention provides an engineered yeast cell that produces a benzylisoquinoline alkaloid (BIA) product, the engineered yeast cell having at least one modification selected from the group consisting of: a feedback inhibition alleviating mutation in a biosynthetic enzyme gene native to the cell; a transcriptional modulation modification of a biosynthetic enzyme gene native to the cell; and an inactivating mutation in an enzyme native to the cell. The engineered yeast cell comprises at least one heterologous coding sequence encoding at least one enzyme that is selected from the group of 6OMT, CNMT, CYP80B1, CPR and 4'OMT. In some examples, the engineered yeast cell comprises a plurality of heterologous coding sequences encoding an enzyme that is selected from the group of 6OMT, CNMT, CYP80B1, CPR and 4'OMT. In some examples, the heterologous coding sequences may be operably connected. Heterologous coding sequences that are operably connected may be within the same pathway of producing a particular benzylisoquinoline alkaloid product.

An additional aspect of the invention provides a compound that comprises a benzylisoquinoline alkaloid product that is characterized as being part of at most two classes selected from the group consisting of 1-benzylisoquinoline, protoberberine, morphinan, isopavine, aporphine, and bisbenzylisoquinoline. Remaining components of the compound do not contain a detectable amount of a molecule of a non-selected class from the group of 1-benzylisoquinoline, protoberberine, morphinan, isopavine, aporphine and bisbenzylisoquinoline.

In another aspect of the invention, therapeutic agent is provided. The therapeutic agent comprises a benzylisoquinoline alkaloid product. The therapeutic agent does not contain a detectable amount of an impurity selected from the group consisting of codeine-O(6)-methyl ether, 8,14-dihydroxy-7,8-dihydrocodeinone and tetrahydrothebaine.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
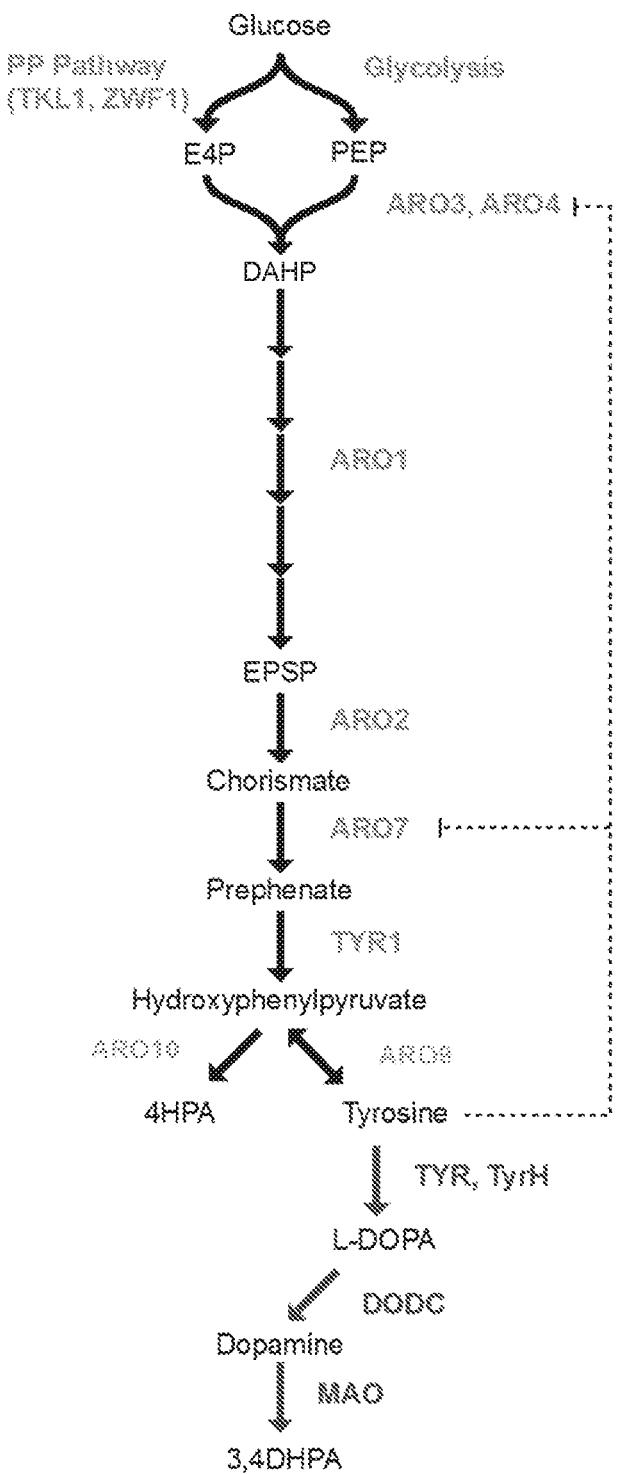
FIG. 1 illustrates the biosynthetic pathway from glucose to tyrosine and other BIA precursor molecules.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It is noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims are drafted to exclude any optional element. As such, this statement is intended to serve as antecedent basis for use of such exclusive terminology as "solely," "only" and the like in connection with the recitation of claim elements, or use of a "negative" limitation.

As used herein, the terms "determining," "measuring," "assessing," and "assaying" are used interchangeably and include both quantitative and qualitative determinations.

As used herein, the term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein, the term "isolated," refers to an moiety of interest that is at least 60% free, at least 75% free, at least 90% free, at least 95% free, at least 98% free, and even at least 99% free from other components with which the moiety is associated with prior to purification.

As used herein, the term "encoded by" refers to a nucleic acid sequence which codes for a polypeptide sequence, wherein the polypeptide sequence or a portion thereof contains an amino acid sequence of 3 or more amino acids, such as 5 or more, 8 or more, 10 or more, 15 or more, or 20 or more amino acids from a polypeptide encoded by the nucleic acid sequence. Also encompassed by the term are polypeptide sequences that are immunologically identifiable with a polypeptide encoded by the sequence.

A "vector" is capable of transferring gene sequences to target cells. As used herein, the terms, "vector construct," "expression vector," and "gene transfer vector," are used interchangeably to mean any nucleic acid construct capable of directing the expression of a gene of interest and which may transfer gene sequences to target cells, which is accomplished by genomic integration of all or a portion of the vector, or transient or inheritable maintenance of the vector as an extrachromosomal element. Thus, the term includes cloning, and expression vehicles, as well as integrating vectors.

An "expression cassette" includes any nucleic acid construct capable of directing the expression of a gene/coding sequence of interest, which is operably linked to a promoter of the expression cassette. Such cassette is constructed into a "vector," "vector construct," "expression vector," or "gene transfer vector," in order to transfer the expression cassette into target cells. Thus, the term includes cloning and expression vehicles, as well as viral vectors.

A "plurality" contains at least 2 members. In certain cases, a plurality may have 10 or more, such as 100 or more, 1000 or more, 10,000 or more, 100,000 or more, $10^6$ or more, $10^7$ or more, $10^8$ or more, or $10^9$ or more members.

Numeric ranges are inclusive of the numbers defining the range.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more, and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

Other definitions of terms may appear throughout the specification.

DETAILED DESCRIPTION

Host cells that are engineered to produce benzylisoquinoline alkaloids (BIAs) that are of interest, such as norcoclaurine (NC) and norlaudanosoline (NL), are provided. The host cells may have one or more engineered modifications selected from: a feedback inhibition alleviating mutation in an enzyme gene; a transcriptional modulation modification of a biosynthetic enzyme gene; an inactivating mutation in an enzyme; and a heterologous coding sequence. Also provided are methods of producing a BIA of interest using the host cells and compositions, e.g., kits, systems etc., that find use in methods of the invention.

Before the present invention is described in greater detail, it is to be understood that this invention is not limited to particular embodiments described, and as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein may also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method is carried out in the order of events recited or in any other order which is logically possible.

In further describing the subject invention, BIA precursors of interest, BIAs, and modifications of BIAs are described first in greater detail, followed by host cells for producing the same. Next, methods of interest in which the host cells find use are reviewed. Kits that may be used in practicing methods of the invention are also described.

Benzylisoquinoline Alkaloid (BIA) Precursors

As summarized above, host cells which produce benzylisoquinoline alkaloid precursors (BIA precursors) are provided. The BIA precursor may be any intermediate or precursor compound in a synthetic pathway (e.g., as described herein) that leads to the production of a BIA of interest (e.g., as described herein). In some cases, the BIA precursor has a structure that may be characterized as a BIA or a derivative thereof. In certain cases, the BIA precursor has a structure that may be characterized as a fragment of a BIA. In some cases, the BIA precursor is an early BIA. As used herein, by "early BIA" is meant an early intermediate in the synthesis of a BIA of interest in a cell, where the early BIA is produced by a host cell from a host cell feedstock or simple starting compound. In some cases, the early BIA is a BIA intermediate that is produced by the subject host cell solely from a host cell feedstock (e.g., a carbon and nutrient source) without the need for addition of a starting compound to the cells. The term early BIA may refer to a precursor of a BIA end product of interest whether or not the early BIA may itself be characterized as a benzylisoquinoline alkaloid.

In some cases, the BIA precursor is an early BIA, such as a pre-reticuline benzylisoquinoline alkaloid. As such, host cells which produce pre-reticuline benzylisoquinoline alkaloids (pre-reticuline BIAs) are provided. Reticuline is a major branch point intermediate of interest in the synthesis of downstream BIAs via cell engineering efforts to produce end products such as opioid products. The subject host cells may produce BIA precursors from simple and inexpensive starting materials that may find use in the production of reticuline and downstream BIA end products.

As used herein, the terms "pre-reticuline benzylisoquinoline alkaloid", "pre-reticuline BIA", and "pre-reticuline BIA precursor" are used interchangeably and refer to a biosynthetic precursor of reticuline whether or not the structure of the reticuline precursor itself is characterized as a benzylisoquinoline alkaloid. The term pre-reticuline BIA is meant to include biosynthetic precursors, intermediates and metabolites thereof, of any convenient member of a host cell biosynthetic pathway that may lead to reticuline. In some cases, the pre-reticuline BIA includes a benzylisoquinoline alkaloid fragment, such as a benzyl fragment, a quinoline fragment or a precursor or derivative thereof. In certain instances, the pre-reticuline BIA has a structure that may be characterized as a benzylisoquinoline alkaloid or a derivative thereof.

Figure 3:
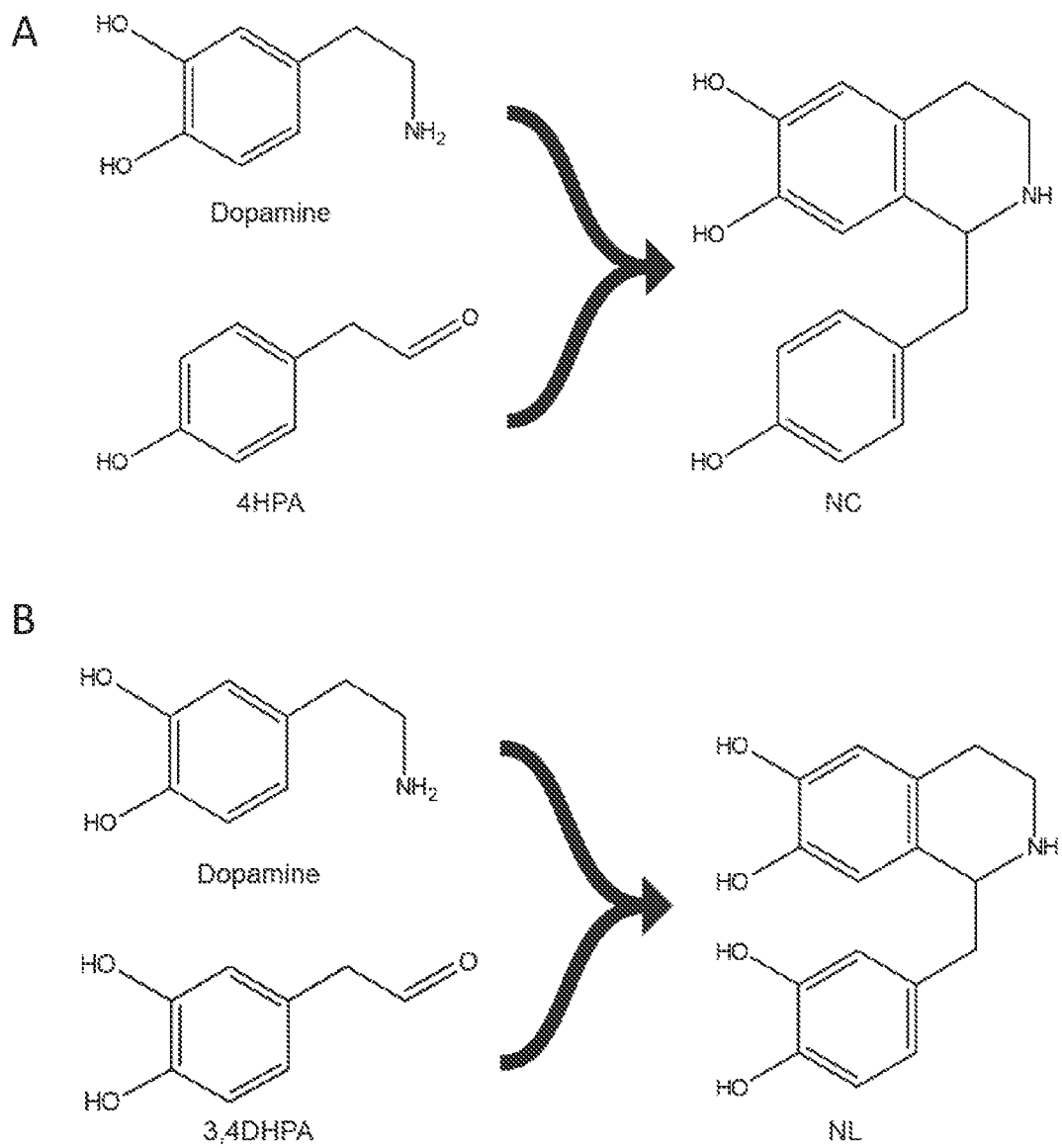
FIG. 3 illustrates the synthesis of NC (A) and NL (B) from precursor molecules.

BIA precursors of interest include, but are not limited to, norcoclaurine (NC) and norlaudanosoline (NL), as well as NC and NL precursors, such as tyrosine, tyramine, 4-hydroxyphenylacetaldehyde (4-HPA), 4-hydroxyphenylpyruvic acid (4-HPPA), L-3,4-dihydroxyphenylalanine (L-DOPA), 3,4-dihydroxyphenylacetaldehyde (3,4-DHPA), and dopamine. In some embodiments, the one or more BIA precursors are 3,4-dihydroxyphenylacetaldehyde (3,4-DHPA) and dopamine. In certain instances, the one or more BIA precursors are 4-hydroxyphenylacetaldehyde (4-HPA) and dopamine. FIGS. 3A and 3B illustrate the synthesis of NC and NL, respectively from precursor molecules via a Pictet-Spengler condensation reaction, where the reaction may occur spontaneously or may by catalyzed by any convenient enzymes.

Synthetic pathways to a BIA precursor may be generated in the host cells, and may start with any convenient starting compound(s) or materials. FIG. 1 illustrates a synthetic pathway of interest to BIA precursors starting from glucose. The starting material may be non-naturally occurring or the starting material may be naturally occurring in the host cell. Any convenient compounds and materials may be used as the starting material, based upon the synthetic pathway present in the host cell. The source of the starting material may be from the host cell itself, e.g., tyrosine, or the starting material may be added or supplemented to the host cell from an outside source. As such, in some cases, the starting compound refers to a compound in a synthetic pathway of the cell that is added to the host cell from an outside source that is not part of a growth feedstock or cell growth media.

Starting compounds of interest include, but are not limited to, dopamine, 4-HPA, 4-HPPA, as well as any of the compounds shown in FIG. 1. For example, if the host cells are growing in liquid culture, the cell media may be supplemented with the starting material, which is transported into the cells and converted into the desired products by the cell. Starting materials of interest include, but are not limited to, inexpensive feedstocks and simple precursor molecules. In some cases, the host cell utilizes a feedstock including a simple carbon source as the starting material, which the host cell utilizes to produce compounds of the synthetic pathway of the cell. The host cell growth feedstock may include one or more components, such as a carbon source such as cellulose, starch, free sugars and a nitrogen source, such as ammonium salts or inexpensive amino acids. In some cases, a growth feedstock that finds use as a starting material may be derived from a sustainable source, such as biomass grown on marginal land, including switchgrass and algae, or biomass waste products from other industrial or farming activities.

Benzylisoquinoline Alkaloids (BIAs)

As summarized above, host cells which produce benzylisoquinoline alkaloids (BIA) of interest are provided. In some embodiments, the engineered strains of the invention will provide a platform for producing benzylisoquinoline alkaloids of interest and modifications thereof across several structural classes including, but not limited to, benzylisoquinolines, protoberberines, protopines, benzophenanthridines, promorphinans, morphinans, secoberberines, phthalideisoquinolines, aporphines, bisbenzylisoquinolines, and others. Each of these classes is meant to include biosynthetic precursors, intermediates, and metabolites thereof, of any convenient member of a host cell biosynthetic pathway that may lead to a member of the class. Non-limiting examples of compounds are given below for each of these structural classes. In some embodiments, the structure of a given example may or may not be characterized itself as a benzylisoquinoline alkaloid. The present chemical entities are meant to include all possible isomers, including single enantiomers, racemic mixtures, optically pure forms, mixtures of diastereomers and intermediate mixtures.

Benzylisoquinolines may include, but are not limited to, norcoclaurine, norlaudanosoline, coclaurine, 3'-hydroxycoclaurine, 4'-O-methylnorlaudanosoline, 4'-O-methyl-laudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine and orientaline.

Protoberberines may include, but are not limited to, scoulerine, cheilanthifoline, stylopine, nandinine, jatrorrhizine, stepholidine, discretamine, cis-N-methylstylopine, tetrahydrocolumbamine, palmatine, tetrahydropalmatine, columbamine, canadine, N-methylcanadine, 1-hydroxycanadine, berberine, N-methyl-ophiocarpine, 1,13-dihydroxy-N-methylcanadine and 1-hydroxy-10-O-acetyl-N-methylcanadine.

Protopines may include, but are not limited to, protopine, 6-hydroxyprotopine, allocryptopine, cryptopine, muramine and thalictricine.

Benzophenanthridines may include, but are not limited to, dihydrosanguinarine, sanguinarine, dihydrocheilirubine, cheilirubine, dihydromarcapine, marcapine and chelerythrine.

Promorphinans may include, but are not limited to, salutaridine, salutaridinol and salutaridinol-7-O-acetate.

Morphinans may include, but are not limited to, thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone.

Secoberberines may include, but are not limited to, 4'-O-desmethylmacrantaldehyde, 4'-O-desmethylpapaveroxine, 4'-O-desmethyl-3-O-acetylpapaveroxine and 3-O-acetyelpapaveroxine.

Phthalideisoquinolines may include, but are not limited to, narcotolinehemiacetal, narcotinehemiacetal, narcotoline and noscapine.

Aporphines may include, but are not limited to, magnoflorine, corytuberine, apomorphine, boldine, isoboldine, isothebaine, isocorytuberine and glaufine.

Bisbenzylisoquinolines may include, but are not limited to, berbamunine, guattgaumerine, dauricine and liensinine.

Other compounds that may be produced by the engineered strains of the invention may include, but are not limited to, rhoeadine, pavine, isopavine and cularine.

In certain embodiments, the engineered strains of the invention may provide a platform for producing compounds related to tetrahydrobiopterin synthesis including, but not limited to, dihydroneopterin triphosphate, 6-pyruvoyl tetrahydropterin, 5,6,7,8-tetrahydrobiopterin, 7,8-dihydrobiopterin, tetrahydrobiopterin 4a-carbinolamine, quinoid dihydrobiopterin and biopterin.

Host Cells

As summarized above, one aspect of the invention is a host cell that produces one or more BIAs of interest. Any convenient cells may be utilized in the subject host cells and methods. In some cases, the host cells are non-plant cells. In some instances, the host cells may be characterized as microbial cells. In certain cases, the host cells are insect cells, mammalian cells, bacterial cells, or yeast cells. Any convenient type of host cell may be utilized in producing the subject BIA-producing cells, see, e.g., US2008/0176754 now published as U.S. Pat. No. 8,975,063, US2014/0273109 and WO2014/143744; the disclosures of which are incorporated by reference in their entirety. Host cells of interest include, but are not limited to, bacterial cells, such as *Bacillus subtilis, Escherichia coli, Streptomyces* and *Salmonella typhimuium* cells, insect cells such as *Drosophila melanogaster* S2 and *Spodoptera frugiperda* Sf9 cells, and yeast cells such as *Saccharomyces cerevisiae, Schizosaccharomyces pombe*, and *Pichia pastoris* cells. In some embodiments, the host cells are yeast cells or *E. coli* cells. In some cases, the host cell is a yeast cell. In some instances the host cell is from a strain of yeast engineered to produce a BIA of interest. Any of the host cells described in US2008/0176754 now published as U.S. Pat. No. 8,975,063, US2014/0273109 and WO2014/143744, may be adapted for use in the subject cells and methods. In certain embodiments, the yeast cells may be of the species *Saccharomyces cerevisiae* (*S. cerevisiae*). In certain embodiments, the yeast cells may be of the species *Schizosaccharomyces pombe*. In certain embodiments, the yeast cells may be of the species *Pichia pastoris*. Yeast is of interest as a host cell because cytochrome P450 proteins, which are involved in some biosynthetic pathways of interest, are able to fold properly into the endoplasmic reticulum membrane so that their activity is maintained. Yeast strains of interest that find use in the invention include, but are not limited to, CEN.PK (Genotype: MATa/α ura3-52/ura3-52 trp1-289/trp1-289 leu2-3_112/leu2-3_112 his3 Δ1/his3 Δ1 MAL2-8C/MAL2-8C SUC2/SUC2), S288C, W303, D273-10B, X2180, A364A, Σ1278B, AB972, SK1, and FL100. In certain cases, the yeast strain is any of S288C (MATα; SUC2 mal mel gal2 CUP1 flo1 flo8-1 hap1), BY4741 (MATα; his3Δ1; leu2Δ0; met15Δ0; ura3Δ0), BY4742 (MATα; his3Δ1; leu2Δ0; lys2Δ0; ura3Δ0), BY4743 (MATa/MATα; his3Δ1/his3Δ1; leu2Δ0/leu2Δ0; met15Δ0/MET15; LYS2/lys2Δ0; ura3Δ0/ura3Δ0), and WAT11 or W(R), derivatives of the W303-B strain (MATa; ade2-1; his3-11, -15; leu2-3, -112; ura3-1; canR; cyr+) which express the *Arabidopsis thaliana* NADPH-P450 reductase ATR1 and the yeast NADPH-P450 reductase CPR1, respectively. In another embodiment, the yeast cell is W303alpha (MATα; his3-11,15 trp1-1 leu2-3 ura3-1 ade2-1). The identity and genotype of additional yeast strains of interest may be found at EUROSCARF (web.uni-frankfurt.de/fb15/mikro/euroscarf/col_index.html).

The host cells may be engineered to include one or more modifications (such as two or more, three or more, four or more, five or more, or even more modifications) that provide for the production of BIAs of interest. In some cases, by modification is meant a genetic modification, such as a mutation, addition, or deletion of a gene or fragment thereof, or transcription regulation of a gene or fragment thereof. In some cases, the one or more (such as two or more, three or more, or four or more) modifications is selected from: a feedback inhibition alleviating mutation in a biosynthetic enzyme gene native to the cell; a transcriptional modulation modification of a biosynthetic enzyme gene native to the cell; an inactivating mutation in an enzyme native to the cell; and a heterologous coding sequence that encodes an enzyme. A cell that includes one or more modifications may be referred to as a modified cell.

A modified cell may overproduce one or more precursor BIA, BIA, or modified BIA molecules. By overproduce is meant that the cell has an improved or increased production of a BIA molecule of interest relative to a control cell (e.g., an unmodified cell). By improved or increased production is meant both the production of some amount of the BIA of interest where the control has no BIA precursor production, as well as an increase of about 10% or more, such as about 20% or more, about 30% or more, about 40% or more, about 50% or more, about 60% or more, about 80% or more, about 100% or more, such as 2-fold or more, such as 5-fold or more, including 10-fold or more in situations where the control has some BIA of interest production.

In some cases, the host cell is capable of producing an increased amount of norcoclaurine relative to a control host cell that lacks the one or more modifications (e.g., as described herein). In certain instances, the increased amount of norcoclaurine is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some cases, the host cell is capable of producing an increased amount of norlaudanosoline relative to a control host cell that lacks the one or more modifications (e.g., as described herein). In certain instances, the increased amount of norlaudanosoline is about 10% or more relative to the control host cell, such as about 20% or more, about 30% or more, about 40% or more, about 50% or more, about 60% or more, about 80% or more, about 100% or more, 2-fold or more, 5-fold or more, or even 10-fold or more relative to the control host cell.

In some embodiments, the host cell is capable of producing a 10% or more yield of norcoclaurine from a starting compound such as tyrosine, such as 20% or more, 30% or more, 40% or more, 50% or more, 60% or more, 70% or more, 80% or more, or even 90% or more yield of norcoclaurine from a starting compound.

In some embodiments, the host cell is capable of producing a 10% or more yield of norlaudanosoline from a starting compound such as tyrosine, such as 20% or more, 30% or more, 40% or more, 50% or more, 60% or more, 70% or more, 80% or more, or even 90% or more yield of norlaudanosoline from a starting compound.

In some embodiments, the host cell overproduces one or more BIA of interest molecule selected from the group consisting of tyrosine, 4-hydroxyphenylacetaldehyde (4-HPA), L-3,4-dihydroxyphenylalanine (L-DOPA), 3,4-dihydroxyphenylacetaldehyde (3,4-DHPA) and dopamine.

Any convenient combinations of the one or more modifications may be included in the subject host cells. In some cases, two or more (such as two or more, three or more, or four or more) different types of modifications are included. In certain instances, two or more (such as three or more, four or more, five or more, or even more) distinct modifications of the same type of modification are included in the subject cells.

In some embodiments of the host cell, when the cell includes one or more heterologous coding sequences that encode one or more enzymes, it includes at least one additional modification selected from the group consisting of: a feedback inhibition alleviating mutations in a biosynthetic enzyme gene native to the cell; a transcriptional modulation modification of a biosynthetic enzyme gene native to the cell; and an inactivating mutation in an enzyme native to the cell. In certain embodiments of the host cell, when the cell includes one or more feedback inhibition alleviating mutations in one or more biosynthetic enzyme genes native to the cell, it includes a least one additional modification selected from the group consisting of: a transcriptional modulation modification of a biosynthetic enzyme gene native to the cell; an inactivating mutation in an enzyme native to the cell; and a heterologous coding sequence that encode an enzyme. In some embodiments of the host cell, when the cell includes one or more transcriptional modulation modifications of one or more biosynthetic enzyme genes native to the cell, it includes at least one additional modification selected from the group consisting of: a feedback inhibition alleviating mutation in a biosynthetic enzyme gene native to the cell; an inactivating mutation in an enzyme native to the cell; and a heterologous coding sequence that encodes an enzyme. In certain instances of the host cell, when the cell includes one or more inactivating mutations in one or more enzymes native to the cell, it includes at least one additional modification selected from the group consisting of: a feedback inhibition alleviating mutation in a biosynthetic enzyme gene native to the cell; a transcriptional modulation modification of a biosynthetic enzyme gene native to the cell; and a heterologous coding sequence that encodes an enzyme.

In certain embodiments of the host cell, the cell includes one or more feedback inhibition alleviating mutations in one or more biosynthetic enzyme genes native to the cell; and one or more transcriptional modulation modifications of one or more biosynthetic enzyme gene native to the cell. In certain embodiments of the host cell, the cell includes one or more feedback inhibition alleviating mutations in one or more biosynthetic enzyme genes native to the cell; and one or more inactivating mutations in an enzyme native to the cell. In certain embodiments of the host cell, the cell includes one or more feedback inhibition alleviating mutations in one or more biosynthetic enzyme genes native to the cell; and one or more heterologous coding sequences. In some embodiments, the host cell includes one or more modifications (e.g., as described herein) that include one or more of the genes of interest described in Table 1.

Feedback Inhibition Alleviating Mutations

In some instances, the host cells are cells that include one or more feedback inhibition alleviating mutations (such as two or more, three or more, four or more, five or more, or even more) in one or more biosynthetic enzyme genes of the cell. In some cases, the one or more biosynthetic enzyme genes are native to the cell (e.g., is present in an unmodified cell). As used herein, the term "feedback inhibition alleviating mutation" refers to a mutation that alleviates a feedback inhibition control mechanism of a host cell. Feedback inhibition is a control mechanism of the cell in which an enzyme in the synthetic pathway of a regulated compound is inhibited when that compound has accumulated to a certain level, thereby balancing the amount of the compound in the cell. In some instances, the one or more feedback inhibition alleviating mutations is in an enzyme described in a synthetic pathway of FIG. 1 or FIG. 2. A mutation that alleviates feedback inhibition reduces the inhibition of a regulated enzyme in the cell of interest relative to a control cell and provides for an increased level of the regulated compound or a downstream biosynthetic product thereof. In some cases, by alleviating inhibition of the regulated enzyme is meant that the $IC_{50}$ of inhibition is increased by 2-fold or more, such as by 3-fold or more, 5-fold or more, 10-fold or more, 30-fold or more, 100-fold or more, 300-fold or more, 1000-fold or more, or even more. By increased level is meant a level that is 110% or more of that of the regulated compound in a control cell or a downstream product thereof, such as 120% or more, 130% or more, 140% or more, 150% or more, 160% or more, 170% or more, 180% or more, 190% or more, or 200% or more, such as at least 3-fold or more, at least 5-fold or more, at least 10-fold or more or even more of the regulated compound in the host cell or a downstream product thereof.

A variety of feedback inhibition control mechanisms and biosynthetic enzymes native to the host cell that are directed to regulation of levels of BIA precursors may be targeted for alleviation in the host cell. The host cell may include one or more feedback inhibition alleviating mutations in one or more biosynthetic enzyme genes native to the cell. The mutation may be located in any convenient biosynthetic enzyme genes native to the host cell where the biosynthetic enzyme is subject to regulatory control. In some embodiments, the one or more biosynthetic enzyme genes encode one or more enzymes selected from a 3-deoxy-d-arabinose-heptulosonate-7-phosphate (DAHP) synthase and a chorismate mutase. In some embodiments, the one or more biosynthetic enzyme genes encode a 3-deoxy-d-arabinose-heptulosonate-7-phosphate (DAHP) synthase. In some instances, the one or more biosynthetic enzyme genes encode a chorismate mutase. In certain instances, the one or more feedback inhibition alleviating mutations are present in a biosynthetic enzyme gene selected from ARO4 and ARO7. In certain instances, the one or more feedback inhibition alleviating mutations are present in a biosynthetic enzyme gene that is ARO4. In certain instances, the one or more feedback inhibition alleviating mutations are present in a biosynthetic enzyme gene that is ARO7. In some embodiments, the host cell includes one or more feedback inhibition alleviating mutations in one or more biosynthetic enzyme genes such as one of those genes described in Table 1.

Any convenient numbers and types of mutations may be utilized to alleviate a feedback inhibition control mechanism. As used herein, the term "mutation" refers to a deletion, insertion, or substitution of an amino acid(s) residue or nucleotide(s) residue relative to a reference sequence or motif. The mutation may be incorporated as a directed mutation to the native gene at the original locus. In some cases, the mutation may be incorporated as an additional copy of the gene introduced as a genetic integration at a separate locus, or as an additional copy on an episomal vector such as a 2µ or centromeric plasmid. In certain instances, the feedback inhibited copy of the enzyme is under the native cell transcriptional regulation. In some instances, feedback inhibited copy of the enzyme is introduced with engineered constitutive or dynamic regulation of protein expression by placing it under the control of a synthetic promoter.

In certain embodiments, the one or more feedback inhibition alleviating mutations are present in the ARO4 gene. ARO4 mutations of interest include, but are not limited to, substitution of the lysine residue at position 229 with a leucine, a substitution of the glutamine residue at position 166 with a lysine residue, or a mutation as described by Hartmann M, et al. ((2003) Proc. Nat'l Acad. Sci. USA 100(3):862-867) or Fukuda et al. ((1992) J Ferment Bioeng 74(2):117-119). In some instances, mutations for conferring feedback inhibition are selected from a mutagenized library of enzyme mutants. Examples of such selections include rescue of growth of o-fluoro-D,L-phenylalanine or growth of aro3 mutant yeast strains in media with excess tyrosine as described by Fukuda et al. ((1990) Breeding of Brewing Yeast Producing a Large Amount of Beta-Phenylethyl Alcohol and Beta-Phenylethyl Acetate. Agr Biol Chem Tokyo 54(1):269-271).

ARO7 mutations of interest include, but are not limited to, substitution of the threonine residue at position 226 with an isoleucine, as described by Schmidheini et al. ((1989), J Bacteriol 171(3):1245-1253) and additional mutations conferring feedback inhibition selected from a mutagenized library of microbial chorismate mutase mutants. Examples of such selections include assays for 5-methyltryptophan sensitivity or increased production of melanin pigments in strains expressing heterologous tyrosinase enzymes (1.9) in the absence of externally fed tyrosine.

In certain embodiments, the host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more feedback inhibition alleviating mutations, such as 1, 2, 3, 4, 5, 6, 7, 8, 9, 10, 11, 12, 13, 14 or 15 feedback inhibition alleviating mutations in one or more biosynthetic enzyme genes native to the host cell.

Transcriptional Modulation Modifications

The host cells may include one or more transcriptional modulation modifications (such as two or more, three or more, four or more, five or more, or even more modifications) of one or more biosynthetic enzyme genes of the cell. In some cases, the one or more biosynthetic enzyme genes are native to the cell. Any convenient biosynthetic enzyme genes of the cell may be targeted for transcription modulation. By transcription modulation is meant that the expression of a gene of interest in a modified cell is modulated, e.g., increased or decreased, enhanced or repressed, relative to a control cell (e.g., an unmodified cell). In some cases, transcriptional modulation of the gene of interest includes increasing or enhancing expression. By increasing or enhancing expression is meant that the expression level of the gene of interest is increased by 2-fold or more, such as by 5-fold or more and sometimes by 25-, 50-, or 100-fold or more and in certain embodiments 300-fold or more or higher, as compared to a control, i.e., expression in the same cell not modified (e.g., by using any convenient gene expression assay). Alternatively, in cases where expression of the gene of interest in a cell is so low that it is undetectable, the expression level of the gene of interest is considered to be increased if expression is increased to a level that is easily detectable. In certain instances, transcriptional modulation of the gene of interest includes decreasing or repressing expression. By decreasing or repressing expression is meant that the expression level of the gene of interest is decreased by 2-fold or more, such as by 5-fold or more and sometimes by 25-, 50-, or 100-fold or more and in certain embodiments 300-fold or more or higher, as compared to a control. In some cases, expression is decreased to a level that is undetectable. Modifications of host cell processes of interest that may be adapted for use in the subject host cells are described in U.S. Publication No. 20140273109 (Ser. No. 14/211,611) by Smolke et al., the disclosure of which is herein incorporated by reference in its entirety.

Any convenient biosynthetic enzyme genes may be transcriptionally modulated, and include but are not limited to, those biosynthetic enzymes described in FIG. 1, such as ARO3, ARO4, ARO1, ARO7, TYR1, TYR, TyrH, DODC, MAO, ARO10, ARO9, and TKL. In some instances, the one or more biosynthetic enzyme genes is selected from ARO10, ARO9, and TKL. In some cases, the one or more biosynthetic enzyme genes is ARO10. In certain instances, the one or more biosynthetic enzyme genes is ARO9. In some embodiments, the one or more biosynthetic enzyme genes is TKL. In some embodiments, the host cell includes one or more transcriptional modulation modifications to one or more genes such as one of those genes described in Table 1. In some embodiments, the host cell includes one or more transcriptional modulation modifications to one or more genes such as one of those genes described in a synthetic pathway of one of FIGS. 1 and 2.

In some embodiments, the transcriptional modulation modification includes substitution of a strong promoter for a native promoter of the one or more biosynthetic enzyme genes or the expression of an additional copy(ies) of the gene or genes under the control of a strong promoter. The promoters driving expression of the genes of interest may be constitutive promoters or inducible promoters, provided that the promoters may be active in the host cells. The genes of interest may be expressed from their native promoters, or non-native promoters may be used. Although not a requirement, such promoters should be medium to high strength in the host in which they are used. Promoters may be regulated or constitutive. In some embodiments, promoters that are not glucose repressed, or repressed only mildly by the presence of glucose in the culture medium, are used. There are numerous suitable promoters, examples of which include promoters of glycolytic genes such as the promoter of the *B. subtilis* tsr gene (encoding fructose biphosphate aldolase) or GAPDH promoter from yeast *S. cerevisiae* (coding for glyceraldehyde-phosphate dehydrogenase) (Bitter G. A., *Meth. Enzymol.* 152:673 684 (1987)). Other strong promoters of interest include, but are not limited to, the ADHI promoter of baker's yeast (Ruohonen L., et al, *J. Biotechnol.* 39:193 203 (1995)), the phosphate-starvation induced promoters such as the PHO5 promoter of yeast (Hinnen, A., et al, in *Yeast Genetic Engineering*, Barr, P. J., et al. eds, Butterworths (1989), the alkaline phosphatase promoter from *B. licheniformis* (Lee. J. W. K., et al., *J. Gen. Microbiol.* 137:1127 1133 (1991)), GPD1 and TEF1. Yeast promoters of interest include, but are not limited to, inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-alpha promoter (TEF), cytochrome c-oxidase promoter (CYC1), MRP7 promoter, etc. In some instances, the strong promoter is GPD1. In certain instances, the strong promoter is TEF1. Autonomously replicating yeast expression vectors containing promoters inducible by hormones such as glucocorticoids, steroids, and thyroid hormones are also known and include, but are not limited to, the glucorticoid responsive element (GRE) and thyroid hormone responsive element (TRE), see e.g., those promoters described in U.S. Pat. No. 7,045,290. Vectors containing constitutive or inducible promoters such as alpha factor, alcohol oxidase, and PGH may be used. Additionally any promoter/enhancer combination (as per the Eukaryotic Promoter Data Base EPDB) could also be used to drive expression of genes of interest. It is understood that any convenient promoters specific to the host cell may be selected, e.g., $E.\ coli$. In some cases, promoter selection may be used to optimize transcription, and hence, enzyme levels to maximize production while minimizing energy resources.

Inactivating Mutations

Figure 2:
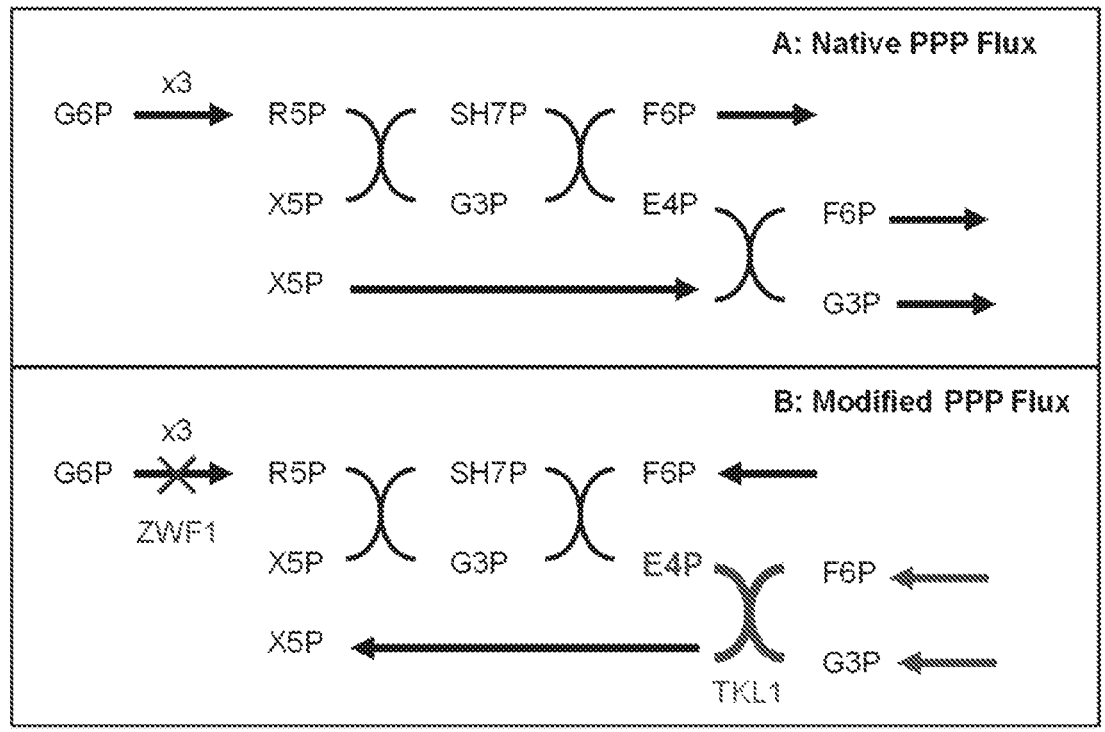
FIG. 2 illustrates the effect of ZWF1 knockout and TKL1 over-expression on the pentose phosphate pathway (PPP). A: native PPP flux, B: Modified PPP flux.

The host cells may include one or more inactivating mutations to an enzyme of the cell (such as two or more, three or more, four or more, five or more, or even more). The inclusion of one or more inactivating mutations may modify the flux of a synthetic pathway of a host cell to increase the levels of a BIA of interest or a desirable enzyme or precursor leading to the same. In some cases, the one or more inactivating mutations are to an enzyme native to the cell. FIG. 2 illustrates a native pentose phosphate pathway (PPP) flux and modified PPP flux where that involves inactivation of ZWF1 enzyme. As used herein, by "inactivating mutation" is meant one or more mutations to a gene or regulatory DNA sequence of the cell, where the mutation(s) inactivates a biological activity of the protein expressed by that gene of interest. In some cases, the gene is native to the cell. In some instances, the gene encodes an enzyme that is inactivated and is part of or connected to the synthetic pathway of a BIA of interest produced by the host cell. In some instances, an inactivating mutation is located in a regulatory DNA sequence that controls a gene of interest. In certain cases, the inactivating mutation is to a promoter of a gene. Any convenient mutations (e.g., as described herein) may be utilized to inactivate a gene or regulatory DNA sequence of interest. By "inactivated" or "inactivates" is meant that a biological activity of the protein expressed by the mutated gene is reduced by 10% or more, such as by 20% or more, 30% or more, 40% or more, 50% or more, 60% or more, 70% or more, 80% or more, 90% or more, 95% or more, 97% or more, or 99% or more, relative to a control protein expressed by a non-mutated control gene. In some cases, the protein is an enzyme and the inactivating mutation reduces the activity of the enzyme.

In some embodiments, the cell includes an inactivating mutation in an enzyme native to the cell. Any convenient enzymes may be targeted for inactivation. Enzymes of interest include, but are not limited to those enzymes, described in FIGS. 1 and 2 whose action in the synthetic pathway of the host cell tends to reduce the levels of a BIA of interest. In some cases, the enzyme has glucose-6-phosphate dehydrogenase activity. In certain embodiments, the enzyme that includes an inactivating mutation is ZWF1 (see e.g., FIG. 2). In some cases, the enzyme has alcohol dehydrogenase activity. In some embodiments, the enzyme that includes an inactivating mutation is selected from ADH2, ADH3, ADH4, ADH5, ADH6, ADH7, and SFA1. In certain embodiments, the enzyme that includes an inactivating mutation(s) is ADH2. In certain embodiments, the enzyme that includes an inactivating mutation(s) is ADH3. In certain embodiments, the enzyme that includes an inactivating mutation(s) is ADH4. In certain embodiments, the enzyme that includes an inactivating mutation(s) is ADH5. In certain embodiments, the enzyme that includes an inactivating mutation(s) is ADH6. In certain embodiments, the enzyme that includes an inactivating mutation(s) is ADH7. In some cases, the enzyme has aldehyde oxidoreductase activity. In certain embodiments, the enzyme that includes an inactivating mutation is selected from ALD2, ALD3, ALD4, ALD5, and ALD6. In certain embodiments, the enzyme that includes an inactivating mutation(s) is ALD2. In certain embodiments, the enzyme that includes an inactivating mutation(s) is ALD3. In certain embodiments, the enzyme that includes an inactivating mutation(s) is ALD4. In certain embodiments, the enzyme that includes an inactivating mutation(s) is ALD5. In certain embodiments, the enzyme that includes an inactivating mutation(s) is ALD6. In some embodiments, the host cell includes one or more inactivating mutations to one or more genes described in Table 1.

Heterologous Coding Sequences

In some instances, the host cells are cells that harbor one or more heterologous coding sequences (such as two or more, three or more, four or more, five or more, or even more) which encode activity(ies) that enable the host cells to produce desired BIAs of interest, e.g., as described herein. As used herein, the term "heterologous coding sequence" is used to indicate any polynucleotide that codes for, or ultimately codes for, a peptide or protein or its equivalent amino acid sequence, e.g., an enzyme, that is not normally present in the host organism and may be expressed in the host cell under proper conditions. As such, "heterologous coding sequences" includes multiple copies of coding sequences that are normally present in the host cell, such that the cell is expressing additional copies of a coding sequence that are not normally present in the cells. The heterologous coding sequences may be RNA or any type thereof, e.g., mRNA, DNA or any type thereof, e.g., cDNA, or a hybrid of RNA/DNA. Coding sequences of interest include, but are not limited to, full-length transcription units that include such features as the coding sequence, introns, promoter regions, 3'-UTRs, and enhancer regions.

In examples, the engineered host cell comprises a plurality of heterologous coding sequences each encoding an enzyme. In some examples, the plurality of enzymes encoded by the plurality of heterologous coding sequences may be distinct from each other. In some examples, some the plurality of enzymes encoded by the plurality of heterologous coding sequences may be distinct from each other and some of the plurality of enzymes encoded by the plurality of heterologous coding sequences may be duplicate copies.

In some examples, the heterologous coding sequences may be operably connected. Heterologous coding sequences that are operably connected may be within the same pathway of producing a particular benzylisoquinoline alkaloid product. In some examples, the operably connected heterologous coding sequences may be directly sequential along the pathway of producing a particular benzylisoquinoline alkaloid product. In some examples, the operably connected heterologous coding sequences may have one or more native enzymes between one or more of the enzymes encoded by the plurality of heterologous coding sequences. In some examples, the heterologous coding sequences may have one or more heterologous enzymes between one or more of the enzymes encoded by the plurality of heterologous coding sequences. In some examples, the heterologous coding sequences may have one or more non-native enzymes between one or more of the enzymes encoded by the plurality of heterologous coding sequences.

In some embodiments, the host cell includes norcoclaurine (NC) synthase activity. Any convenient NC synthase enzymes find use in the subject host cells. NC synthase enzymes of interest include, but are not limited to, enzymes such as EC 4.2.1.78, as described in Table 1. In certain embodiments, the host cell includes a heterologous coding sequence for an NC synthase or an active fragment thereof. In some instances, the host cell includes one or more heterologous coding sequences for one or more enzymes or active fragments thereof that convert tyrosine to L-DOPA. In certain cases, the one or more enzymes is selected from bacterial tyrosinases, eukaryotic tyrosinases (e.g., EC 1.14.18.1) and tyrosine hydroxylases (e.g., EC 1.14.16.2.) In some instances, the host cell includes one or more heterologous coding sequences for one or more enzymes or active fragments thereof that convert L-DOPA to dopamine (e.g., EC 4.1.1.28).

In certain embodiments, the cell includes one or more heterologous coding sequences for one or more enzymes or active fragments thereof that convert dopamine to 3,4-DHPA. In certain cases, the one or more enzymes is a monoamine oxidase (MAO) (e.g., EC 1.4.3.4). The one or more heterologous coding sequences may be derived from any convenient species (e.g., as described herein). In some cases, the one or more heterologous coding sequences may be derived from a species described in Table 1. In some cases, the one or more heterologous coding sequences are present in a gene or enzyme selected from those described in Table 1.

In some instances, the one or more heterologous coding sequences include a MAO coding sequence integrated at a genomic locus encoding native ARO10. In certain instances, the one or more heterologous coding sequences include a MAO coding sequence operably linked to an inducible promoter. In some embodiments, the inducible promoter is part of an inducible system including a DNA binding protein targeted to a promoter regulating the ARO10 gene. In some embodiments, the host cell includes one or more heterologous coding sequences for one or more enzymes or active fragments thereof described in the genes of Table 1.

As used herein, the term "heterologous coding sequences" also includes the coding portion of the peptide or enzyme, i.e., the cDNA or mRNA sequence, of the peptide or enzyme, as well as the coding portion of the full-length transcriptional unit, i.e., the gene including introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences may have a deletion of one or more amino acids, with the deletion being N-terminal, C-terminal, or internal. Truncated forms are envisioned as long as they have the catalytic capability indicated herein. Fusions of two or more enzymes are also envisioned to facilitate the transfer of metabolites in the pathway, provided that catalytic activities are maintained.

Operable fragments, mutants or truncated forms may be identified by modeling and/or screening. This is made possible by deletion of, for example, N-terminal, C-terminal, or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

Aspects of the present invention also relate to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of a decarboxylase, its catalytic activity. Equivalent sequences are also meant to include those which have been engineered and/or evolved to have properties different from the original amino acid sequence. Mutable properties of interest include catalytic activity, substrate specificity, selectivity, stability, solubility, localization, etc. In certain embodiments, an "equivalent" amino acid sequence contains at least 80%-99% identity at the amino acid level to the specific amino acid sequence, in some cases at least about 85%, 86%, 87%, 88%, 89%, 90%, 91%, 92%, 93%, 94% and more in certain cases, at least 95%, 96%, 97%, 98% and 99% identity, at the amino acid level. In some cases, the amino acid sequence may be identical but the DNA sequence is altered such as to optimize codon usage for the host organism, for example.

The host cells may also be modified to possess one or more genetic alterations to accommodate the heterologous coding sequences. Alterations of the native host genome include, but are not limited to, modifying the genome to reduce or ablate expression of a specific protein that may interfere with the desired pathway. The presence of such native proteins may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product.

In some instances, where ablation of expression of a protein may be of interest, the alteration is in proteins involved in the pleiotropic drug response, including, but not limited to, ATP-binding cassette (ABC) transporters, multi-drug resistance (MDR) pumps, and associated transcription factors. These proteins are involved in the export of BIA molecules into the culture medium, thus deletion controls the export of the compounds into the media, making them more available for incorporation into the desired product. In some embodiments, host cell gene deletions of interest include genes associated with the unfolded protein response and endoplasmic reticulum (ER) proliferation. Such gene deletions may lead to improved BIA production. The expression of cytochrome P450s may induce the unfolded protein response and may cause the ER to proliferate. Deletion of genes associated with these stress responses may control or reduce overall burden on the host cell and improve pathway performance. Genetic alterations may also include modifying the promoters of endogenous genes to increase expression and/or introducing additional copies of endogenous genes. Examples of this include the construction/use of strains which overexpress the endogenous yeast NADPH-P450 reductase CPR1 to increase activity of heterologous P450 enzymes. In addition, endogenous enzymes such as ARO8, 9, and 10, which are directly involved in the synthesis of intermediate metabolites, may also be overexpressed.

Heterologous coding sequences of interest include but are not limited to sequences that encode enzymes, either wild-type or equivalent sequences, that are normally responsible for the production of BIAs and precursors in plants. In some cases, the enzymes for which the heterologous sequences code may be any of the enzymes in the BIA pathway, and may be from any convenient source. The choice and number of enzymes encoded by the heterologous coding sequences for the particular synthetic pathway may be selected based upon the desired product. In certain embodiments, the host cells of the present invention may include 1 or more, 2 or more, 3 or more, 4 or more, 5 or more, 6 or more, 7 or more, 8 or more, 9 or more, 10 or more, 11 or more, 12 or more, 13 or more, 14 or more, or even 15 or more heterologous coding sequences, such as 1, 2, 3, 4, 5, 6, 7, 8, 9, 10, 11, 12, 13, 14, or 15 heterologous coding sequences.

In some cases, polypeptide sequences encoded by the heterologous coding sequences are as reported in GEN-BANK. Enzymes of interest include, but are not limited to, those enzymes described herein and those shown in Table 1. The host cells may include any combination of the listed enzymes, from any source. Unless otherwise indicated, accession numbers in Table 1 refer to GenBank. Some accession numbers refer to the *Saccharomyces* genome database (SGD), which is available on the world-wide web at www.yeastgenome.org.

In some embodiments, the host cell (e.g., a yeast strain) is engineered for selective production of a BIA of interest by localizing one or more enzymes to a compartment in the cell. In some cases, an enzyme may be located in the host cell such that the compound produced by this enzyme spontaneously rearranges, or is converted by another enzyme to a desirable metabolite before reaching a localized enzyme that may convert the compound into an undesirable metabolite. The spatial distance between two enzymes may be selected to prevent one of the enzymes from acting directly on a compound to make an undesirable metabolite, and restrict production of undesirable end products (e.g., an undesirable opioid by-product). In certain embodiments, any of the enzymes described herein, either singularly or together with a second enzyme, may be localized to any convenient compartment in the host cell, including but not limited to, an organelle, endoplasmic reticulum, golgi, vacuole, nucleus, plasma membrane, or the periplasm. In some embodiments, the host cell includes one or more of the enzymes that include a localization tag. Any convenient tags may be utilized. In some cases, the localization tag is a peptidic sequence that is attached at the N-terminal and/or C-terminal of the enzyme.

Any convenient methods may be utilized for attaching a tag to the enzyme. In some cases, the localization tag is derived from an endogenous yeast protein. Such tags may provide a route to a variety of yeast organelles including, but not limited to, the endoplasmic reticulum (ER), mitochondria (MT), plasma membrane (PM), and vacuole (V). In certain embodiments, the tag is an ER routing tag (e.g., ER1). In certain embodiments, the tag is a vacuole tag (e.g., V1). In certain embodiments, the tag is a plasma membrane tag (e.g., P1). In certain instances, the tag includes or is derived from, a transmembrane domain from within the tail-anchored class of proteins. In some embodiments, the localization tag locates the enzyme on the outside of an organelle. In certain embodiments, the localization tag locates the enzyme on the inside of an organelle.

In some instances, the expression of each type of enzyme is increased through additional gene copies (i.e., multiple copies), which increases intermediate accumulation and/or BIA of interest production. Embodiments of the present invention include increased BIA of interest production in a host cell through simultaneous expression of multiple species variants of a single or multiple enzymes. In some cases, additional gene copies of a single or multiple enzymes are included in the host cell. Any convenient methods may be utilized including multiple copies of a heterologous coding sequence for an enzyme in the host cell.

In some embodiments, the host cell includes multiple copies of a heterologous coding sequence for an enzyme, such as 2 or more, 3 or more, 4 or more, 5 or more, or even 10 or more copies. In certain embodiments, the host cell includes multiple copies of heterologous coding sequences for one or more enzymes, such as multiple copies of two or more, three or more, four or more, etc. In some cases, the multiple copies of the heterologous coding sequence for an enzyme are derived from two or more different source organisms as compared to the host cell. For example, the host cell may include multiple copies of one heterologous coding sequence, where each of the copies is derived from a different source organism. As such, each copy may include some variations in explicit sequences based on inter-species differences of the enzyme of interest that is encoded by the heterologous coding sequence.

In some embodiments of the host cell, the heterologous coding sequence is from a source organism selected from the group consisting of *P. somniferum*, *T. flavum*, and *C. japonica*. In some instances, the source organism is *P. somniferum*, *E. californica*, *C. japonica*, *T. flavum*, *Berberis stolonifer*, *T. flavum* subsp. *glaucum*, *Coptis chinensis*, *Thalictrum* spp, *Coptis* spp, *Papaver* spp, *Berberis wilsonae*, *A. mexicana*, or *Berberis* spp. In certain instances, the heterologous coding sequence is from a source organism selected from *P. somniferum*, *T. flavum*, and *C. japonica*. In some embodiments, the host cell includes a heterologous coding sequence from one or more of the source organisms described in Table 1.

The engineered host cell medium may be sampled and monitored for the production of BIAs of interest. The BIAs of interest may be observed and measured using any convenient methods. Methods of interest include, but are not limited to, LC-MS methods (e.g., as described herein) where a sample of interest is analyzed by comparison with a known amount of a standard compound. Identity may be confirmed, e.g., by m/z and MS/MS fragmentation patterns, and quantitation or measurement of the compound may be achieved via LC trace peaks of know retention time and/or EIC MS peak analysis by reference to corresponding LC-MS analysis of a known amount of a standard of the compound.

Methods
Process Steps

As summarized above, aspects of the invention include methods of preparing a benzylisoquinoline alkaloid (BIA) of interest. As such, aspects of the invention include culturing a host cell under conditions in which the one or more host cell modifications (e.g., as described herein) are functionally expressed such that the cell converts starting compounds of interest into product BIAs of interest or precursors thereof (e.g., pre-reticuline BIAs). Also provided are methods that include culturing a host cell under conditions suitable for protein production such that one or more heterologous coding sequences are functionally expressed and convert starting compounds of interest into product BIAs of interest. In some instances, the method is a method of preparing a benzylisoquinoline alkaloid (BIA), include culturing a host cell (e.g., as described herein); adding a starting compound to the cell culture; and recovering the BIA from the cell culture. In some embodiments of the method, the starting compound, BIA product and host cell are described by one of the entries of Table 1.

Fermentation media may contain suitable carbon substrates. The source of carbon suitable to perform the methods of this disclosure may encompass a wide variety of carbon containing substrates. Suitable substrates may include, without limitation, monosaccharides (e.g., glucose, fructose, galactose, xylose), oligosaccharides (e.g., lactose, sucrose, raffinose), polysaccharides (e.g., starch, cellulose), or a combination thereof. In some cases, unpurified mixtures from renewable feedstocks may be used (e.g., cornsteep liquor, sugar beet molasses, barley malt). In some cases, the carbon substrate may be a one-carbon substrate (e.g., methanol, carbon dioxide) or a two-carbon substrate (e.g., ethanol). In other cases, other carbon containing compounds may be utilized, for example, methylamine, glucosamine, and amino acids.

Any convenient methods of culturing host cells may be employed for producing the BIA precursors and downstream BIAs of interest. The particular protocol that is employed may vary, e.g., depending on host cell, the heterologous coding sequences, the desired BIA precursors and downstream BIAs of interest, etc. The cells may be present in any convenient environment, such as an environment in which the cells are capable of expressing one or more functional heterologous enzymes. In vitro, as used herein, simply means outside of a living cell, regardless of the location of the cell. As used herein, the term in vivo indicates inside a living cell, regardless of the location of the cell. In some embodiments, the cells are cultured under conditions that are conducive to enzyme expression and with appropriate substrates available to allow production of BIA precursors and downstream BIAs of interest in vivo. In some embodiments, the functional enzymes are extracted from the host for production of BIAs under in vitro conditions. In some instances, the host cells are placed back into a multicellular host organism. The host cells are in any phase of growth, including, but not limited to, stationary phase and log-growth phase, etc. In addition, the cultures themselves may be continuous cultures or they may be batch cultures.

Cells may be grown in an appropriate fermentation medium at a temperature between 20-40° C. Cells may be grown with shaking at any convenient speed (e.g., 200 rpm). Cells may be grown at a suitable pH. Suitable pH ranges for the fermentation may be between pH 5-9. Fermentations may be performed under aerobic, anaerobic, or microaerobic conditions. Any suitable growth medium may be used. Suitable growth media may include, without limitation, common commercially prepared media such as synthetic defined (SD) minimal media or yeast extract peptone dextrose (YEPD) rich media. Any other rich, defined, or synthetic growth media appropriate to the microorganism may be used.

Cells may be cultured in a vessel of essentially any size and shape. Examples of vessels suitable to perform the methods of this disclosure may include, without limitation, multi-well shake plates, test tubes, flasks (baffled and non-baffled), and bioreactors. The volume of the culture may range from 10 microliters to greater than 10,000 liters.

The addition of agents to the growth media that are known to modulate metabolism in a manner desirable for the production of alkaloids may be included. In a non-limiting example, cyclic adenosine 2'3'-monophosphate may be added to the growth media to modulate catabolite repression.

Any convenient cell culture conditions for a particular cell type may be utilized. In certain embodiments, the host cells that include one or more modifications are cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids are grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include, but are not limited to, sucrose, raffinose, and galactose. Cells are grown at any convenient temperature (e.g., 30° C.) with shaking at any convenient rate (e.g., 200 rpm) in a vessel, e.g., in test tubes or flasks in volumes ranging from 1-1000 mL, or larger, in the laboratory.

Culture volumes may be scaled up for growth in larger fermentation vessels, for example, as part of an industrial process. The industrial fermentation process may be carried out under closed-batch, fed-batch, or continuous chemostat conditions, or any suitable mode of fermentation. In some cases, the cells may be immobilized on a substrate as whole cell catalysts and subjected to fermentation conditions for alkaloid production.

A batch fermentation is a closed system, in which the composition of the medium is set at the beginning of the fermentation and not altered during the fermentation process. The desired organism(s) are inoculated into the medium at the beginning of the fermentation. In some instances, the batch fermentation is run with alterations made to the system to control factors such as pH and oxygen concentration (but not carbon). In this type of fermentation system, the biomass and metabolite compositions of the system change continuously over the course of the fermentation. Cells typically proceed through a lag phase, then to a log phase (high growth rate), then to a stationary phase (growth rate reduced or halted), and eventually to a death phase (if left untreated).

A fed-batch fermentation is similar to a batch fermentation, except that the substrate is added in intervals to the system over the course of the fermentation process. Fed-batch systems are used to reduce the impact of catabolite repression on the metabolism of the host cells and under other circumstances where it is desired to have limited amounts of substrate in the growth media.

A continuous fermentation is an open system, in which a defined fermentation medium is added continuously to the bioreactor and an equal amount of fermentation media is continuously removed from the vessel for processing. Continuous fermentation systems are generally operated to maintain steady state growth conditions, such that cell loss due to medium being removed must be balanced by the growth rate in the fermentation. Continuous fermentations are generally operated at conditions where cells are at a constant high cell density. Continuous fermentations allow for the modulation of one or more factors that affect target product concentration and/or cell growth.

The liquid medium may include, but is not limited to, a rich or synthetic defined medium having an additive component described above. Media components may be dissolved in water and sterilized by heat, pressure, filtration, radiation, chemicals, or any combination thereof. Several media components may be prepared separately and sterilized, and then combined in the fermentation vessel. The culture medium may be buffered to aid in maintaining a constant pH throughout the fermentation.

Process parameters including temperature, dissolved oxygen, pH, stirring, aeration rate, and cell density may be monitored or controlled over the course of the fermentation. For example, temperature of a fermentation process may be monitored by a temperature probe immersed in the culture medium. The culture temperature may be controlled at the set point by regulating the jacket temperature. Water may be cooled in an external chiller and then flowed into the bioreactor control tower and circulated to the jacket at the temperature required to maintain the set point temperature in the vessel.

Additionally, a gas flow parameter may be monitored in a fermentation process. For example, gases may be flowed into the medium through a sparger. Gases suitable for the methods of this disclosure may include compressed air, oxygen, and nitrogen. Gas flow may be at a fixed rate or regulated to maintain a dissolved oxygen set point.

The pH of a culture medium may also be monitored. In examples, the pH may be monitored by a pH probe that is immersed in the culture medium inside the vessel. If pH control is in effect, the pH may be adjusted by acid and base pumps which add each solution to the medium at the required rate. The acid solutions used to control pH may be sulfuric acid or hydrochloric acid. The base solutions used to control pH may be sodium hydroxide, potassium hydroxide, or ammonium hydroxide.

Further, dissolved oxygen may be monitored in a culture medium by a dissolved oxygen probe immersed in the culture medium. If dissolved oxygen regulation is in effect, the oxygen level may be adjusted by increasing or decreasing the stirring speed. The dissolved oxygen level may also be adjusted by increasing or decreasing the gas flow rate. The gas may be compressed air, oxygen, or nitrogen.

Stir speed may also be monitored in a fermentation process. In examples, the stirrer motor may drive an agitator. The stirrer speed may be set at a consistent rpm throughout the fermentation or may be regulated dynamically to maintain a set dissolved oxygen level.

Additionally, turbidity may be monitored in a fermentation process. In examples, cell density may be measured using a turbidity probe. Alternatively, cell density may be measured by taking samples from the bioreactor and analyzing them in a spectrophotometer. Further, samples may be removed from the bioreactor at time intervals through a sterile sampling apparatus. The samples may be analyzed for alkaloids produced by the host cells. The samples may also be analyzed for other metabolites and sugars, the depletion of culture medium components, or the density of cells.

In another example, a feed stock parameter may be monitored during a fermentation process. In particular, feed stocks including sugars and other carbon sources, nutrients, and cofactors that may be added into the fermentation using an external pump. Other components may also be added during the fermentation including, without limitation, antifoam, salts, chelating agents, surfactants, and organic liquids.

Any convenient codon optimization techniques for optimizing the expression of heterologous polynucleotides in host cells may be adapted for use in the subject host cells and methods, see e.g., Gustafsson, C. et al. (2004) *Trends Biotechnol*, 22, 346-353, which is incorporated by reference in its entirety.

The subject method may also include adding a starting compound to the cell culture. Any convenient methods of addition may be adapted for use in the subject methods. The cell culture may be supplemented with a sufficient amount of the starting materials of interest (e.g., as described herein), e.g., a mM to µM amount such as between about 1-5 mM of a starting compound. It is understood that the amount of starting material added, the timing and rate of addition, the form of material added, etc., may vary according to a variety of factors. The starting material may be added neat or pre-dissolved in a suitable solvent (e.g., cell culture media, water, or an organic solvent). The starting material may be added in concentrated form (e.g., 10× over desired concentration) to minimize dilution of the cell culture medium upon addition. The starting material may be added in one or more batches, or by continuous addition over an extended period of time (e.g., hours or days).

Methods for Isolating Products from the Fermentation Medium

The subject methods may also include recovering the BIA of interest from the cell culture. Any convenient methods of separation and isolation (e.g., chromatography methods or precipitation methods) may be adapted for use in the subject methods to recover the BIA of interest from the cell culture. Filtration methods may be used to separate soluble from insoluble fractions of the cell culture. In some cases, liquid chromatography methods (e.g., reverse phase HPLC, size exclusion, normal phase chromatography) may be used to separate the BIA of interest from other soluble components of the cell culture. In some cases, extraction methods (e.g., liquid extraction, pH based purification, etc.) may be used to separate the BIA of interest from other components of the cell culture.

The produced alkaloids may be isolated from the fermentation medium using methods known in the art. A number of recovery steps may be performed immediately after (or in some instances, during) the fermentation for initial recovery of the desired product. Through these steps, the alkaloids (e.g., BIAs) may be separated from the cells, cellular debris and waste, and other nutrients, sugars, and organic molecules may remain in the spent culture medium. This process may be used to yield a BIA-enriched product.

In an example, a product stream having a benzylisoquinoline alkaloid (BIA) product is formed by providing engineered yeast cells and a feedstock including nutrients and water to a batch reactor. The engineered yeast cells may have at least one modification selected from the group consisting of: a feedback inhibition alleviating mutation in a biosynthetic enzyme gene native to the cell; a transcriptional modulation modification of a biosynthetic enzyme gene native to the cell; and an inactivating mutation in an enzyme native to the cell. When the engineered yeast cells are within the batch reactor, the engineered yeast cells may be subjected to fermentation. In particular, the engineered yeast cells may be subjected to fermentation by incubating the engineered yeast cells for a time period of at least about 5 minutes to produce a solution comprising the BIA product and cellular material. Once the engineered yeast cells have been subjected to fermentation, at least one separation unit may be used to separate the BIA product from the cellular material to provide the product stream comprising the BIA product. In particular, the product stream may include the BIA product as well as additional components, such as a clarified yeast culture medium. Additionally, a BIA product may comprise one or more BIAs of interest, such as one or more BIA compounds.

Different methods may be used to remove cells from a bioreactor medium that include a BIA of interest. In examples, cells may be removed by sedimentation over time. This process of sedimentation may be accelerated by chilling or by the addition of fining agents such as silica. The spent culture medium may then be siphoned from the top of the reactor or the cells may be decanted from the base of the reactor. Alternatively, cells may be removed by filtration through a filter, a membrane, or other porous material. Cells may also be removed by centrifugation, for example, by continuous flow centrifugation or by using a continuous extractor.

If some valuable BIAs of interest are present inside the cells, the cells may be permeabilized or lysed and the cell debris may be removed by any of the methods described above. Agents used to permeabilize the cells may include, without limitation, organic solvents (e.g., DMSO) or salts (e.g., lithium acetate). Methods to lyse the cells may include the addition of surfactants such as sodium dodecyl sulfate, or mechanical disruption by bead milling or sonication.

BIAs of interest may be extracted from the clarified spent culture medium through liquid-liquid extraction by the addition of an organic liquid that is immiscible with the aqueous culture medium. Examples of suitable organic liquids include, but are not limited to, isopropyl myristate, ethyl acetate, chloroform, butyl acetate, methylisobutyl ketone, methyl oleate, toluene, oleyl alcohol, ethyl butyrate. The organic liquid may be added to as little as 10% or as much as 100% of the volume of aqueous medium.

In some cases, the organic liquid may be added at the start of the fermentation or at any time during the fermentation. This process of extractive fermentation may increase the yield of BIAs of interest from the host cells by continuously removing BIA precursors or BIAs to the organic phase.

Agitation may cause the organic phase to form an emulsion with the aqueous culture medium. Methods to encourage the separation of the two phases into distinct layers may include, without limitation, the addition of a demulsifier or a nucleating agent, or an adjustment of the pH. The emulsion may also be centrifuged to separate the two phases, for example, by continuous conical plate centrifugation.

Alternatively, the organic phase may be isolated from the aqueous culture medium so that it may be physically removed after extraction. For example, the solvent may be encapsulated in a membrane.

In examples, BIAs of interest may be extracted from a fermentation medium using adsorption methods. In particular, BIAs of interest may be extracted from clarified spent culture medium by the addition of a resin such as Amberlite® XAD4 or another agent that removes BIAs by adsorption. The BIAs of interest may then be released from the resin using an organic solvent. Examples of suitable organic solvents include, but are not limited to, methanol, ethanol, ethyl acetate, or acetone.

BIAs of interest may also be extracted from a fermentation medium using filtration. At high pH, the BIAs of interest may form a crystalline-like precipitate in the bioreactor. This precipitate may be removed directly by filtration through a filter, membrane, or other porous material. The precipitate may also be collected by centrifugation and/or decantation.

The extraction methods described above may be carried out either in situ (in the bioreactor) or ex situ (e.g., in an external loop through which media flows out of the bioreactor and contacts the extraction agent, then is recirculated back into the vessel). Alternatively, the extraction methods may be performed after the fermentation is terminated using the clarified medium removed from the bioreactor vessel.

Methods for Purifying Products from Alkaloid-Enriched Solutions

Subsequent purification steps may involve treating the post-fermentation BIA precursor- or BIA-enriched product using methods known in the art to recover individual product species of interest to high purity.

In one example, BIA precursors or BIAs extracted in an organic phase may be transferred to an aqueous solution. In some cases, the organic solvent may be evaporated by heat and/or vacuum, and the resulting powder may be dissolved in an aqueous solution of suitable pH. In a further example, the BIA precursors or BIAs may be extracted from the organic phase by addition of an aqueous solution at a suitable pH that promotes extraction of the BIA precursors or BIAs into the aqueous phase. The aqueous phase may then be removed by decantation, centrifugation, or another method.

The BIA precursor- or BIA-containing solution may be further treated to remove metals, for example, by treating with a suitable chelating agent. The BIA precursor- or BIA-containing solution may be further treated to remove other impurities, such as proteins and DNA, by precipitation. In one example, the BIA precursor- or BIA-containing solution is treated with an appropriate precipitation agent such as ethanol, methanol, acetone, or isopropanol. In an alternative example, DNA and protein may be removed by dialysis or by other methods of size exclusion that separate the smaller alkaloids from contaminating biological macromolecules.

In further examples, the BIA precursor-, BIA-, or modified BIA-containing solution may be extracted to high purity by continuous cross-flow filtration using methods known in the art.

If the solution contains a mixture of BIA precursors or BIAs, it may be subjected to acid-base treatment to yield individual BIA of interest species using methods known in the art. In this process, the pH of the aqueous solution is adjusted to precipitate individual BIA precursors or BIAs at their respective pKas.

For high purity, small-scale preparations, the BIA precursors or BIAs may be purified in a single step by liquid chromatography.

Yeast-Derived Alkaloid APIs Versus Plant-Derived APIs

The clarified yeast culture medium (CYCM) may contain a plurality of impurities. The clarified yeast culture medium may be dehydrated by vacuum and/or heat to yield an alkaloid-rich powder. This product is analogous to the concentrate of poppy straw (CPS) or opium, which is exported from poppy-growing countries and purchased by API manufacturers. For the purposes of this invention, CPS is a representative example of any type of purified plant extract from which the desired alkaloids product(s) may ultimately be further purified. Tables 2 and 3 highlight the impurities in these two products that may be specific to either CYCM or CPS or may be present in both. By analyzing a product of unknown origin for a subset of these impurities, a person of skill in the art could determine whether the product originated from a yeast or plant production host.

API-grade pharmaceutical ingredients are highly purified molecules. As such, impurities that could indicate the plant- or yeast-origin of an API (such as those listed in Tables 2 and 3) may not be present at that API stage of the product. Indeed, many of the API products derived from yeast strains of the present invention may be largely indistinguishable from the traditional plant-derived APIs. In some cases, however, conventional alkaloid compounds may be subjected to chemical modification using chemical synthesis approaches which may show up as chemical impurities in plant-based products that require such chemical modifications. For example, chemical derivatization may often result in a set of impurities related to the chemical synthesis processes. In certain situations, these modifications may be performed biologically in the yeast production platform, thereby avoiding some of the impurities associated with chemical derivation from being present in the yeast-derived product. In particular, these impurities from the chemical derivation product may be present in an API product that is produced using chemical synthesis processes but may be absent from an API product that is produced using a yeast-derived product. Alternatively, if a yeast-derived product is mixed with a chemically derived product, the resulting impurities may be present but in a lesser amount than would be expected in an API that only or primarily contains chemically derived products. In this example, by analyzing the API product for a subset of these impurities, a person of skill in the art could determine whether the product originated from a yeast production host or the traditional chemical derivatization route.

Non-limiting examples of impurities that may be present in chemically-derivatized morphinan APIs but not in biosynthesized APIs include a codeine-O(6)-methyl ether impurity in API codeine; 8,14-dihydroxy-7,8-dihydrocodeinone in API oxycodone; and tetrahydrothebaine in API hydrocodone. The codeine-O(6)-methyl ether may be formed by chemical over-methylation of morphine. The 8,14-dihydroxy-7,8-dihydrocodeinone in API oxycodone may be formed by chemical over-oxidation of thebaine. Additionally, the tetrahydrothebaine in API hydrocodone may be formed by chemical over-reduction of thebaine.

However, in the case where the yeast-derived compound and the plant-derived compound are both subjected to chemical modification through chemical synthesis approaches, the same impurities associated with the chemical synthesis process may be expected in the products. In such a situation, the starting material (e.g., CYCM or CPS) may be analyzed as described above.

Methods of Engineering Host Cells

Also included are methods of engineering host cells for the purpose of producing BIAs of interest or precursors thereof. Inserting DNA into host cells may be achieved using any convenient methods. The methods are used to insert the heterologous coding sequences into the host cells such that the host cells functionally express the enzymes and convert starting compounds of interest into product BIAs of interest.

Any convenient promoters may be utilized in the subject host cells and methods. The promoters driving expression of the heterologous coding sequences may be constitutive promoters or inducible promoters, provided that the promoters are active in the host cells. The heterologous coding sequences may be expressed from their native promoters, or non-native promoters may be used. Such promoters may be low to high strength in the host in which they are used. Promoters may be regulated or constitutive. In certain embodiments, promoters that are not glucose repressed, or repressed only mildly by the presence of glucose in the culture medium, are used. Promoters of interest include but are not limited to, promoters of glycolytic genes such as the promoter of the B. subtilis tsr gene (encoding the promoter region of the fructose bisphosphate aldolase gene) or the promoter from yeast S. cerevisiae gene coding for glyceraldehyde 3-phosphate dehydrogenase (GPD, GAPDH, or TDH3), the ADH1 promoter of baker's yeast, the phosphate-starvation induced promoters such as the PHO5 promoter of yeast, the alkaline phosphatase promoter from B. licheniformis, yeast inducible promoters such as Gal1-10, Gal1, GalL, GalS, repressible promoter Met25, tetO, and constitutive promoters such as glyceraldehyde 3-phosphate dehydrogenase promoter (GPD), alcohol dehydrogenase promoter (ADH), translation-elongation factor-1-α promoter (TEF), cytochrome c-oxidase promoter (CYC1), MRP7 promoter, etc. Autonomously replicating yeast expression vectors containing promoters inducible by hormones such as glucocorticoids, steroids, and thyroid hormones may also be used and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as a factor, alcohol oxidase, and PGH may be used. Additionally any promoter/enhancer combination (as per the Eukaryotic Promoter Data Base EPDB) could also be used to drive expression of genes. Any convenient appropriate promoters may be selected for the host cell, e.g., E. coli. One may also use promoter selection to optimize transcript, and hence, enzyme levels to maximize production while minimizing energy resources.

Any convenient vectors may be utilized in the subject host cells and methods. Vectors of interest include vectors for use in yeast and other cells. The types of yeast vectors may be broken up into 4 general categories: integrative vectors (YIp), autonomously replicating high copy-number vectors (YEp or 2μ plasmids), autonomously replicating low copy-number vectors (YCp or centromeric plasmids) and vectors for cloning large fragments (YACs). Vector DNA is introduced into prokaryotic or eukaryotic cells via any convenient transformation or transfection techniques.

Utility

The host cells and methods of the invention, e.g., as described above, find use in a variety of applications. Applications of interest include, but are not limited to: research applications and therapeutic applications. Methods of the invention find use in a variety of different applications including any convenient application where the production of BIAs is of interest.

The subject host cells and methods find use in a variety of therapeutic applications. Therapeutic applications of interest include those applications in which the preparation of pharmaceutical products that include BIAs is of interest. The host cells described herein produce benzylisoquinoline alkaloid precursors (BIA precursors) and BIAs of interest. Reticuline is a major branch point intermediate of interest in the synthesis of BIAs including engineering efforts to produce end products such as opioid products. The subject host cells may be utilized to produce BIA precursors from simple and inexpensive starting materials that may find use in the production of BIAs of interest, including reticuline, and BIA end products. As such, the subject host cells find use in the supply of therapeutically active BIAs or precursors thereof.

In some instances, the host cells and methods find use in the production of commercial scale amounts of BIAs or precursors thereof where chemical synthesis of these compounds is low yielding and not a viable means for large-scale production. In certain cases, the host cells and methods are utilized in a fermentation facility that would include bioreactors (fermenters) of e.g., 5,000-200,000 liter capacity allowing for rapid production of BIAs of interest or precursors thereof for therapeutic products. Such applications may include the industrial-scale production of BIAs of interest from fermentable carbon sources such as cellulose, starch, and free sugars.

The subject host cells and methods find use in a variety of research applications. The subject host cells and methods may be used to analyze the effects of a variety of enzymes on the biosynthetic pathways of a variety of BIAs of interest or precursors thereof. In addition, the host cells may be engineered to produce BIAs or precursors thereof that find use in testing for bioactivity of interest in as yet unproven therapeutic functions. In some cases, the engineering of host cells to include a variety of heterologous coding sequences that encode for a variety of enzymes elucidates the high yielding biosynthetic pathways towards BIAs of interest or precursors thereof. In certain cases, research applications include the production of precursors for therapeutic molecules of interest that may then be further chemically modified or derivatized to desired products or for screening for increased therapeutic activities of interest. In some instances, host cell strains are used to screen for enzyme activities that are of interest in such pathways, which may lead to enzyme discovery via conversion of BIA metabolites produced in these strains.

The subject host cells and methods may be used as a production platform for plant specialized metabolites. The subject host cells and methods may be used as a platform for drug library development as well as plant enzyme discovery. For example, the subject host cells and methods may find use in the development of natural product based drug libraries by taking yeast strains producing interesting scaffold molecules, such as protopine, and further functionalizing the compound structure through combinatorial biosynthesis or by chemical means. By producing drug libraries in this way, any potential drug hits are already associated with a production host that is amenable to large-scale culture and production. As another example, these subject host cells and methods may find use in plant enzyme discovery. The subject host cells provide a clean background of defined metabolites to express plant EST libraries to identify new enzyme activities. The subject host cells and methods provide expression methods and culture conditions for the functional expression and increased activity of plant enzymes in yeast.

Kits and Systems

Aspects of the invention further include kits and systems, where the kits and systems may include one or more components employed in methods of the invention, e.g., host cells, starting compounds, heterologous coding sequences, vectors, culture medium, etc., as described herein. In some embodiments, the subject kit includes a host cell (e.g., as described herein), and one or more components selected from the following: starting compounds, a heterologous coding sequence and/or a vector including the same, vectors, growth feedstock, components suitable for use in expression systems (e.g., cells, cloning vectors, multiple cloning sites (MCS), bi-directional promoters, an internal ribosome entry site (IRES), etc.), and a culture medium.

Any of the components described herein may be provided in the kits, e.g., host cells including one or more modifications, starting compounds, culture medium, etc. A variety of components suitable for use in making and using heterologous coding sequences, cloning vectors and expression systems may find use in the subject kits. Kits may also include tubes, buffers, etc., and instructions for use. The various reagent components of the kits may be present in separate containers, or some or all of them may be pre-combined into a reagent mixture in a single container, as desired.

Also provided are systems for producing a BIA of interest, where the systems may include engineered host cells including one or more modifications (e.g., as described herein), starting compounds, culture medium, a fermenter and fermentation equipment, e.g., an apparatus suitable for maintaining growth conditions for the host cells, sampling and monitoring equipment and components, and the like. A variety of components suitable for use in large scale fermentation of yeast cells may find use in the subject systems.

In some cases, the system includes components for the large scale fermentation of engineered host cells, and the monitoring and purification of BIA compounds produced by the fermented host cells. In certain embodiments, one or more starting compounds (e.g., as described herein) are added to the system, under conditions by which the engineered host cells in the fermenter produce one or more desired BIA products or precursors thereof. In some instances, the host cells produce a BIA of interest (e.g., as described herein). In certain cases, the BIA products of interest are opioid products, such as codeine, neopine, morphine, neomorphine, hydrocodone, oxycodone, hydromorphone, dihydrocodeine, 14-hydroxycodeine, or dihydromorphine.

In some cases, the system includes means for monitoring and or analyzing one or more BIA compounds or precursors thereof produced by the subject host cells. For example, a LC-MS analysis system as described herein, a chromatography system, or any convenient system where the sample may be analyzed and compared to a standard, e.g., as described herein. The fermentation medium may be monitored at any convenient times before and during fermentation by sampling and analysis. When the conversion of starting compounds to BIA products or precursors of interest is complete, the fermentation may be halted and purification of the BIA products may be done. As such, in some cases, the subject system includes a purification component suitable for purifying the BIA products or precursors of interest from the host cell medium into which it is produced. The purification component may include any convenient means that may be used to purify the BIA products or precursors of fermentation, including but not limited to, silica chromatography, reverse-phase chromatography, ion exchange chromatography, HIC chromatography, size exclusion chromatography, liquid extraction, and pH extraction methods. In some cases, the subject system provides for the production and isolation of BIA fermentation products of interest following the input of one or more starting compounds to the system.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example I

A series of specific genetic modifications provide a biosynthetic process in *Saccharomyces cerevisiae* for the production of BIAs from simple, inexpensive feedstocks or precursor molecules. Methods for constructing novel strains capable of producing the early BIA molecules norcoclaurine (NC) and norlaudanosoline (NL) from non-BIA precursors or simple feedstocks are described. NC has never been reported as a product of microbial synthesis and is the natural precursor to all known BIA molecules. Methods for manipulating the regulation of yeast biosynthetic pathways and for optimizing the production of aromatic amino acids and related BIA precursors are also described.

A. Tyrosine and Related BIA Precursor Overproducing Yeast Strains

Strains of *S. cerevisiae* are developed with improved flux through the aromatic amino acid biosynthesis pathway for the purposes of increasing intracellular concentrations of BIA precursor molecules including tyrosine, 4-hydroxyphenylacetaldehyde (4-HPA), L-3,4-dihydroxyphenylalanine (L-DOPA), 3,4-dihydroxyphenylacetaldehyde (3,4-DHPA), and dopamine. These strains combine genetic modifications to the yeast strain for the purpose of increasing carbon flux from central metabolism towards aromatic amino acid synthesis in general, towards tyrosine in particular, and include the introduction of key heterologous enzymes for the production of BIA precursor molecules not naturally produced by yeast. Genetic modifications are employed including the introduction of feedback inhibition alleviating mutations to genes encoding native biosynthetic enzymes, tuning of transcriptional regulation of native biosynthetic enzymes, deletion of genes encoding enzymes that divert precursor molecules away from the intended pathway, and introduction of heterologous enzymes for the conversion of naturally endogenous molecules into non-native BIA precursor molecules.

Specific Description:

1.1) The biosynthetic pathway in the engineered strain incorporates feedback inhibition alleviating mutations (1.1.1) to the native yeast gene ARO4, which encodes a 3-deoxy-d-arabinose-heptulosonate-7-phosphate (DAHP) synthase, alone or in combination. This mutation (ARO4$^{FBR}$) is incorporated as a directed mutation to the native gene at the original locus, as an additional copy introduced as a genetic integration at a separate locus, or as an additional copy on an episomal vector such as a 2µ or centromeric plasmid. FBR refers to feedback resistant mutants and mutations. The feedback inhibited copy of the DAHP synthase enzyme is under the native yeast transcriptional regulation or is introduced with engineered constitutive or dynamic regulation of protein expression by placing it under the control of a synthetic promoter.

1.1.1) ARO4$^{FBR}$ mutations may include, for example, a substitution of the lysine residue at position 229 with a leucine (see e.g., Hartmann M, et al. (2003) Evolution of feedback-inhibited beta/alpha barrel isoenzymes by gene duplication and a single mutation. *Proc Natl Acad Sci USA* 100(3):862-867), a substitution of the glutamine residue at position 166 with a lysine residue (see e.g., Fukuda K et al. (1992) Feedback-Insensitive Mutation of 3-Deoxy-D-Arabino-Hepturosonate-7-Phosphate Synthase Caused by a Single Nucleotide Substitution of Aro4 Structural Gene in *Saccharomyces-Cerevisiae*. *J Ferment Bioeng* 74(2):117-119), or an additional mutation conferring feedback inhibition selected from a mutagenized library of microbial DHAP synthase mutants. Examples of such selections include rescue of growth on o-fluoro-D,L-phenylalanine (see e.g., Fukuda et al. (1990) Breeding of Brewing Yeast Producing a Large Amount of Beta-Phenylethyl Alcohol and Beta-Phenylethyl Acetate. Agr Biol Chem Tokyo 54(1):269-271) or growth of aro3 mutant yeast strains on media with excess tyrosine.

1.2) The biosynthetic pathway in the engineered strain incorporates a feedback inhibition alleviating mutation (1.2.1) to the native yeast gene ARO7, which encodes the enzyme chorismate mutase. This mutation (ARO7$^{FBR}$) is incorporated as a directed mutation to the native gene at the original locus, as an additional copy introduced as a genetic integration at a separate locus, or as an additional copy on an episomal vector such as a 2µ or centromeric plasmid. The feedback inhibited copy of the chorismate mutase enzyme is under the native yeast transcriptional regulation or is introduced with engineered constitutive or dynamic regulation of protein expression by placing it under the control of a synthetic promoter.

1.2.1) ARO7$^{FBR}$ mutant alleles may include, for example, a substitution of the threonine residue at position 226 with an isoleucine (see e.g., Schmidheini et al. (1989) A Single Point Mutation Results in a Constitutively Activated and Feedback-Resistant Chorismate Mutase of *Saccharomyces-Cerevisiae*. J Bacteriol 171(3):1245-1253) or an additional mutation conferring feedback inhibition selected from a mutagenized library of microbial chorismate mutase mutants. Examples of such selections include assays for 5-methyltryptophan sensitivity or increased production of melanin pigments in strains expressing heterologous tyrosinase enzymes (1.9) in the absence of externally fed tyrosine.

1.3) The biosynthetic pathway in the engineered strain incorporates the introduction of a strong promoter element (such as GPD1, TEF1, etc) for the overexpression of the native yeast gene ARO10, which encodes an enzyme with hydroxyphenylpyruvate decarboxylase activity. This genetic modification is incorporated as a directed swapping of the native promoter DNA sequence at the original locus, as an additional copy of the gene under new transcriptional regulation introduced as a genetic integration at a separate locus, or as an additional copy on an episomal vector such as a 2µ or centromeric plasmid.

1.4) The biosynthetic pathway in the engineered strain incorporates the introduction of a strong promoter element (such as GPD1, TEF1, etc) for the overexpression of the native yeast gene ARO9, which encodes an enzyme with hydroxyphenylpyruvate/glutamic acid transaminase activity. This genetic modification is incorporated as a directed swapping of the native promoter DNA sequence at the original locus, as an additional copy of the gene under new transcriptional regulation introduced as a genetic integration at a separate locus, or as an additional copy on an episomal vector such as a 2µ or centromeric plasmid.

1.5) The biosynthetic pathway in the engineered strain incorporates the introduction of a strong promoter element (such as GPD1, TEF1, etc) for the overexpression of the native yeast gene TKL, which encodes an enzyme with transketolase activity. This genetic modification is incorporated as a directed swapping of the native promoter DNA sequence at the original locus, as an additional copy of the gene under new transcriptional regulation introduced as a genetic integration at a separate locus, or as an additional copy on an episomal vector such as a 2µ or centromeric plasmid.

1.6) The biosynthetic pathway in the engineered strain is improved by the incorporation of a deletion or inactivating mutation of the native yeast gene ZWF1, which encodes an enzyme with glucose-6-phosphate dehydrogenase activity.

1.7) The biosynthetic pathway in the engineered strain is improved by the incorporation of one or more deletion(s) or inactivating mutation(s) of known native alcohol dehydrogenase enzymes, such as the enzymes encoded by the genes ADH2, ADH3, ADH4, ADH5, ADH6, ADH7, or SFA1.

1.8) The biosynthetic pathway in the engineered strain is improved by the incorporation of one or more deletion(s) or inactivating mutation(s) of known native aldehyde oxidoreductases, such as ALD2, ALD3, ALD4, ALD5, or ALD6.

1.9) The biosynthetic pathway incorporates a heterologous enzyme for the conversion of tyrosine to L-DOPA. This enzyme may be from one of several classes, including, but not limited to bacterial tyrosinases, eukaryotic tyrosinases, and tyrosine hydroxylases (Table 1). The gene for this enzyme is incorporated as a genetic integration or on an episomal vector such as a 2µ or centromeric plasmid. This L-DOPA producing enzyme is introduced with engineered constitutive or dynamic regulation of protein expression by placing it under the control of a synthetic promoter.

1.9.1) In a biosynthetic pathway using a tyrosine hydroxylase enzyme for the conversion of tyrosine to L-DOPA, additional expression of genes encoding enzymes for the synthesis and recycling of the pterin cofactor tetrahydrobiopterin (BH4) and its derivatives are incorporated into the engineered strain in support of the activity of the tyrosine hydroxylase enzyme. These enzymes include GTP cyclohydrolase, 6-pyruvoyl-tetrahydropterin synthase, sepiapterin reductase, 4a-hydroxytetrahydrobiopterin dehydratase, and quinoid dihydropteridine reductase (Table 1). The genes for these enzymes are incorporated as a genetic integration or on an episomal vector such as a 2µ or centromeric plasmid. These BH4 synthesis and recycling enzymes are introduced with engineered constitutive or dynamic regulation of protein expression by placing it under the control of a synthetic promoter.

1.10) The biosynthetic pathway incorporates a heterologous enzyme for the decarboxylation of L-DOPA to produce dopamine. Enzymes with this activity are encoded by a genes from a variety of organisms including bacteria, plants, and mammals. Examples include *Pseudomonas putida* DOPA decarboxylase (PpDODC), *Rattus norvegicus* DOPA decarboxylase (RnDODC), and *Papaver somniferum* tyrosine/DOPA decarboxylase (PsTYDC) (Table 1). The gene for this enzyme is incorporated as a genetic integration or on an episomal vector such as a 2µ or centromeric plasmid. This dopamine producing enzyme is introduced with engineered constitutive or dynamic regulation of protein expression by placing it under the control of a synthetic promoter.

1.11) A biosynthetic pathway for the production of 3,4-DHPA incorporates a heterologous enzyme for the oxidation of dopamine to 3,4-DHPA. Examples of genes encoding this enzyme that may be used in the strain include human monoamine oxidase A (hMAOA), *E. coli* monoamine oxidase (EcMAO), and *Micrococcus luteus* monoamine oxidase (MIMAO) (Table 1). The gene for this enzyme is incorporated as a genetic integration or on an episomal vector such as a 2µ or centromeric plasmid. This 3,4-DHPA producing enzyme is introduced with engineered constitutive or dynamic regulation of protein expression by placing it under the control of a synthetic promoter.

1.11.1) Strains for the production of NC require dopamine and 4-HPA, while strains for the production of NL require dopamine and 3,4-DHPA, but not 4-HPA. A specific modification for the conversion of an NC producing strain into an NL producing strain is the integration of a MAO gene into the yeast genome at the locus encoding the native yeast gene ARO10. This combines a deletion of the native yeast enzyme responsible for converting a tyrosine biosynthetic precursor to 4-HPA with the introduction of the enzyme capable of converting dopamine to 3,4-DHPA.

1.11.2) Yeast strains are constructed with a gene that expresses a MAO enzyme (1.11) under the control of an inducible promoter. When the strain is grown in the presence of the inducer it may catalyze the conversion of dopamine to 3,4-DHPA, in the absence of inducer the strain only produces 4-HPA.

1.11.2.1) Yeast strains are constructed with inducible MAO expression (1.11.2), where the inducible system also contains a DNA binding protein targeted to the promoter regulating the ARO10 gene (1.3). The synthetic promoter controlling ARO10 is therefore repressed when the promoter controlling the MAO gene is activated and ARO10 is only expressed when the MAO gene is not transcriptionally active. This system allows for the construction of a single strain that conditionally only produces the precursors for NC or NL.

B. NC-Producing Yeast Strains

Methods are developed to produce the BIA molecule NC in yeast and demonstrate a first system for microbial synthesis of NC. With the engineered strains described herein, NC is produced and accumulated for its own value or combined with a biosynthetic pathway of additional heterologous enzymes for the complete synthesis of downstream BIAs.

Specific Description:

2.1) Yeast strains are grown in liquid culture to a high cell concentration before back diluting to intermediate concentrations (as measured by optical density or OD) in defined media containing high concentrations of dopamine. The media components only need to satisfy conditions for growth of the strains; various growth feedstocks are used (for example, different sugars, nitrogen sources). The NC produced by these yeast strains is excreted by the yeast cells and is measurable in the spent media. Additional NC retained by cells is recovered via cell lysis and extraction from the lysate.

2.2) Yeast strains containing various combinations of the modifications as described in (1.1-1.8) substantially improve NC production from that measurable in unmodified strains in fed dopamine assays as described above (2.1). In conditions where no extracellular tyrosine is available in the yeast media, modifications described (1.1-1.8) provide for production of NC from fed dopamine; under these conditions the NC production from unmodified yeast strains is most often undetectable.

2.3) Yeast strains that produce NC when containing the modification as described in (1.10) and grown as described in (2.1) when the additional BIA precursor added to media is L-DOPA instead of dopamine.

2.3.1) Yeast strains as described in (2.3) containing various combinations of the modifications as described in (1.1-1.8) substantially improve production of NC.

2.4) Yeast strains that produce NC when containing both the heterologous enzymes for conversion of tyrosine to dopamine (1.9, 1.10) alongside various combinations of modifications described above (1.1-1.8) and grown in media without supplementation of tyrosine, L-DOPA, or dopamine. This specific example constitutes complete synthesis of NC by the strain from simple carbon and nitrogen sources.

2.5) Yeast strains are modified and cultured as described above (2.1-2.4) where the biosynthetic pathway includes the incorporation of the heterologous enzyme NCS, or truncated versions of the NCS enzyme, for the stereospecific catalysis of the reaction condensing dopamine and 4-HPA for S-NC production. This enzyme may originate from one of several plants, such as *Papaver somniferum, Coptis japonica*, and *Thalicitum flavum* (Table 1). The gene for this enzyme is incorporated as a genetic integration or on an episomal vector such as a 2μ or centromeric plasmid. This S-NC producing enzyme is introduced with engineered constitutive or dynamic regulation of protein expression by placing it under the control of a synthetic promoter. The NC ultimately produced will be an enantiomeric mixture with bias towards the S-stereoisomer.

2.6) Yeast strains are modified and cultured as described above (2.1-2.5) where the biosynthetic pathway includes the incorporation of the heterologous enzyme norcoclaurine 6-O-methyltransferase (6OMT) for the catalysis of the reaction producing coclaurine. 6OMT may originate from one of several plants, such as *Papaver somniferum, Coptis japonica*, and *Thalicitum flavum* (Table 1).

2.7) Yeast strains are modified and cultured as described above (2.1-2.5) where the biosynthetic pathway includes the incorporation of the heterologous enzymes 6OMT and coclaurine N-methyltransferase (CNMT) for the catalysis of the reactions producing coclaurine and N-methylcoclaurine. CNMT may originate from one of several plants, such as *Papaver somniferum, Coptis japonica*, and *Thalicitum flavum* (Table 1).

2.8) Yeast strains are modified and cultured as described above (2.1-2.5) where the biosynthetic pathway includes the incorporation of the heterologous enzymes 6OMT, CNMT, CYP80B1, and cytochrome P450 reductase (CPR) for the catalysis of the reactions producing coclaurine, N-methylcoclaurine, and 3'hydroxy-N-methyl-coclaurine. CYP80B1 may originate from one of several plants, such as *Papaver somniferum* or *Eschscholzia californica* (Table 1).

2.9) Yeast strains are modified and cultured as described above (2.1-2.5) where the biosynthetic pathway includes the incorporation of the heterologous enzymes 6OMT, CNMT, CYP80B1, CPR, and 3'hydroxy-N-methylcoclaurine 4'-O-methyltransferase (4'OMT) for the catalysis of the reactions producing coclaurine, N-methylcoclaurine, 3'hydroxy-N-methyl-coclaurine, and reticuline. 4'OMT may originate from one of several plants, such as *Papaver somniferum, Coptis japonica*, and *Thalicitum flavum* (Table 1).

C. NL-Producing Yeast Strains

Methods are developed to produce the BIA molecule NL from yeast. With the engineered strains described herein, NL is produced and accumulated for its own value or combined with a biosynthetic pathway of further heterologous enzymes for the complete synthesis of downstream BIAs.

Specific Description:

3.1) Yeast strains containing modifications as described in (1.11, 1.11.1-1.11.2, 1.11.2.1) are grown in liquid culture as described in (2.1) produce NL.

3.2) Yeast strains containing various combinations of gene deletions as described in (1.7,1.8) improve NL production from that measurable in unmodified strains in fed dopamine assays as described above (3.1).

3.3) Yeast strains that produce NL when containing the modifications as described in (1.10, 1.11,1.11.1-1.11.2, 1.11.2.1) and grown as described in (3.1) when the additional BIA precursor is added to media is L-DOPA instead of dopamine.

3.3.1) Yeast strains as described in (3.3) containing combinations of gene deletions described in (1.7,1.8) improve production of NL.

3.4) Yeast strains that produce NL when containing both the heterologous enzymes for conversion of tyrosine to dopamine (1.9, 1.10) and dopamine to 3,4-DHPA (1.11) alongside various combinations of modifications described above (1.1-1.8, 1.11.1) are grown in media without supplementation of tyrosine, L-DOPA, or dopamine. This specific example constitutes complete synthesis of NL by the strain from simple carbon and nitrogen sources.

3.5) Yeast strains modified and cultured as described above (3.1-3.4) where the biosynthetic pathway includes the incorporation of the heterologous enzyme NCS, or truncated versions of the NCS enzyme (Table 1), for the stereospecific catalysis of the reaction condensing dopamine and 3,4-DHPA for S-NL production. This enzyme may originate from one of several plants, such as *Papaver somniferum, Coptis japonica*, and *Thalicitum flavum* (Table 1). The gene for this enzyme is incorporated as a genetic integration or on an episomal vector such as a 2μ or centromeric plasmid. This S-NL producing enzyme is introduced with engineered constitutive or dynamic regulation of protein expression by placing it under the control of a synthetic promoter. The NC ultimately produced is an enantiomeric mixture with bias towards the S-stereoisomer.

3.6) Yeast strains are modified and cultured as described above (3.1-3.5) where the biosynthetic pathway includes the incorporation of the heterologous enzyme norcoclaurine 6-O-methyltransferase (6OMT) for the catalysis of the reaction producing 3'hydroxycoclaurine. 6OMT may originate from one of several plants, such as *Papaver somniferum, Coptis japonica*, and *Thalicitum flavum* (Table 1).

3.7) Yeast strains are modified and cultured as described above (3.1-3.5) where the biosynthetic pathway includes the incorporation of the heterologous enzyme coclaurine N-methyltransferase (CNMT) for the catalysis of the reaction producing laudanosoline. CNMT may originate from one of several plants, such as *Papaver somniferum, Coptis japonica*, and *Thalicitum flavum* (Table 1).

3.8) Yeast strains are modified and cultured as described above (3.1-3.5) where the biosynthetic pathway includes the incorporation of the heterologous enzymes 6OMT and CNMT for the catalysis of the reactions producing 3'hydroxycoclaurine, laudanosoline, and 3' hydroxyl-N-methyl-coclaurine.

3.9) Yeast strains are modified and cultured as described above (3.1-3.5) where the biosynthetic pathway includes the incorporation of the heterologous enzyme 3'hydroxy-N-methylcoclaurine 4'-O-methyltransferase (4'OMT) for the catalysis of the reaction producing 4'-O-methylnorlaudanosoline. 4'OMT may originate from one of several plants, such as *Papaver somniferum, Coptis japonica*, and *Thalicitum flavum* (Table 1).

3.10) Yeast strains are modified and cultured as described above (3.1-3.5) where the biosynthetic pathway includes the incorporation of the heterologous enzymes 6OMT and 4'OMT for the catalysis of the reactions producing 3'hydroxycoclaurine, 4'-O-methylnorlaudanosoline, and norreticuline.

3.11) Yeast strains are modified and cultured as described above (3.1-3.5) where the biosynthetic pathway includes the incorporation of the heterologous enzymes CNMT and 4'OMT for the catalysis of the reactions producing 4'-O-methylnorlaudanosoline, laudanosoline, and 4'-O-methyllaudanosoline.

3.12) Yeast strains are modified and cultured as described above (3.1-3.5) where the biosynthetic pathway includes the incorporation of the heterologous enzymes 6OMT, CNMT, and 4'OMT for the catalysis of the reactions producing 3'hydroxycoclaurine, laudanosoline, 4'-O-methylnorlaudanosoline, norreticuline, 3'hydroxy-N-methylcoclaurine, 4'-O-methyllaudanosoline, and reticuline.

Example 2

Processing Methods from Fermentation to Purification to API

During the final stages of the fermentation, the organic liquid ethyl acetate is added to the culture medium at 20% of the volume of the culture broth. At this time the pH of the culture medium may also be increased to support the extraction of BIAs into the organic ethyl acetate phase. The agitation from the stirrer and sparger causes the immiscible ethyl acetate to form an emulsion with the aqueous medium. At the completion of the fermentation the stirrer and sparger are switched off and the aqueous and organic phases are allowed to separate. A demulsifier or other chemical agent may be added to promote the separation into two distinct phases. The cells settle to the bottom of the reactor and form a third layer. The three layers are separated by decantation. The cell and aqueous culture medium phases are discarded. The BIA precursor- or BIA-containing organic phase is treated with heat and vacuum to remove the ethyl acetate. The resulting powder containing the BIA precursors or BIAs is dissolved in acidified water. The solution is purified by cross-flow filtration to yield a solution consisting only of morphinan alkaloids. The solution is then subjected to several rounds of acid-base extraction to remove individual morphinan alkaloids according to their distinct solubility at known pH values. Each precipitate of morphinan alkaloid (e.g., codeine sulfate) is removed by filtration and may be subject to further product polishing to yield an API-grade product.

Example 3

Processing Methods from Fermentation to Purification to API

The fermentation broth is centrifuged to remove cells and particulates. The remaining aqueous clarified culture medium is processed by a similar method used to extract BIAs from aqueous poppy straw extract in the kabay process (GB406,107). The clarified culture medium may be acidic due to the fermentation processes. If not, the medium is acidified by addition of sulfuric acid. The alkaloids are concentrated in the clarified culture medium by the application of a vacuum or heat. The solution is treated with ethanol to precipitate impurities including proteins and DNA. Further treatment involves several rounds of acid-base extraction and may include the addition of organic solvents to aid in extracting distinct BIA species into a second phase.

Example 4

Modification of Media to Improve BIA Production

Figure 17:
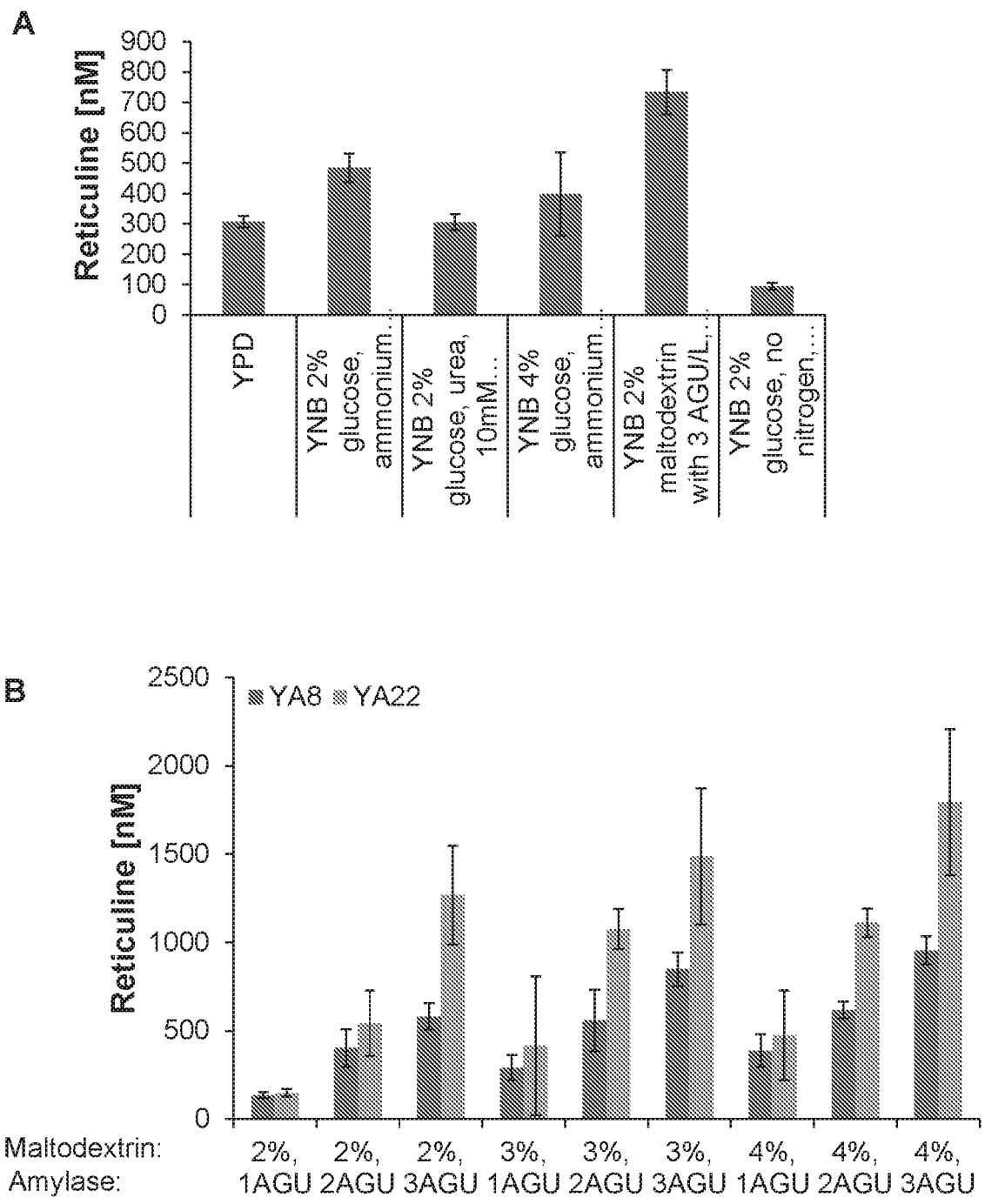
FIG. 17 shows the effect of (A) media composition and (B) maltodextrin and amylase concentrations on the production of reticuline from sugar in the liquid culture of engineered yeast strains.
Figure 18:
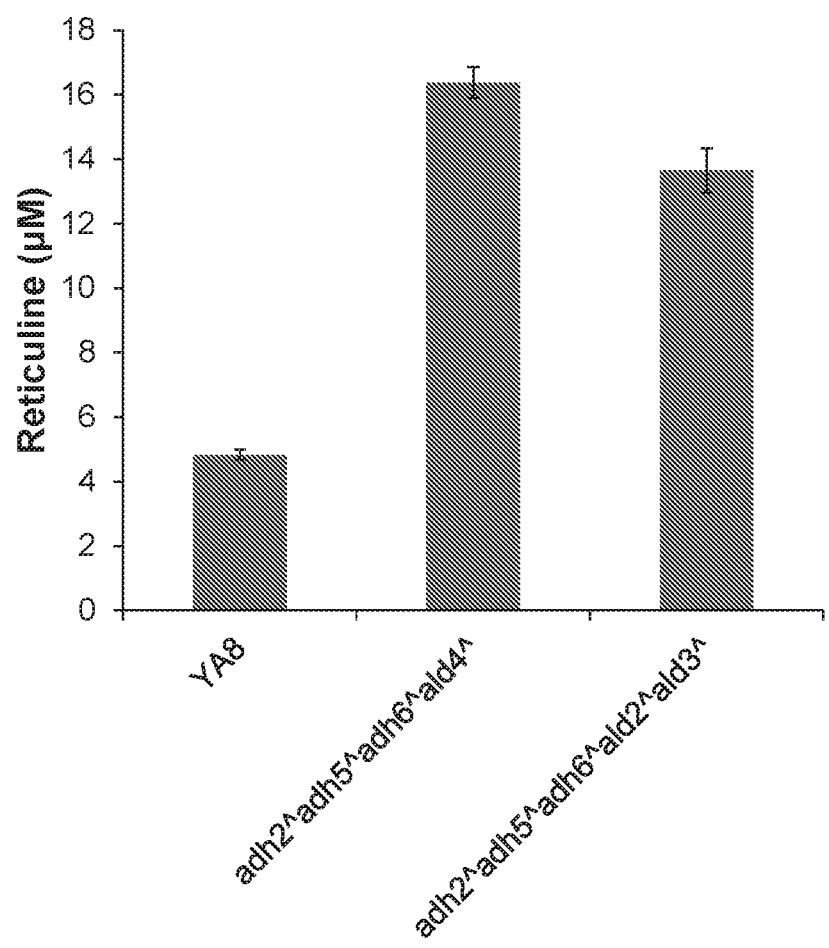
FIG. 18 shows the effect of inactivating mutations in ADH and ALD enzymes on the production of reticuline from sugar in the liquid culture of engineering yeast strains.

BIA production titers from engineered yeast strains were improved by modifying the culture media composition. For example, the media types can vary in the media base (e.g., yeast peptone, yeast nitrogen base), carbon source (e.g., glucose, maltodextrin), and nitrogen source (e.g., amino acids, ammonium sulfate, urea). Reticuline-producing yeast strains (as described in 2.9) were grown under varying media conditions and reticuline production assayed after 72 hours of growth at 30 C. The highest production of reticuline was observed in YNB, 2% maltodextrin with 3 AGU/L, ammonium sulfate, and all amino acids (FIG. 17A). Maltodextrin is a polymer of glucose that can be broken down by amylase. When maltodextrin is used as the carbon source in yeast culture medium, the addition of amylase creates a slow release of glucose, thereby mimicking fed-batch fermentation conditions. High concentration of amylase results in faster release of glucose and is effectively a faster glucose feed rate. In this example, the feed rate of glucose impacts product titers (FIG. 17B). The data demonstrate the highest titers of reticuline in media comprising 4% maltodextrin with 3 AGU/L.

FIG. 1: Biosynthesis of Tyrosine and BIA Precursor Molecules

Schematic showing the biosynthetic pathway from glucose to tyrosine and other BIA precursors. Aromatic amino acid intermediates present in native yeast metabolism are written in black. Endogenous yeast enzymes are written in grey (apart from TYR, TyrH, DODC, and MAO). Heterologous enzymes include TYR, TyrH, DODC, and MAO. As described in (1.1, 1.2) wild-type yeast enzymes encoded by ARO4 and ARO7 are allosterically inhibited by tyrosine, indicated here by the dotted grey line. Individual steps in the pentose phosphosphate pathway and glycolysis are not explicitly detailed in this figure, although the genes TKL1 and ZWF1 (targeted in 1.5, 1.6) are involved in the pentose phosphate pathway, as indicated.

FIG. 2: Effect of ZWF1 Knockout and TKL1 Over-Expression on Pentose Phosphate Pathway (PPP)

Schematic detailing how modifications to TKL1 (1.5) and ZWF1 (1.6) affect the overall carbon flow through the pentose phosphate pathway in yeast when glucose is the primary carbon source. Panel A represents wild-type carbon flow; Panel B represents the relative change in carbon flow in a modified strain.

FIG. 3A: Synthesis of NC from Precursor Molecules

NC is synthesized from one molecule of dopamine and one molecule of 4-HPA via a Pictet-Spengler condensation reaction. This reaction may occur spontaneously to produce a racemic mixture of R- and S-NC. This reaction may alternatively be catalyzed by the plant enzyme NCS, which produces S-NC.

FIG. 3B: Synthesis of NL from Precursor Molecules

NL is synthesized from one molecule of dopamine and one molecule of 3,4-DHPA via a Pictet-Spengler condensation reaction. This reaction may occur spontaneously to produce a racemic mixture of R- and S-NL. While the natural product of NCS is NC, the enzyme has been shown to catalyze the stereospecific production of S-NL (see e.g., Rueffer et al. (1981) (S)-Norlaudanosoline Synthase—the 1st Enzyme in the Benzylisoquinoline Biosynthetic-Pathway. Febs Lett 129(1):5-9).

Measurement of the BIA molecules is performed by LC-MS analysis, where NC production (m/z=+272, 19.2 min retention time) and NL production (m/z=+288, 18.9 min retention time) were observed, with ion MS2 fragmentation agreeing with both standards and published detection methods (see e.g., Schmidt et al. (2007) Poppy alkaloid profiling by electrospray tandem mass spectrometry and electrospray FT-ICR mass spectrometry after [ring-13C6]-tyramine feeding. Phytochemistry 68(2):189-202).

Figure 4:
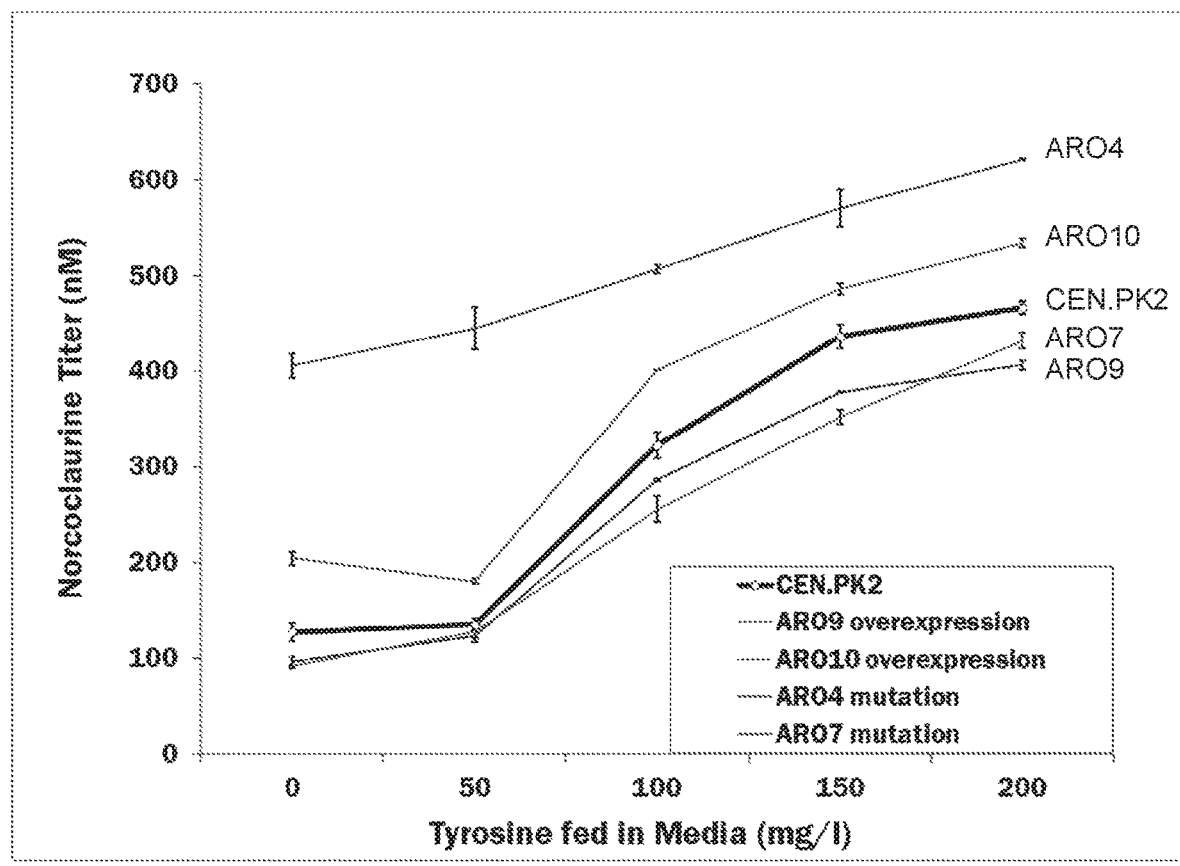
FIG. 4 illustrates the effect of four genetic modifications on NC production with varying fed tyrosine.

FIG. 4: Effect of Four Genetic Modifications on NC Production with Varying Fed Tyrosine NC production was demonstrated at several concentrations of fed tyrosine, including no fed tyrosine, in strains with targeted genetic modifications. Wild-type strain, CEN.PK2, was integrated with constructs conferring one of four genetic changes (as described in 1.1-1.4): overexpression of ARO10 by promoter replacement with $P_{TEF1}$, overexpression of ARO9 by promoter replacement with $P_{TEF1}$, chromosomal integration of an ARO4$^{FBR}$ allele, and chromosomal integration of an ARO7$^{FBR}$ allele. When incorporated alone, only the $P_{TEF1}$-ARO10 and ARO4$^{FBR}$ increase production of NC. While both these modifications increased NC production at all tyrosine concentrations, the ARO$^{FBR}$ integrated strain improved most drastically at zero fed tyrosine.

Figure 5:
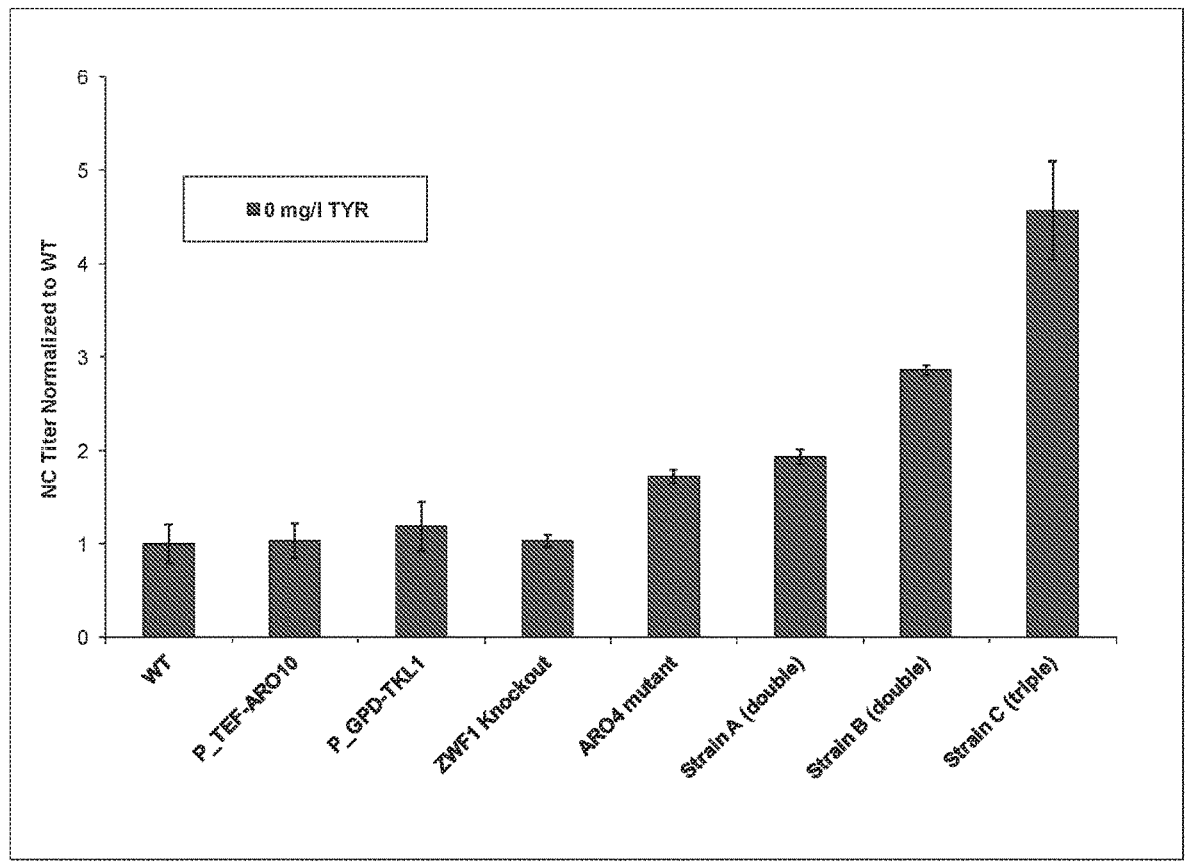
FIG. 5 shows NC production from strains with combinations of genetic modifications.

FIG. 5: NC Production with Combinations of Genetic Modifications

Some genetic modifications as described above (1.5, 1.6) improve NC production only in combination with the integration of the ARO4$^{FBR}$ mutant (1.1). This figure shows four strains engineered with single genetic modifications, $P_{TEF1}$-ARO10 (1.3), $P_{GPD}$-TKL1 (1.5), ZWF1 knockout (1.6), and ARO4$^{FBR}$ (1.1), alongside three strains constructed with combinations of genetic modifications: Strain A ($P_{GPD}$-TKL1, ARO4$^{FBR}$), Strain B (ZWF1 knockout, ARO4$^{FBR}$), and Strain C ($P_{GPD}$-TKL1, ZWF1 knockout, ARO4$^{FBR}$). NC production is shown normalized to the WT strain, with Strain C exhibiting a five-fold increase in NC production.

Figure 6:
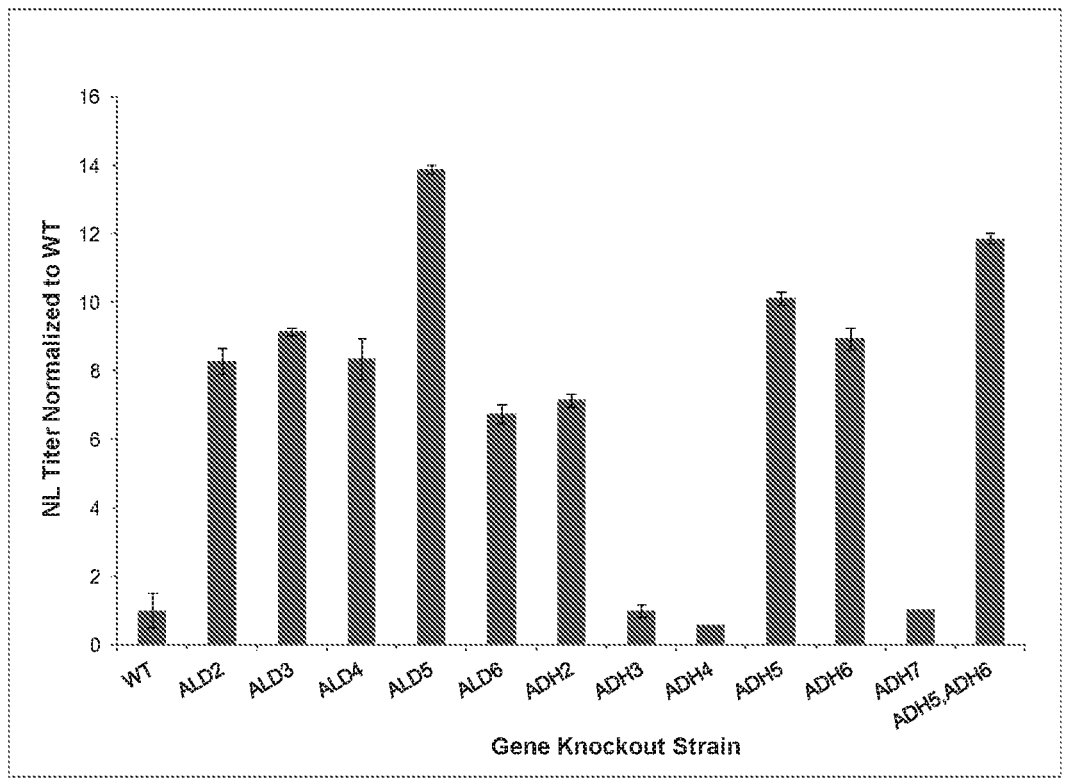
FIG. 6 shows the levels of NL production in aldehyde oxidoreductase (ALD)/alcohol dehydrogenase (ADH) gene knockout strains.

FIG. 6: NL Production in ALD/ADH Knockout Strains

NL production is improved by the deletion of competing yeast enzymes (1.7, 1.8) in a strain expressing human MAOA on a 2μ plasmid (1.11) and grown in media containing dopamine. NL production is shown as titer measured in spent media normalized to the WT (with hMAO, but with no deletions). Improvements in production are as much as ten times WT NL production.

Figure 7:
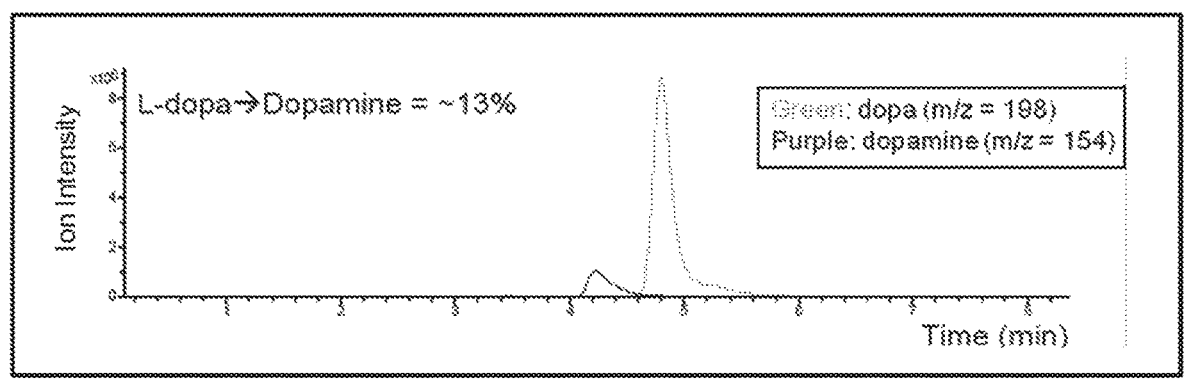
FIG. 7 illustrates the activity of a L-DOPA decarboxylase (DODC) enzyme in vivo. Yeast strains transformed with DNA to express *Papaver somniferum* tyrosine/DOPA decarboxylase may convert L-DOPA to dopamine in vivo.
Figure 8:
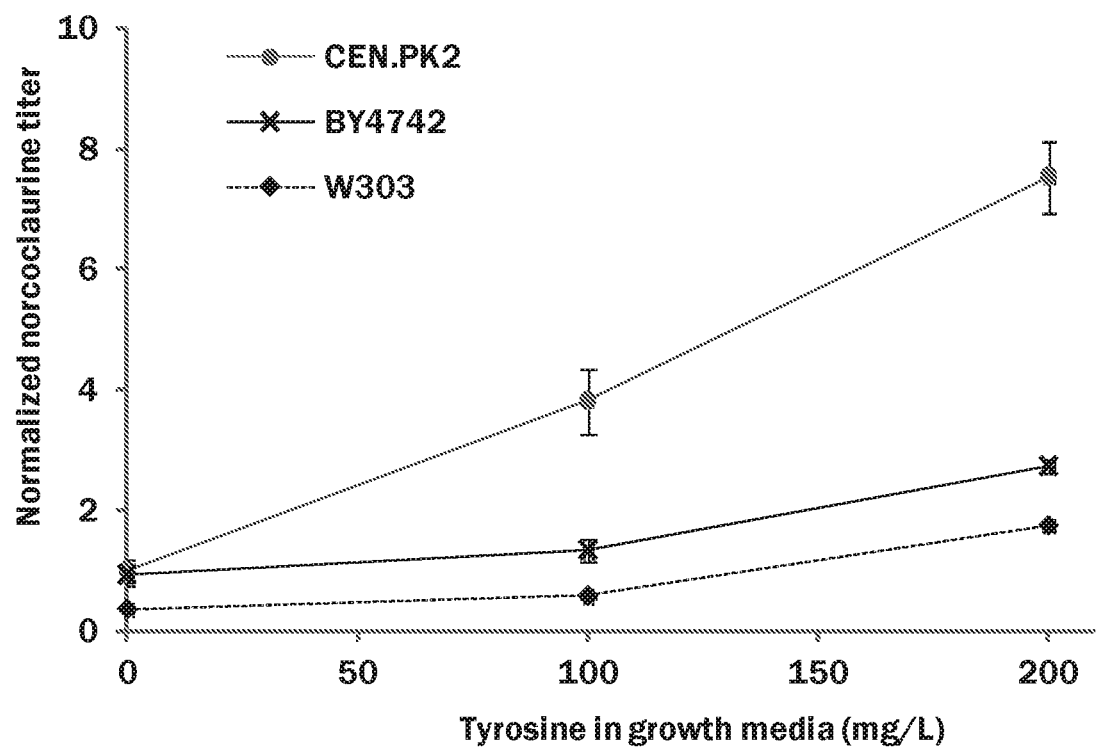
FIG. 8 shows the production of norcoclaurine (NC) in yeast strains fed 100 mM dopamine and varying concentrations of tyrosine.

FIG. 7: Activity of a DODC Enzyme In Vivo

Yeast strains transformed with DNA to express *Papaver somniferum* tyrosine/DOPA decarboxylase may convert L-DOPA to dopamine in vivo. Strains harboring a 2μ plasmid were grown in selective media and then back-diluted into media containing L-DOPA. Spent media was then measured for concentrations of L-DOPA (retention time 4.8 min, m/z=+198) and dopamine (retention time 4.2 min, m/z=+154).

FIG. 8

NC is produced as described in (2.1) in multiple wild-type yeast lab strains at varying tyrosine concentrations. Specifically, each yeast strain is inoculated into separate liquid cultures and grown overnight to $OD_{600}$~10, then back-diluted in YNB minimal media without tyrosine to an $OD_{600}$~1 and grown for 3 hours. 100 μl of each culture was mixed into 400 μl YNB media containing 100 mM dopamine and varying concentrations of tyrosine; each strain was grown in each media condition in triplicate samples. NC titer was measured from culture supernatant on an LC-MS instrument detecting m/z+272 ion count in peaks as described by (see e.g., Schmidt et al. (2007) Poppy alkaloid profiling by electrospray tandem mass spectrometry and electrospray FT-ICR mass spectrometry after [ring-13C6]-tyramine feeding. Phytochemistry 68(2):189-202). The area of each peak was integrated to calculate a relative quantity of the NC in each sample and the results were normalized to the ion count area in CEN.PK2 yeast culture with 0 mg/L tyrosine.

FIG. 9

NC is produced as described in (2.1) in multiple engineered yeast strains at fed 100 mM dopamine and no tyrosine. These data were generated in a separate experiment from those in FIG. 5. The strains CSY1031-1044 were engineered to contain combinations of the genetic modifications described in (1.1-1.6); the labels underneath each strain name indicate which modifications were incorporated into each strain. Strain CSY1043 contains four genetic modifications to yeast native metabolism and exhibits the largest increase in NC titer above the wild-type yeast strain CEN.PK2.

FIG. 10

NC production as described in (2.1) for black diamonds and as described in (2.3) for gray circles. Here NC was produced in an engineered yeast strain (CSY1042) with the additional integration of the L-DOPA decarboxylase PpDODC (1.10). In separate liquid cultures this yeast strain was grown in YNB minimal media containing varying concentrations of dopamine (black diamonds) and YNB minimal media containing L-DOPA (gray circles; cultures not fed dopamine). The solid black line represents a linear regression of the relationship between the measured NC and fed dopamine. The peak area measurements for the L-DOPA fed samples were plotted along the regression line for dopamine fed samples to show an "equivalent fed dopamine" quantity for the cultures fed L-DOPA. L-DOPA media was mixed to achieve a target concentration of 10 mM L-DOPA, however L-DOPA was not fully soluble at that concentration, and the effective concentration of dissolved L-DOPA is estimated to be approximately 6 mM. Based on the average NC titers of the two L-DOPA fed yeast cultures the "equivalent fed dopamine" concentration is approximately 50 mM or 8× the fed L-DOPA concentration (indicated by the gray dotted lines).

FIG. 11

Mammalian tyrosine hydroxylases (TyrHs) are capable of hydroxylating tyrosine, but are dependent on the co-substrate tetrahydrobiopterin (BH4) for activity, as described in (1.9.1). During the catalysis of tyrosine to L-DOPA by TyrH, molecular oxygen is split and transferred to tyrosine and BH4, as shown by reaction 1. BH4 is oxidized to BH4-4α-carbinolamine (4αOH-BH4). Two heterologous enzymes are expressed in yeast to synthesize BH4 from the folate synthesis pathway intermediate, dihydroneopterin triphosphate. First, 6-pyruvoyltetrahydropterin synthase (PTPS) converts dihydroneopterin to PTP (reaction 2), which is then reduced to BH4 by sepiapterin reductase (SepR, reaction 3). Two enzymes are responsible for the regeneration of BH4 from its 4α-carbinolamine form. First, pterin-4a-carbinolamine dehydratase (PCD) catalyzes a loss of water reaction to form dihydrobioterin (reaction 4). Dihydrobiopterin is then reduced to tetrahydrobiopterin by quinoid dihydropteridine reductase (QDHPR, reaction 5).

FIG. 12

Tyrosine hydroxylases expressed from yeast cells convert tyrosine to L-DOPA. Yeast strains transformed with plasmids carrying tyrosine hydroxylases from human (hTH2) and rat (RnTyrH) were grown in liquid media and then lysed in buffer containing tyrosine and the co-substrate BH4. After 6-hour incubations at 30° C., L-DOPA was measured in the lysate mixture by LC-MS. (A) LC-MS chromatogram confirms conversion of tyrosine to L-DOPA dependent on the presence of the co-substrate, BH4. (B) Fragmentation of the +198 m/z ion peak further confirms the presence of L-DOPA in lysate samples. (See e.g., Lv et al. (2010) LC-MS-MS Simultaneous Determination of L-Dopa and its prodrug n-Pentyl Hydrochloride in Rat Plasma. *Chromatographia*, 72(3/4), 239-243).

FIG. 13

Co-expression of tyrosine hydroxylase with a BH4 biosynthetic enzyme enables conversion of tyrosine to L-DOPA in yeast cell lysates. Engineered yeast strains integrated with constructs expressing rat tyrosine hydroxylase (RnTyrH) and rat sepiapterin reductase (RnSepR) were grown in liquid media and then lysed in buffer containing tyrosine, NADPH, and the BH4 biosynthetic precursor, sepiapterin. Co-expression of a TyrH with the BH4 biosynthesis gene provides for activity of the tyrosine hydroxylase in the absence of BH4, but in the presence of the BH4 precursor, sepiapterin.

FIG. 14

Biosynthetic pathways for the synthesis of BIA precursors and pre-reticuline BIAs from tyrosine through to reticuline. (A) Biosynthetic pathway from tyrosine to reticuline that goes through NC. (B) Biosynthetic pathway from tyrosine to reticuline that goes through NL (depiction includes various methylated intermediates that can be produced). * Note that although TyrH is depicted as catalyzing the conversion of L-tyrosine to L-DOPA, other enzymes including tyrosinases can be used to perform this step as described in the specification.

FIG. 15

Figure 9:
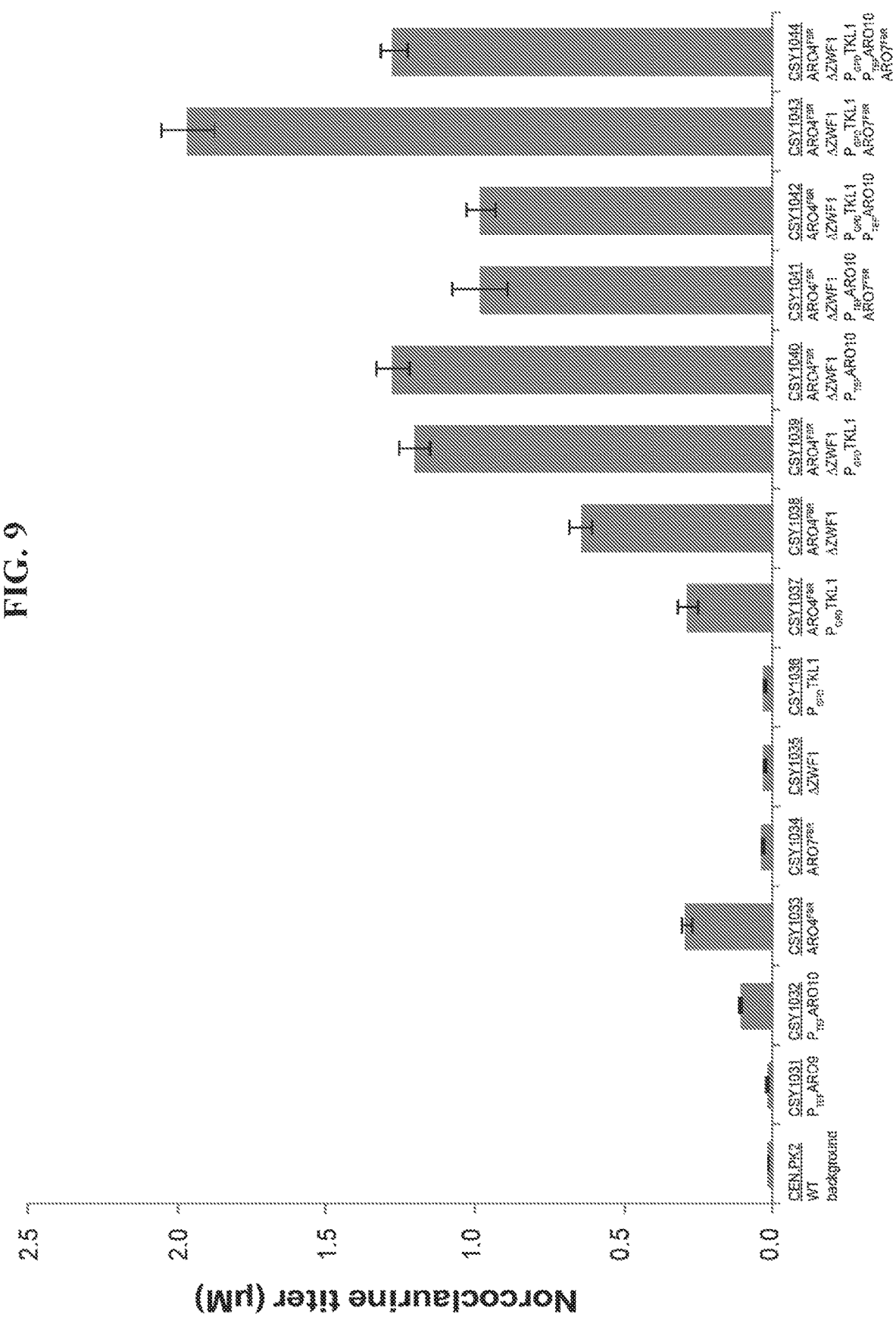
FIG. 9 shows NC production in multiple engineered yeast strains fed 100 mM dopamine and no tyrosine.
Figure 10:
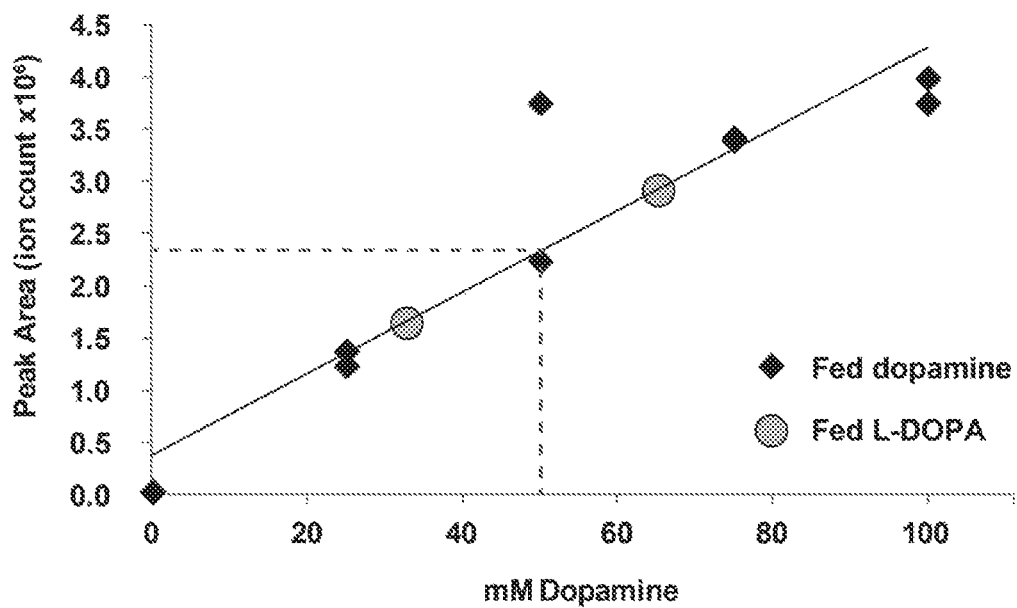
FIG. 10 shows NC production from dopamine or from L-DOPA in an engineered yeast strain (CSY980) with the additional integration of the L-DOPA decarboxylase PpDODC.
Figure 11:
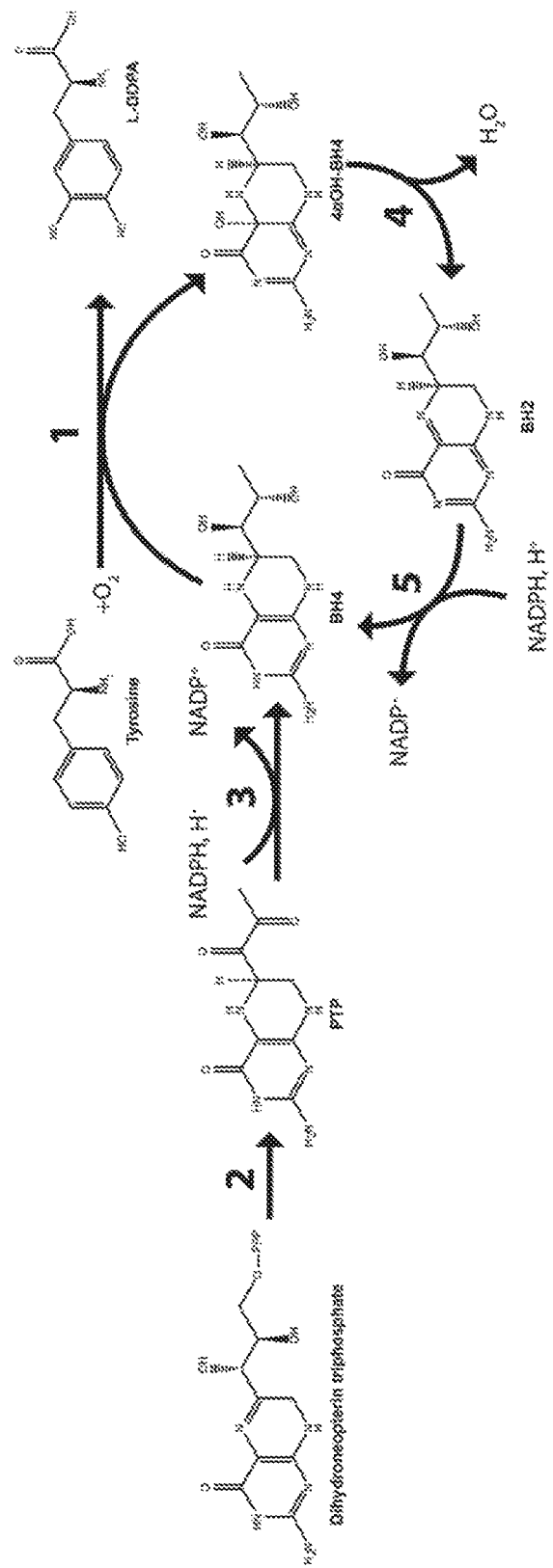
FIG. 11 illustrates a biosynthetic scheme including tyrosine hydroxylation using mammalian tyrosine hydroxylases (TyrHs) with the co-substrate tetrahydrobiopterin (BH4).
Figure 12:
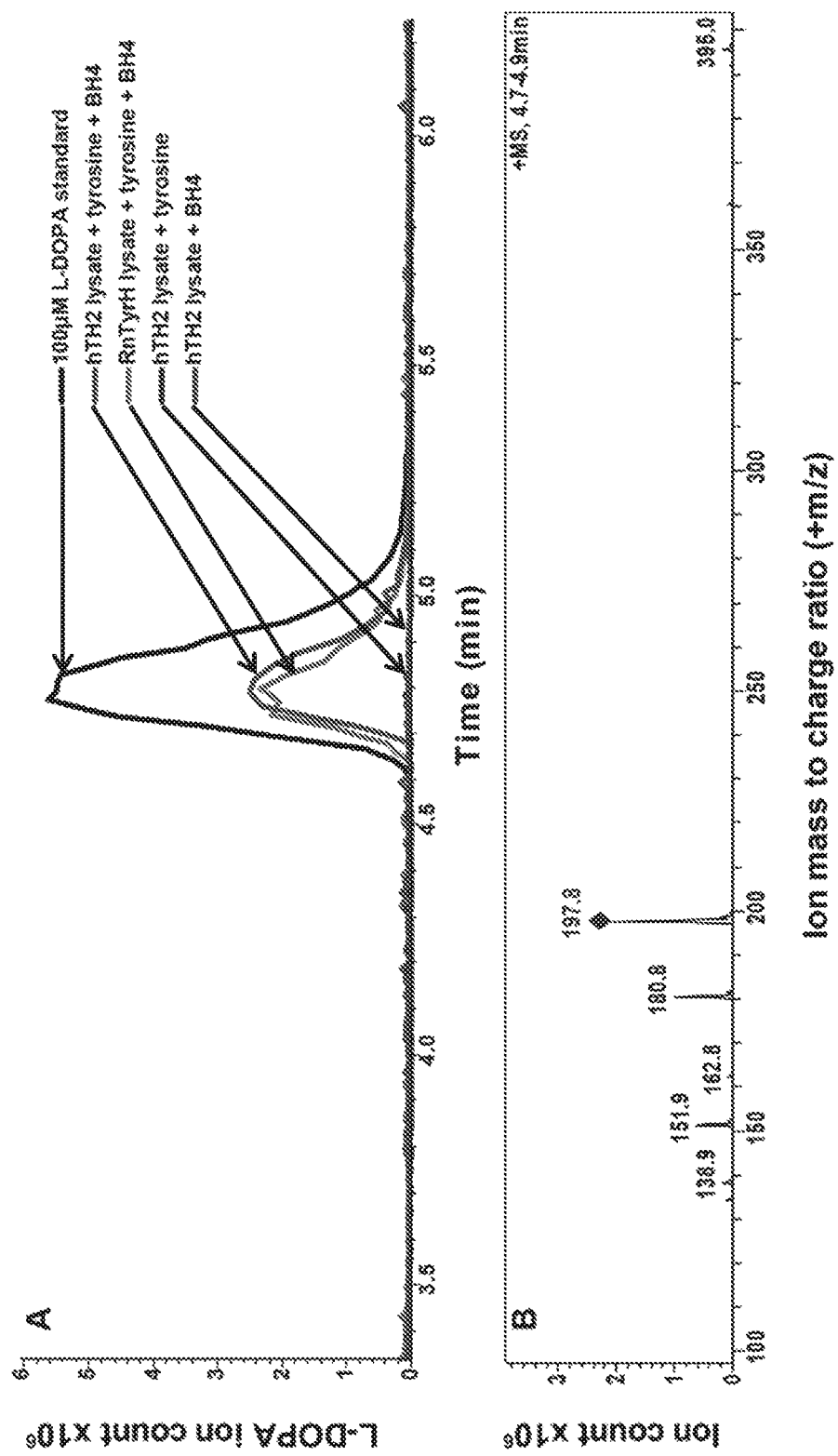
FIG. 12 shows that tyrosine hydroxylases expressed from yeast cells convert tyrosine to L-DOPA: (A) LC-MS chromatogram confirms conversion of tyrosine to L-DOPA in the presence of co-substrate, BH4; and (B) L-DOPA ion fragmentation in lysate samples.
Figure 13:
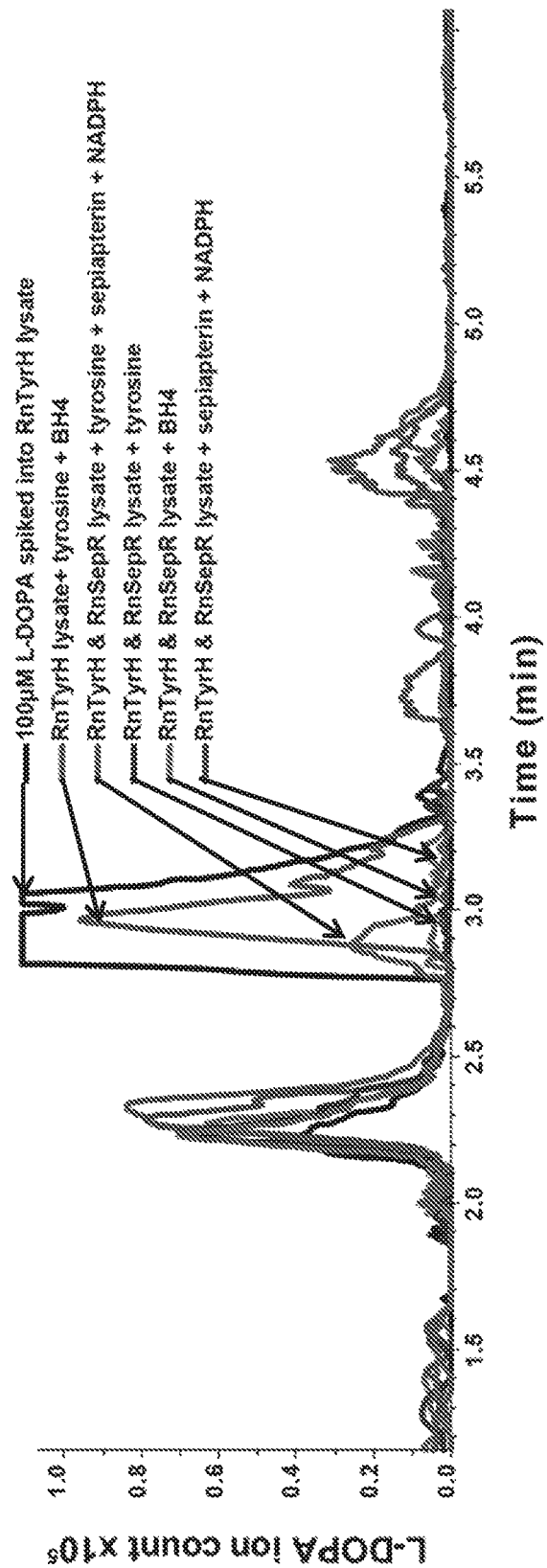
FIG. 13 shows the co-expression of tyrosine hydroxylase with a BH4 biosynthetic enzyme provides for conversion of tyrosine to L-DOPA.
Figure 14:
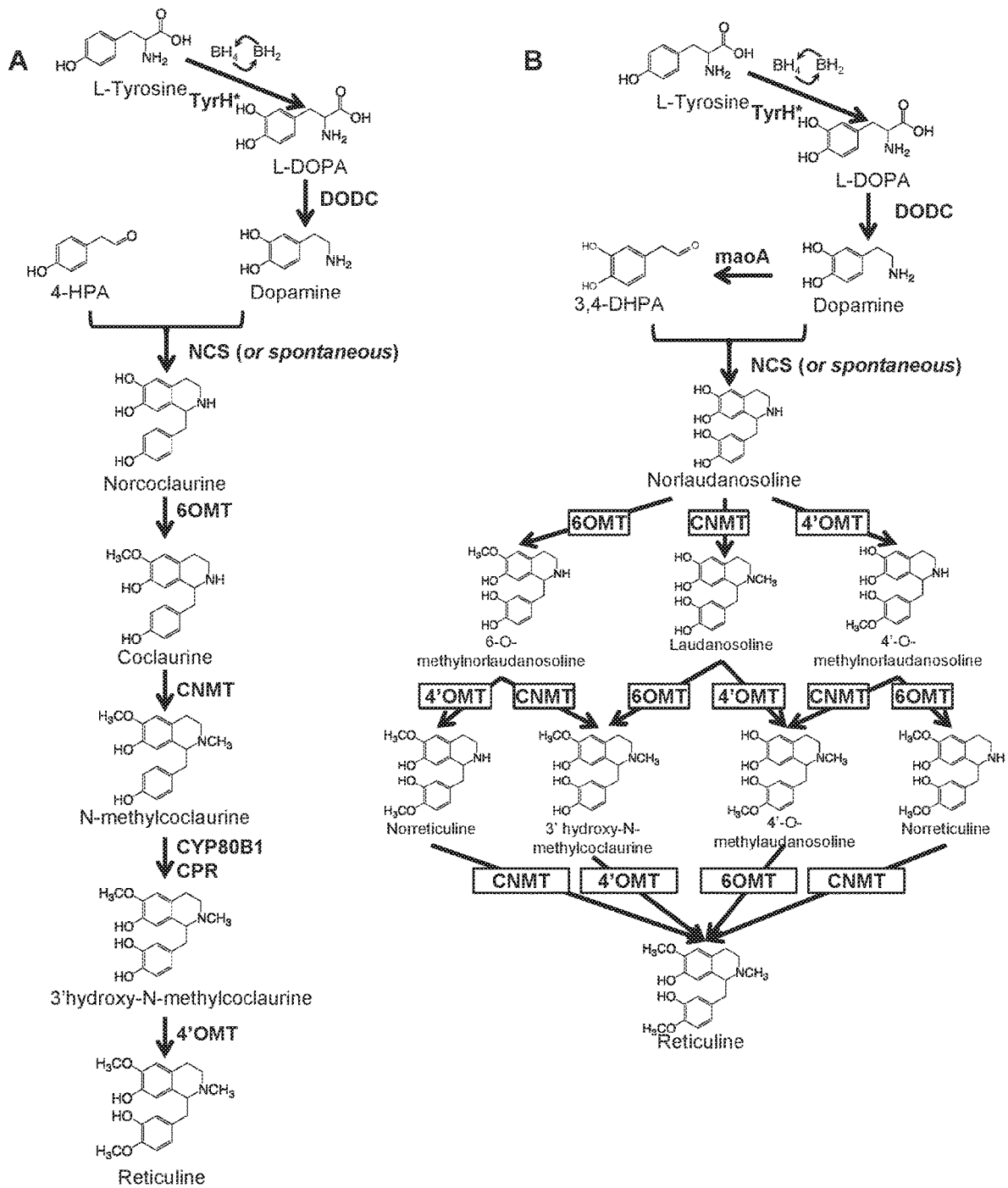
FIG. 14 illustrates the biosynthetic pathways of the BIA precursor molecules through to reticuline going through (A) NC and (B) NL.
Figure 15:
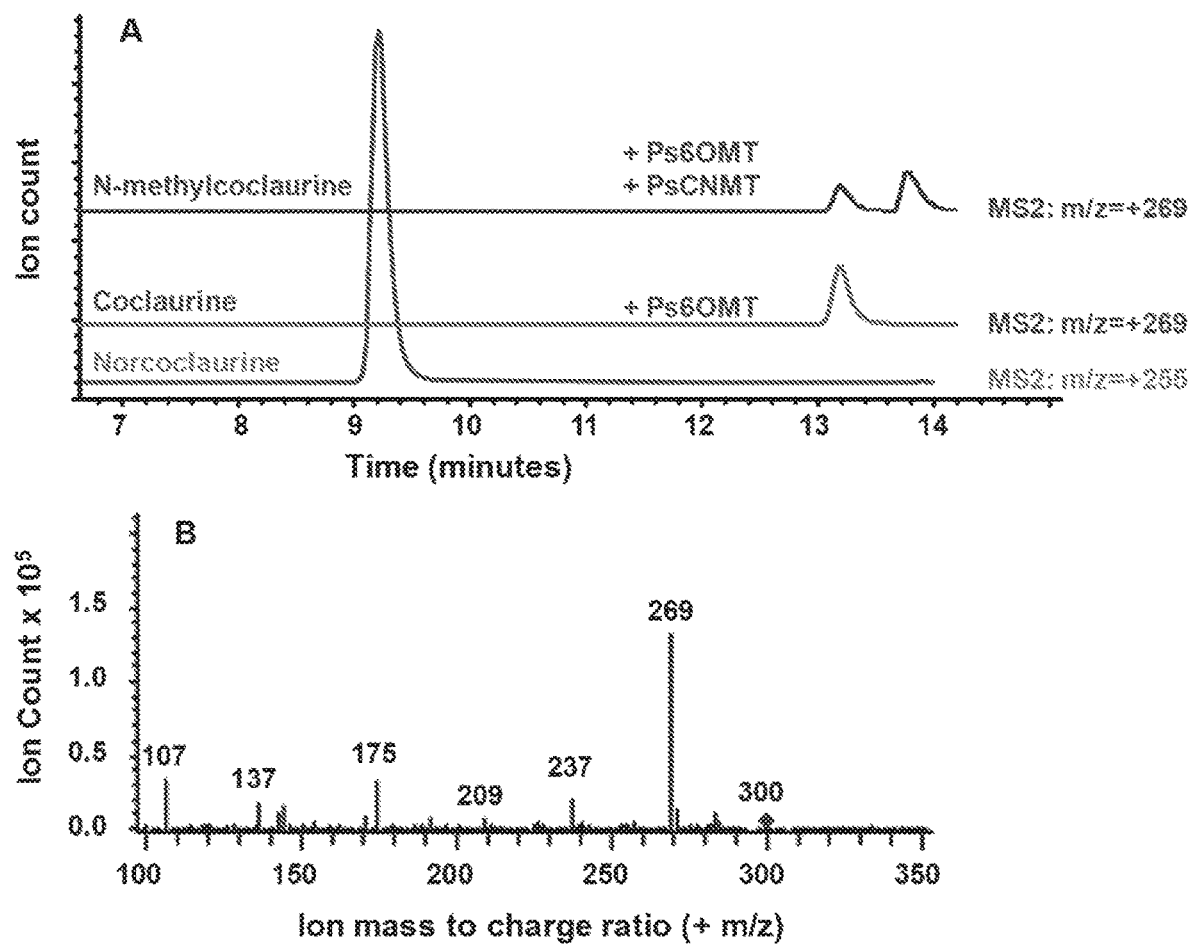
FIG. 15 shows LC-MS analysis (A: ion counts) of the production of NC-derived BIA precursor molecules including N-methylcoclaurine (B: m/z fragmentation pattern) from L-DOPA in the liquid culture of engineered yeast strains.
Figure 16:
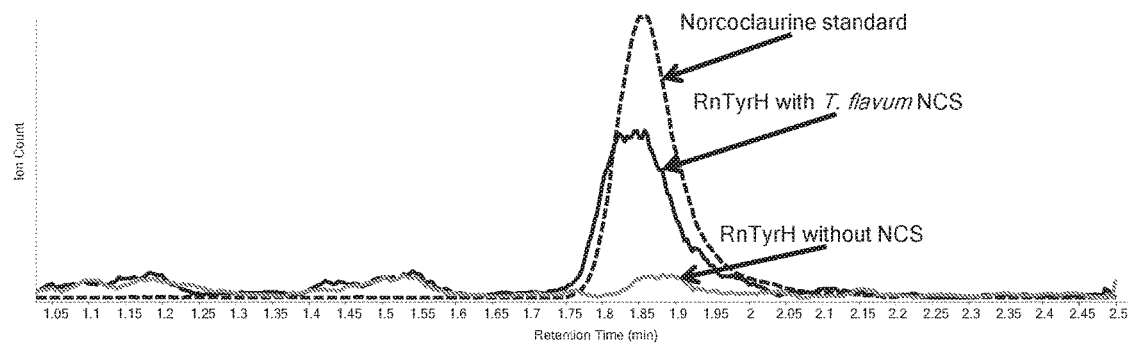
FIG. 16 shows LC-MS analysis (ion counts) of the production of (A) NC and (B) reticuline from sugar in the liquid culture of engineered yeast strains.
Figure 16:
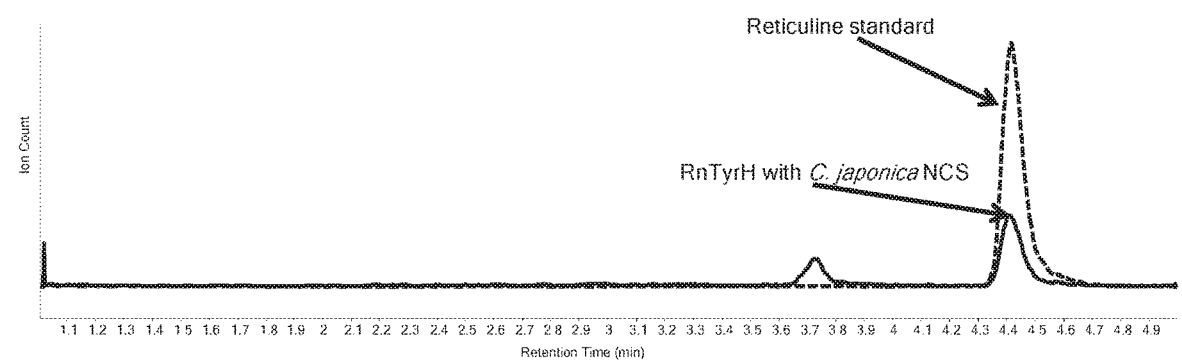

Engineered yeast strains produce NC-derived BIA molecules from L-DOPA in liquid culture. A copy of PpDODC was integrated into the engineered yeast strain, CSY1039 (as described in FIG. 9), providing for the production of NC from L-DOPA (panel A, bottom chromatogram). Next a copy of the opium poppy 6-O-methyltransferase (Ps6OMT) gene was integrated into this yeast strain to enable the production of coclaurine from L-DOPA (panel A, middle chromatogram). Finally, a copy of both Ps6OMT and the opium poppy coclaurine-N-methyltransferase (PsCNMT) genes were integrated into the CSY1039 yeast strain carrying the PpDODC gene to enable the production of N-methylcoclaurine from L-DOPA (panel A, top chromatogram). Both the NC and coclaurine measurements matched chromatograms from chemical standards. The production of N-methylcoclaurine was further confirmed by matching the fragmentation pattern of the +300 m/z ion peak to patterns in published literature (Panel B). (see e.g., Schmidt et al. (2007) Poppy alkaloid profiling by electrospray tandem mass spectrometry and electrospray FT-ICR mass spectrometry after [ring-13C6]-tyramine feeding. Phytochemistry 68(2):189-202).

FIG. 16

Engineered yeast strains produce norcoclaurine (as described in (2.5)) and reticuline (as described in (2.9)) from sugar in liquid culture. (A) LC-MS/MS was used in MRM mode to detect norcoclaurine with the transition 272 m/z to 107 m/z. The dashed line depicts a norcoclaurine standard. Grey line shows norcoclaurine production in an engineered yeast strain. The strain contains harbors the following modifications: ARO4$^{FBR}$, ZWF1 knockout, GPD-TKL1 promoter replacement; and expresses the following heterologous genes: wild type *R. norvegicus* tyrosine hydroxylase (RnTyrH; expressed from a low-copy plasmid), PpDODC (integrated into the chromosome), and BH$_4$ biosynthesis and recycling genes (RnPTPS, RnSepR, RnPCD, RnQDHPR; integrated into the chromosome). The black line depicts norcoclaurine production in the same strain as described for the grey line and also co-expressing *T. flavum* norcoclaurine synthase (TfNCS; expressed from a low-copy plasmid). (B) LC-MS/MS was used in MRM mode to detect reticuline with the transition 330 m/z to 137 m/z. The dashed line depicts a reticuline standard. The black line shows reticuline production in the strain described in (A, grey line) further engineered to express Ps6OMT, PsCNMT, EcCYP80B1, PsCPR, Ps4'OMT, and *Coptis japonica* norcoclaurine synthase (CjNCS; integrated into the chromosome).

FIG. 17

Effect of media composition on production of BIA products. Yeast strains engineered to produce reticuline (as described in (2.9)) from sugar were grown under various media conditions in liquid culture. LC-MS/MS was used in MRM mode to detect reticuline with the transition 330 m/z to 137 m/z in the growth media of strains grown for 72 hours at 30 C. (A) Reticuline production from yeast strain YA8 in a variety of media conditions. YPD, yeast peptone dextrose; YNB, yeast nitrogen base. (B) Optimization of reticuline titer while varying maltodextrin concentration and amylase concentration with two reticuline-producing yeast strains, YA8 and YA22. AGU, amyloglucosidase unit.

FIG. 18

Effect of inactivating mutations in ADH and ALD enzymes on production of BIA products. Combinations of inactivating mutations in ADH and ALD enzymes were incorporated into yeast strains engineered to produce reticuline (as described in (2.9)). The enzymes with inactivating mutations may include any combination of the following: ADH2, ADH3, ADH4, ADH5, ADH6, ADH7, ALD2, ALD3, ALD4, ALD5, or ALD6. In some cases, the cell will contain two, three, four, five, six, seven, eight, nine, ten, eleven, or more inactivating mutations. In certain cases, the enzymes containing inactivating mutations will be ADH2, ADH5, ADH6, and ALD4. In certain cases the enzymes containing inactivating mutations will be ADH2, ADH5, ADH6, ALD2, and ALD3. In some cases multiple ADH and ALD inactivating mutations will increase BIA product titer. Combinations of inactivating mutations in four enzymes (ADH2, ADH5, ADH6, ALD4) and five enzymes (ADH2, ADH5, ADH6, ALD2, ALD3) increases the production of reticuline from the reticuline-producing yeast strain (YA8). Yeast strains engineered to produce reticuline (as described in (2.9)) from sugar were grown in liquid culture for 72 hours at 30 C. LC-MS/MS was used in MRM mode to detect reticuline with the transition 330 m/z to 137 m/z in the growth media.

TABLE 1

| | | | | | | | |
|---|---|---|---|---|---|---|---|
| | | | | | Genes of interest as components of the engineered metabolic pathways | | |

| Enzyme | Abbrev. | Catalyzed reactions | Source organisms | Engineered regulation | Coding sequence changes | Genbank # | Specific description ref. |
|---|---|---|---|---|---|---|---|
| 3-deoxy-d-arabinose-heptulosonate-7-phosphate synthase | ARO4, DHAP synthase | erythrose-4-phosphate + PEP → DHAP (EC 2.5.1.54) | *Saccharomyces cerevisiae* | native, constitutive, synthetic regulation | Feedback inhibition resistant mutation, | CAA85212.1 | 1.1 |

TABLE 1-continued

Genes of interest as components of the engineered metabolic pathways

| Enzyme | Abbrev. | Catalyzed reactions | Source organisms | Engineered regulation | Coding sequence changes | Genbank # | Specific description ref. |
|---|---|---|---|---|---|---|---|
| Chorismate mutase | ARO7 | chorismate → prephenate (EC 5.4.99.5) | Saccharomyces cerevisiae | native, constitutive, synthetic regulation | K229L, Q166K Feedback inhibition resistant mutation, T226I | NP_015385.1 | 1.2 |
| Phenylpyruvate decarboxylase | ARO10 | hydroxyphenylpyruvate → 4HPA (EC 4.1.1.80) | Saccharomyces cerevisiae | constitutive overexpression, synthetic regulation | | NP_010668.3 | 1.3 |
| Aromatic aminotransferase | ARO9 | hydroxyphenylpyruvate + glutamate → tyrosine + alpha-ketoglutarate (EC 2.6.1.57) | Saccharomyces cerevisiae | constitutive overexpression, synthetic regulation | | AEC14313.1 | 1.4 |
| Transketolase | TKL1 | fructose-6-phosphate + glyceraldehyde-3-phosphate ↔ xylulose-5-phosphate + erythrose-4-phosphate (EC 2.2.1.1) | Saccharomyces cerevisiae | constitutive overexpression, synthetic regulation | | NP_015399.1 | 1.5 |
| Glucose-6-phosphate dehydrogenase | ZWF1 | glucose-6-phosphate → 6-phosphogluconolactone (EC 1.1.1.49) | Saccharomyces cerevisiae | | full deletion of coding region | CAA96146.1 | 1.6 |
| Alcohol dehydrogenase | ADH2-7, SFA1 | 4HPA → tyrosol (EC 1.1.1.90) | Saccharomyces cerevisiae | | full deletion of coding region | NP_014032.1, AAT93007.1, NP_011258.2, NP_009703.3, NP_014051.3, NP_010030.1, NP_010113.1 | 1.7 |
| Aldehyde oxidase | ALD2-6 | 4HPA → hydroxyphenylacetic acid (EC 1.2.1.39) | Saccharomyces cerevisiae | | full deletion of coding region | NP_013893.1, NP_013892.1, NP_015019.1, NP_010996.2, NP_015264.1 | 1.8 |
| Tyrosinase | TYR | tyrosine → L-DOPA, L-DOPA → dopaquinone (EC 1.14.18.1) | Ralstonia solanacearum, Agaricus bisporus | constitutive overexpression, synthetic regulation | | NP_518458.1, AJ223816, | 1.9 |
| Tyrosine hydroxylase | TyrH | tyrosine → L-DOPA (EC 1.14.16.2) | Homo sapiens, Rattus norvegicus, Mus musculus | constitutive overexpression, synthetic regulation | | NM 012740, NM 000240, | 1.9 |
| GTP cyclohydrolase | FOL2 | GTP → dihydroneopterin triphosphate (EC 3.5.4.16) | Saccharomyces cerevisiae, Homo sapiens, Mus musculus | native regulation, constitutive overexpression, synthetic regulation | | CAA97297.1, NP_001019195.1, NP_032128.1 | 1.9.1 |
| 6-pyruvoyl tetrahydrobiopterin (PTP) synthase | PTPS | dihydroneopterin triphosphate → PTP (EC 4.2.3.12) | Rattus norvegicus, Homo sapiens, Mus musculus | constitutive overexpression, synthetic regulation | | AAH59140.1, BAA04224.1, AAH29013.1 | 1.9.1 |
| Sepiapterin reductase | SepR | PTP → BH4 (EC 1.1.1.153) | Rattus norvegicus, Homo sapiens, Mus musculus | constitutive overexpression, synthetic regulation | | NP_062054.1, NP_003115.1, NP_035597.2 | 1.9.1 |
| 4a-hydroxytetrahydrobiopterin (pterin-4α-carbinolamine) dehydratase | PCD | 4a-hydroxytetrahydrobiopterin → H2O + quinoid dihydropteridine (EC 4.2.1.96) | Rattus norvegicus, Homo sapiens, Mus musculus | constitutive overexpression, synthetic regulation | | NP_001007602.1, AAB25581.1, NP_079549.1 | 1.9.1 |
| Quinoid dihydropteridine reductase | QDHPR | quinoid dihydropteridine → BH4 (EC 1.5.1.34) | Rattus norvegicus, Homo sapiens, Mus musculus | constitutive overexpression, synthetic regulation | | AAH72536.1, NP_000311.2, AAH02107.1 | 1.9.1 |
| L-DOPA decarboxylase | DODC | L-DOPA → dopamine (EC 4.1.1.28) | Pseudomonas putida, Rattus norvegicus | constitutive overexpression, synthetic regulation | | AE015451.1, NP_001257782.1 | 1.10 |
| Tyrosine/DOPA decarboxylase | TYDC | L-DOPA → dopamine (EC 4.1.1.28) | Papaver somniferum | constitutive overexpression, synthetic regulation | | | 1.10 |

TABLE 1-continued

Genes of interest as components of the engineered metabolic pathways

| Enzyme | Abbrev. | Catalyzed reactions | Source organisms | Engineered regulation | Coding sequence changes | Genbank # | Specific description ref. |
|---|---|---|---|---|---|---|---|
| Monoamine oxidase | MAO | dopamine → 3,4-DHPA (EC 1.4.3.4) | E. coli, Homo sapiens, Micrococcus luteus | constitutive overexpression, synthetic regulation | | J03792, D2367, AB010716.1 | 1.11, 1.11.1 |
| Norcoclaurine synthase | NCS | 4HPA + dopamine → S-norcoclaurine (EC 4.2.1.78) 3,4-DHPA + dopamine → S-norlaudanosoline | Coptis japonica, Papaver somniferum, Papver bracteatum, Thalicitum flavum, Corydalis saxicola | constitutive | N-terminal truncation | BAF45337.1, ACI45396.1, ACO90258.1, ACO90247.1, AEB71889.1 | 2.5, 3.5 |
| Norcoclaurine 6-O-methyltransferase | 6OMT | Norcoclaurine → coclaurine Norlaudanosoline → 3'hydroxycoclaurine EC 2.1.1.128 | Papaver somniferum, Thalicitum flavum, Coptis japonica, Papaver bracteatum, Eschscholzia califomica | constitutive overexpression, synthetic regulation | | AY268894 AY610507 D29811 ACO90225.1 BAM37634.1 | 2.6-2.9, 3.6, 3.8, 3.10, 3.12 |
| Coclaurine-N-methyltransferase | CNMT | Coclaurine → N-methylcoclaurine 3'hydroxycoclaurine → 3'-hydroxy-N-methylcoclaurine EC 2.1.1.140 | P. somniferum, T. flavum, Coptis japonica | constitutive overexpression, synthetic regulation | | AY217336 AY610508 AB061863 | 2.7-2.9, 3.7, 3.8, 3.11, 3.12 |
| Cytochrome P450 80B1 | CYP80B1 | N-methylcoclaurine → 3'-hydroxy-N-methylcoclaurine | P. somniferum, E. califomica, T. flavum | constitutive overexpression, synthetic regulation | | AAF61400.1 AAC39453.1 AAU20767.1 | 2.8, 2.9 |
| NADPH:hemoprotein oxidoreductase, also known as cytochrome P450 reductase | ATR1, CPR | NADPH + H⁺ + n oxidized hemoprotein → NADP⁺ + n reduced hemoprotein | Arabidopsis thaliana, P. somniferum | constitutive overexpression, synthetic regulation | | AAC05021.1 CAB58576.1 CAB58575.1 | 2.8, 2.9 |
| 4'-O-methyltransferase | 4'OMT | 3'-hydroxy-N-methylcoclaurine → reticuline EC 2.1.1.116 | P. somniferum, T. flavum, Coptis japonica, E. califomica | constitutive overexpression, synthetic regulation | | AY217333, AY217334 AY610510 D29812 BAM37633.1 | 2.9, 3.9-3.12 |

TABLE 2

Comparison of impurities that may be present in concentrate of poppy straw (or opium) and clarified yeast culture medium.

| Impurities: | | Concentrate of Poppy Straw | Clarified Yeast Culture Medium |
|---|---|---|---|
| Inorganic | Sodium | ✓ | ✓ |
| | Magnesium | ✓ | ✓ |
| | Silicon | ✓ | x (not in culture medium) |
| | Phosphorus | ✓ | ✓ |
| | Sulfur | ✓ | ✓ |
| | Chloride | ✓ | ✓ |
| | Potassium | ✓ | ✓ |
| | Calcium | ✓ | ✓ |
| | Copper | ✓ | ✓ |
| | Zinc | ✓ | ✓ |
| | Molybdenum | ✓ | ✓ (sodium molybdate in medium) |
| | Iron | ✓ | ✓ |
| | Manganese | ✓ | ✓ |
| | Ammonium | ✓ | ✓ |
| | Boron | ✓ | ✓ |
| Organic | Polysaccharides (starch, cellulose, xylan) | ✓ | x (yeast fed simple sugars) |
| | Lignin (p-cournaryl, coniferyl, sinapyl alcohols) | ✓ | x |
| | Pigments (chlorophyll, anthocyanins, carotenoids) | ✓ | x |
| | Flavonoids | ✓ | x |
| | Phenanthreoids | ✓ | x |
| | Latex, gum, and wax | ✓ | x |
| | Rubisco | ✓ | x |
| | Meconic acid | ✓ | x |
| | Pseudomorphine | ✓ | x |
| | Narceine | ✓ | x |
| | Thebaol | ✓ | x |
| Other | Pesticides, Fungicides, Herbicides | ✓ | x |
| | Pollen | ✓ | x |

TABLE 3

Distinct groups of molecules present in clarified yeast culture medium (CYCM). Unlike concentrate of poppy straw (CPS) or opium, yeast host strains may be engineered to produce molecules of a predetermined class of alkaloids (i.e., only one biosynthesis pathway per strain) such that other classes of alkaloids are not present. Therefore, the CYCM may contain molecules within a single biosynthesis pathway including a subset of molecules spanning one or two columns, whereas the CPS may contain a subset of molecules across many columns.

| 1-Benzylisoquinoline | Protoberberine and Phthalideisoquinoline | Morphinan | Isopavine | Aporphine | BisBIA |
|---|---|---|---|---|---|
| Tetrahydropapaverine | Scoulerine | Salutaridine | Pavine | Magnoflorine | Dauricine |
| Dihydropapaverine | Chelanthifoline | Salutaridinol | Caryachine | Corytuberine | Berbamunine |
| Papaverine | Stylopine | Salutaridine-7-O-acetate | Bisnorargemonine | Apomorphine | Ligensinine |
|  | Cis-N-methylstylopine | Thebaine | Isonoraremonine | Boldine | Fangchinoline |
|  | Protopine | Codeinone |  |  | Tetrandrine |
|  | Dihydrosanguinarine | Oripavine |  |  | Curine |
|  | Sanguinarine | Morphinone |  |  | Cepharanthine |
|  | Tetrahydrocolumbamine | Neopinone |  |  | Berbamine |
|  | Canadine | Neopine |  |  |  |
|  | N-methylcanadine | Codeine |  |  |  |
|  | Noscapine | Morphine |  |  |  |
|  | Berberine | Neomorphine |  |  |  |
|  | Narcotoline | Hydrocodone |  |  |  |
|  | Narcotinehemiacetal | Oxycodone |  |  |  |
|  | Narcotolinehemiacetal | 14-hydroxycodeinone |  |  |  |
|  |  | 14-hydroxycodeine |  |  |  |
|  |  | Dihydromorphine |  |  |  |
|  |  | Dihydrocodeine |  |  |  |
|  |  | Oxymorphone |  |  |  |
|  |  | Hydromorphone |  |  |  |

Notwithstanding the appended clauses, the disclosure is also defined by the following clauses:

1. A method for forming a product stream having a benzylisoquinoline alkaloid product, the method comprising:
   (a) providing engineered yeast cells and a feedstock including nutrients and water to a batch reactor, which engineered yeast cells have at least one modification that results in overproduction of tyrosine with respect to a non-engineered yeast cell, wherein the at least one modification is selected from the group consisting of: a feedback inhibition alleviating mutation in a biosynthetic enzyme gene and an inactivating mutation in an enzyme;
   (b) in the batch reactor, subjecting the engineered yeast cells to fermentation by incubating the engineered yeast cells for a time period of at least about 5 minutes to produce a solution comprising the benzylisoquinoline alkaloid product and cellular material; and
   (c) using at least one separation unit to separate the benzylisoquinoline alkaloid product from the cellular material to provide the product stream comprising the benzylisoquinoline alkaloid product.
2. The method of clause 1, wherein the engineered yeast cell comprises one or more feedback inhibition alleviating mutations in one or more biosynthetic enzyme genes that encode 3-deoxy-d-arabinose-heptulosonate-7-phosphate synthase.
3. The method of clause 2, wherein the one or more feedback inhibition alleviating mutations are present in the 3-deoxy-d-arabinose-heptulosonate-7-phosphate synthase gene.
4. The method of clause 1, wherein the engineered yeast cell comprises one or more feedback inhibition alleviating mutations in one or more biosynthetic enzyme genes that encode chorismate mutase.
5. The method of clause 4, wherein the one or more feedback inhibition alleviating mutations are present in the chorismate mutase gene.
6. The method of clause 1, wherein the engineered yeast cell further comprises at least one transcriptional modulation modification in a biosynthetic enzyme gene.
7. The method of clause 1, wherein at least one process parameter of the batch reactor is modifiable to alter a resultant benzylisoquinoline alkaloid product composition.
8. The method of clause 7, wherein the at least one process parameter that is modifiable comprises at least one of dissolved oxygen, pH, stirring speed, aeration rate, and cell density.
9. The method of clause 1, wherein the benzylisoquinoline alkaloid product comprises a benzylisoquinoline alkaloid precursor.
10. The method of clause 9, wherein the benzylisoquinoline alkaloid precursor is selected from the group of norcoclaurine, norlaudanosoline, tyrosine, tyramine, 4-hydroxyphenylacetaldehyde, 4-hydroxyphenylpyruvic acid, L-3,4-dihydroxyphenylalanine, 3,4-dihydroxyphenylacetaldehyde, and dopamine.
11. The method of clause 1, wherein the benzylisoquinoline alkaloid product comprises a benzylisoquinoline alkaloid.
12. The method of clause 11, wherein the benzylisoquinoline alkaloid has a structural class that is selected from the group of benzylisoquinolines, protoberberines, protopines, benzophenanthridines, promorphinans, morphinans, secoberberines, phthalideisoquinolines, aporphines, and bisbenzylisoquinolines.
13. The method of clause 12, wherein the benzylisoquinoline alkaloid is a benzylisoquinoline that is selected from the group of coclaurine, 3'-hydroxycoclaurine, 4'-O-methylnorlaudanosoline, 4'-O-methyl-laudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine, and orientaline.
14. The method of clause 12, wherein the benzylisoquinoline alkaloid is a protoberberine that is selected from the group of scoulerine, cheilanthifoline, stylopine, nandinine, jatrorrhizine, stepholidine, discretamine, cis-N-methylstylopine, tetrahydrocolumbamine, palmatine, tetrahydropalmatine, columbamine, canadine, N-methylcanadine, 1-hydroxycanadine, berberine, N-methyl-ophiocarpine, 1,13-dihydroxy-N-methylcanadine, and 1-hydroxy-10-O-acetyl-N-methylcanadine.

15. The method of clause 12, wherein the benzylisoquinoline alkaloid is a protopine that is selected from the group of protopine, 6-hydroxyprotopine, allocryptopine, cryptopine, muramine, and thalictricine.

16. The method of clause 12, wherein the benzylisoquinoline alkaloid is a benzophenanthridine that is selected from the group of dihydrosanguinarine, sanguinarine, dihydrocheilirubine, cheilirubine, dihydromarcapine, marcapine, and chelerythrine.

17. The method of clause 12, wherein the benzylisoquinoline alkaloid is a promorphinan that is selected from the group of salutaridine, salutaridinol, and salutaridinol-7-O-acetate.

18. The method of clause 12, wherein the benzylisoquinoline alkaloid is a morphinan that is selected from the group of thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone.

19. The method of clause 12, wherein the benzylisoquinoline alkaloid is a secoberberine that is selected from the group of 4'-O-desmethylmacrantaldehyde, 4'-O-desmethylpapaveroxine, 4'-O-desmethyl-3-O-acetylpapaveroxine, and 3-O-aceteylpapaveroxine.

20. The method of clause 12, wherein the benzylisoquinoline alkaloid is a phthalideisoquinoline that is selected from the group of narcotolinehemiacetal, narcotinehemiacetal, narcotoline, and noscapine.

21. The method of clause 12, wherein the benzylisoquinoline alkaloid is an aporphine that is selected from the group of magnoflorine, corytuberine, apomorphine, boldine, isoboldine, isothebaine, isocorytuberine, and glaufine.

22. The method of clause 12, wherein the benzylisoquinoline alkaloid is a bisbenzylisoquinoline that is selected from the group of berbamunine, guattgaumerine, dauricine, and liensinine.

23. A method for forming a product stream having a benzylisoquinoline alkaloid product, the method comprising:
    (a) providing engineered yeast cells and a feedstock including nutrients and water to a reactor;
    (b) in the reactor, subjecting the engineered yeast cells to fermentation by incubating the engineered yeast cells for a time period of at least about 5 minutes to produce a solution comprising cellular material and the benzylisoquinoline alkaloid product, wherein the solution comprises not more than one class of molecule selected from the group of protoberberine, morphinan, isopavine, aporphine, and bisbenzylisoquinoline; and
    (c) using at least one separation unit to separate the benzylisoquinoline alkaloid product from the cellular material to provide the product stream comprising the benzylisoquinoline alkaloid product.

24. The method of clause 23, wherein the engineered yeast cells have at least one modification that results in overproduction of tyrosine with respect to a non-engineered yeast cell, wherein the at least one modification is selected from the group consisting of: a feedback inhibition alleviating mutation in a biosynthetic enzyme gene and an inactivating mutation in an enzyme.

25. The method of clause 24, wherein the engineered yeast cell further comprises at least one transcriptional modulation modification in a biosynthetic enzyme gene.

26. The method of clause 23, wherein the product stream does not contain more than 5 ppm of a molecule selected from the group of lignin, pigments, flavonoids, phenanthreoids, latex, rubisco, meconic acid, pseudomorphine, narceine, thebaol, and pollen.

27. The method of clause 26, wherein the product stream does not contain more than 5 ppm of meconic acid.

28. The method of clause 23, wherein the product stream does not contain a detectable amount of a substance selected from the group consisting of pesticides, fungicides, or herbicides.

29. The method of clause 23, wherein the benzylisoquinoline alkaloid product is recovered from the product stream through liquid-liquid extraction.

30. The method of clause 29, wherein the benzylisoquinoline alkaloid product is recovered immediately after a fermentation process has been completed.

31. The method of any of the previous clauses, wherein the engineered yeast cell comprises two or more heterologous coding sequences, wherein the two or more heterologous coding sequences encode at least a first enzyme and a second enzyme that are involved in a metabolic pathway that converts the tyrosine into the benzylisoquinoline alkaloid product, wherein the first enzyme and second enzyme are operably connected along the metabolic pathway.

32. The method of any of the previous clauses, wherein the engineered yeast cell comprises three heterologous coding sequences, wherein the three heterologous coding sequences encode a first enzyme, second enzyme, and third enzyme that are involved in a metabolic pathway that converts the tyrosine into the benzylisoquinoline alkaloid product, wherein the first enzyme, second enzyme, and third enzyme are operably connected along the metabolic pathway.

33. An engineered yeast cell that produces a benzylisoquinoline alkaloid product, the engineered yeast cell having at least one modification that results in overproduction of tyrosine with respect to a non-engineered yeast cell, wherein the at least one modification is selected from the group consisting of: a feedback inhibition alleviating mutation in a biosynthetic enzyme gene and an inactivating mutation in an enzyme,
wherein the engineered yeast cell comprises at least one heterologous coding sequence encoding at least one enzyme that is selected from the group of tyrosine hydroxylase, L-DOPA decarboxylase, and norcoclaurine synthase.

34. The engineered yeast cell of clause 33, wherein the engineered yeast cell further comprises at least one heterologous coding sequence encoding at least one enzyme that is selected from the group of norcoclaurine 6-O-methyltransferase, coclaurine-N-methyltransferase, cytochrome P450 80B1, cytochrome P450 reductase, and 4'-O-methyltransferase.

35. The engineered yeast cell of clause 34, wherein the benzylisoquinoline alkaloid product comprises at least one of coclaurine, N-methylcoclaurine, 3'hydroxy-N-methyl-coclaurine, 3'hydroxycoclaurine, laudanosoline, 4'-O-methyllaudanosoline, norreticuline, and reticuline.

36. A method for forming a product stream having a benzylisoquinoline alkaloid product, the method comprising:
    (a) providing engineered non-plant cells and a feedstock including nutrients and water to a batch reactor, which engineered non-plant cells have at least one modification that results in overproduction of tyrosine with respect to a non-engineered non-plant cell, wherein the at least one modification is selected from the group consisting of: a feedback inhibition alleviating mutation in a biosynthetic enzyme gene and an inactivating mutation in an enzyme;

(b) in the batch reactor, subjecting the engineered non-plant cells to fermentation by incubating the engineered non-plant cells for a time period of at least about 5 minutes to produce a solution comprising the benzylisoquinoline alkaloid product and cellular material; and (c) using at least one separation unit to separate the benzylisoquinoline alkaloid product from the cellular material to provide the product stream comprising the benzylisoquinoline alkaloid product.

37. The method of clause 36, wherein the engineered non-plant cell comprises one or more feedback inhibition alleviating mutations in one or more biosynthetic enzyme genes that encode 3-deoxy-d-arabinose-heptulosonate-7-phosphate synthase.

38. The method of clause 37, wherein the one or more feedback inhibition alleviating mutations are present in the 3-deoxy-d-arabinose-heptulosonate-7-phosphate synthase gene.

39. The method of clause 36, wherein the engineered non-plant cell comprises one or more feedback inhibition alleviating mutations in one or more biosynthetic enzyme genes that encode chorismate mutase.

40. The method of clause 39, wherein the one or more feedback inhibition alleviating mutations are present in the chorismate mutase gene.

41. The method of clause 36, wherein the engineered non-plant cell further comprises at least one transcriptional modulation modification in a biosynthetic enzyme gene.

42. The method of clause 36, wherein at least one process parameter of the batch reactor is modifiable to alter a resultant benzylisoquinoline alkaloid product composition.

43. The method of clause 42, wherein the at least one process parameter that is modifiable comprises at least one of dissolved oxygen, pH, stirring speed, aeration rate, and cell density.

44. The method of clause 36, wherein the benzylisoquinoline alkaloid product comprises a benzylisoquinoline alkaloid precursor.

45. The method of clause 44, wherein the benzylisoquinoline alkaloid precursor is selected from the group of norcoclaurine, norlaudanosoline, tyrosine, tyramine, 4-hydroxyphenylacetaldehyde, 4-hydroxyphenylpyruvic acid, L-3,4-dihydroxyphenylalanine, 3,4-dihydroxyphenylacetaldehyde, and dopamine.

46. The method of clause 36, wherein the benzylisoquinoline alkaloid product comprises a benzylisoquinoline alkaloid.

47. The method of clause 46, wherein the benzylisoquinoline alkaloid has a structural class that is selected from the group of benzylisoquinolines, protoberberines, protopines, benzophenanthridines, promorphinans, morphinans, secoberberines, phthalideisoquinolines, aporphines, and bisbenzylisoquinolines.

48. The method of clause 47, wherein the benzylisoquinoline alkaloid is a benzylisoquinoline that is selected from the group of coclaurine, 3'-hydroxycoclaurine, 4'-O-methylnorlaudanosoline, 4'-O-methyl-laudanosoline, N-methylnorcoclaurine, laudanosoline, N-methylcoclaurine, 3'-hydroxy-N-methylcoclaurine, reticuline, norreticuline, papaverine, laudanine, laudanosine, tetrahydropapaverine, 1,2-dihydropapaverine, and orientaline.

49. The method of clause 47, wherein the benzylisoquinoline alkaloid is a protoberberine that is selected from the group of scoulerine, cheilanthifoline, stylopine, nandinine, jatrorrhizine, stepholidine, discretamine, cis-N-methylstylopine, tetrahydrocolumbamine, palmatine, tetrahydropalmatine, columbamine, canadine, N-methylcanadine, 1-hydroxycanadine, berberine, N-methyl-ophiocarpine, 1,13-dihydroxy-N-methylcanadine, and 1-hydroxy-10-O-acetyl-N-methylcanadine.

50. The method of clause 47, wherein the benzylisoquinoline alkaloid is a protopine that is selected from the group of protopine, 6-hydroxyprotopine, allocryptopine, cryptopine, muramine, and thalictricine.

51. The method of clause 47, wherein the benzylisoquinoline alkaloid is a benzophenanthridine that is selected from the group of dihydrosanguinarine, sanguinarine, dihydrocheilirubine, cheilirubine, dihydromarcapine, marcapine, and chelerythrine.

52. The method of clause 47, wherein the benzylisoquinoline alkaloid is a promorphinan that is selected from the group of salutaridine, salutaridinol, and salutaridinol-7-O-acetate.

53. The method of clause 47, wherein the benzylisoquinoline alkaloid is a morphinan that is selected from the group of thebaine, codeinone, codeine, morphine, morphinone, oripavine, neopinone, neopine, neomorphine, hydrocodone, dihydrocodeine, 14-hydroxycodeinone, oxycodone, 14-hydroxycodeine, morphinone, hydromorphone, dihydromorphine, dihydroetorphine, ethylmorphine, etorphine, metopon, buprenorphine, pholcodine, heterocodeine, and oxymorphone.

54. The method of clause 47, wherein the benzylisoquinoline alkaloid is a secoberberine that is selected from the group of 4'-O-desmethylmacrantaldehyde, 4'-O-desmethylpapaveroxine, 4'-O-desmethyl-3-O-acetylpapaveroxine, and 3-O-aceteylpapaveroxine.

55. The method of clause 47, wherein the benzylisoquinoline alkaloid is a phthalideisoquinoline that is selected from the group of narcotolinehemiacetal, narcotinehemiacetal, narcotoline, and noscapine.

56. The method of clause 47, wherein the benzylisoquinoline alkaloid is an aporphine that is selected from the group of magnoflorine, corytuberine, apomorphine, boldine, isoboldine, isothebaine, isocorytuberine, and glaufine.

57. The method of clause 47, wherein the benzylisoquinoline alkaloid is a bisbenzylisoquinoline that is selected from the group of berbamunine, guattgaumerine, dauricine, and liensinine.

58. A method for forming a product stream having a benzylisoquinoline alkaloid product, the method comprising:

(a) providing engineered non-plant cells and a feedstock including nutrients and water to a reactor;

(b) in the reactor, subjecting the engineered non-plant cells to fermentation by incubating the engineered non-plant cells for a time period of at least about 5 minutes to produce a solution comprising cellular material and the benzylisoquinoline alkaloid product, wherein the solution comprises not more than one class of molecule selected from the group of protoberberine, morphinan, isopavine, aporphine, and bisbenzylisoquinoline; and (c) using at least one separation unit to separate the benzylisoquinoline alkaloid product from the cellular material to provide the product stream comprising the benzylisoquinoline alkaloid product.

59. The method of clause 58, wherein the engineered non-plant cells have at least one modification that results in overproduction of tyrosine with respect to a non-engineered non-plant cell, wherein the at least one modification is selected from the group consisting of: a feedback inhibition alleviating mutation in a biosynthetic enzyme gene and an inactivating mutation in an enzyme.
60. The method of clause 59, wherein the engineered non-plant cell further comprises at least one transcriptional modulation modification in a biosynthetic enzyme gene.
61. The method of clause 58, wherein the product stream does not contain more than 5 ppm of a molecule selected from the group of lignin, pigments, flavonoids, phenanthreoids, latex, rubisco, meconic acid, pseudomorphine, narceine, thebaol, and pollen.
62. The method of clause 61, wherein the product stream does not contain more than 5 ppm of meconic acid.
63. The method of clause 58, wherein the product stream does not contain a detectable amount of a substance selected from the group consisting of pesticides, fungicides, or herbicides.
64. The method of clause 58, wherein the benzylisoquinoline alkaloid product is recovered from the product stream through liquid-liquid extraction.
65. The method of clause 64, wherein the benzylisoquinoline alkaloid product is recovered immediately after a fermentation process has been completed.
66. The method of any of the previous clauses, wherein the engineered non-plant cell comprises two or more heterologous coding sequences, wherein the two or more heterologous coding sequences encode at least a first enzyme and a second enzyme that are involved in a metabolic pathway that converts the tyrosine into the benzylisoquinoline alkaloid product, wherein the first enzyme and second enzyme are operably connected along the metabolic pathway.
67. The method of any of the previous clauses, wherein the engineered non-plant cell comprises three heterologous coding sequences, wherein the three heterologous coding sequences encode a first enzyme, second enzyme, and third enzyme that are involved in a metabolic pathway that converts the tyrosine into the benzylisoquinoline alkaloid product, wherein the first enzyme, second enzyme, and third enzyme are operably connected along the metabolic pathway.
68. An engineered non-plant cell that produces a benzylisoquinoline alkaloid product, the engineered non-plant cell having at least one modification that results in overproduction of tyrosine with respect to a non-engineered non-plant cell, wherein the at least one modification is selected from the group consisting of: a feedback inhibition alleviating mutation in a biosynthetic enzyme gene and an inactivating mutation in an enzyme,
wherein the engineered non-plant cell comprises at least one heterologous coding sequence encoding at least one enzyme that is selected from the group of tyrosine hydroxylase, L-DOPA decarboxylase, and norcoclaurine synthase.
69. The engineered non-plant cell of clause 68, wherein the engineered non-plant cell further comprises at least one heterologous coding sequence encoding at least one enzyme that is selected from the group of norcoclaurine 6-O-methyltransferase, coclaurine-N-methyltransferase, cytochrome P450 80B1, cytochrome P450 reductase, and 4'-O-methyltransferase.
70. The engineered non-plant cell of clause 69, wherein the benzylisoquinoline alkaloid product comprises at least one of coclaurine, N-methylcoclaurine, 3'hydroxy-N-methyl-coclaurine, 3'hydroxycoclaurine, laudanosoline, 4'-O-methyllaudanosoline, norreticuline, and reticuline.
71. The engineered non-plant cell of any of the previous clauses, wherein the engineered non-plant cell comprises two or more heterologous coding sequences, wherein the two or more heterologous coding sequences encode at least a first enzyme and a second enzyme that are involved in a metabolic pathway that converts the tyrosine into the benzylisoquinoline alkaloid product, wherein the first enzyme and second enzyme are operably connected along the metabolic pathway.
72. The engineered non-plant cell of any of the previous clauses, wherein the engineered non-plant cell comprises three heterologous coding sequences, wherein the three heterologous coding sequences encode a first enzyme, second enzyme, and third enzyme that are involved in a metabolic pathway that converts the tyrosine into the benzylisoquinoline alkaloid product, wherein the first enzyme, second enzyme, and third enzyme are operably connected along the metabolic pathway.
73. A compound that comprises:
a benzylisoquinoline alkaloid product that is characterized as being part of at most two classes selected from the group consisting of 1-benzylisoquinoline, protoberberine, morphinan, isopavine, aporphine, and bisbenzylisoquinoline,
wherein remaining components of the compound do not contain a detectable amount of a molecule of a non-selected class from the group of 1-benzylisoquinoline, protoberberine, morphinan, isopavine, aporphine, and bisbenzylisoquinoline.
74. The compound of clause 73, wherein the benzylisoquinoline alkaloid product is characterized as having a detectable amount of at most one class selected from the group consisting of 1-benzylisoquinoline, protoberberine, morphinan, isopavine, aporphine, and bisbenzylisoquinoline.
75. The compound of clause 73, wherein the benzylisoquinoline alkaloid product is characterized as being part of the 1-benzylisoquinoline class and also being part of at most one class selected from the group consisting of protoberberine, morphinan, isopavine, aporphine, and bisbenzylisoquinoline.
76. A therapeutic agent that comprises:
a benzylisoquinoline alkaloid product,
wherein the therapeutic agent does not contain a detectable amount of an impurity selected from the group consisting of codeine-O(6)-methyl ether, 8,14-dihydroxy-7,8-dihydrocodeinone, and tetrahydrothebaine.
77. The method of any of clauses 23-32, wherein the solution comprises no detectable amount of molecules selected from the group of protoberberine, morphinan, isopavine, aporphine, and bisbenzylisoquinoline, and wherein the solution comprises molecules within a class of phthalideisoquinolines.
78. The method of any of clauses 23-32, wherein the solution comprises molecules within the class of protoberberine, and wherein the solution further comprises molecules within a class of phthalideisoquinolines.
79. The method of any of clauses 58-67, wherein the solution comprises no detectable amount of molecules selected from the group of protoberberine, morphinan, isopavine, aporphine, and bisbenzylisoquinoline, and wherein the solution comprises molecules within a class of phthalideisoquinolines.
80. The method of any of clauses 58-67, wherein the solution comprises molecules within the class of protoberberine, and wherein the solution further comprises molecules within a class of phthalideisoquinolines.

81. The compound of any of clauses 73-75, wherein the benzylisoquinoline alkaloid product is not classified as being part of a class selected from the group consisting of 1-benzylisoquinoline, protoberberine, morphinan, isopavine, aporphine, and bisbenzylisoquinoline, and wherein the benzylisoquinoline alkaloid product is classified as being part of a phthalideisoquinoline alkaloid class.

82. The method of any of clauses 73-75, wherein the benzylisoquinoline alkaloid product is classified as being part of the protoberberine class and the phthalideisoquinoline class.

83. The method of any of clauses 73-75, wherein the benzylisoquinoline alkaloid product is classified as being part of the 1-benzylisoquinoline class, the protoberberine class, and the phthalideisoquinoline class.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for forming a product stream having a benzylisoquinoline alkaloid product, the method comprising:
   (a) providing engineered non-plant cells and a feedstock including nutrients and water to a batch reactor, which engineered non-plant cells have modifications that result in overproduction of a derivative of tyrosine, along a pathway to produce the benzylisoquinoline alkaloid product, with respect to a non-engineered non-plant cell, wherein the modifications comprise at least three modifications, wherein at least one modification of the at least three modifications is a transcriptional modulation mutation or an inactivating mutation, and wherein each modification of the at least three modifications is selected from the group consisting of: a feedback inhibition alleviating mutation, a transcriptional modulation mutation, and an inactivating mutation, wherein a first modification of the at least three modifications is associated with a first enzyme, a second modification of the at least three modifications is associated with a second enzyme, and a third modification of the at least three modifications is associated with a third enzyme, and wherein each enzyme of the first, second, and third enzymes is distinct from any other enzyme of the first, second, and third enzymes, and wherein each enzyme of the first, second, and third enzyme is selected from the group consisting of: transketolase, glucose-6-phosphate dehydrogenase, pentafunctional AROM protein, 3-deoxy-D-arabino-heptulosonate-7-phosphate synthase, chorismate mutase, tyrosinase, tyrosine hydroxylase, L-DOPA decarboxylase, monoamine oxidase, aromatic/aminoadipate aminotransferase, aromatic aminotransferase, phenylpyruvate decarboxylase, alcohol dehydroxylase 2, alcohol dehydroxylase 3, alcohol dehydroxylase 4, alcohol dehydroxylase 5, alcohol dehydroxylase 6, alcohol dehydroxylase 7, aldehyde oxidase 2, aldehyde oxidase 3, aldehyde oxidase 4, aldehyde oxidase 5, and aldehyde oxidase 6;
   (b) in the batch reactor, subjecting the engineered non-plant cells to fermentation by incubating the engineered non-plant cells for a time period of at least 5 minutes to produce a solution comprising the benzylisoquinoline alkaloid product and cellular material; and
   (c) using at least one separation unit to separate the benzylisoquinoline alkaloid product from the cellular material to provide the product stream comprising the benzylisoquinoline alkaloid product, wherein the separation unit comprises a component selected from the group consisting of: a chromatography component, a precipitation component, a filtration component, an extraction component, and a sedimentation component.

2. The method of claim 1, wherein the engineered non-plant cells are engineered fungal cells.

3. The method of claim 2, wherein the engineered fungal cell comprises one or more feedback inhibition alleviating mutations in one or more biosynthetic enzyme genes that encode 3-deoxy-d-arabinose-heptulosonate-7-phosphate synthase.

4. The method of claim 2, wherein the engineered fungal cell comprises one or more feedback inhibition alleviating mutations in one or more biosynthetic enzyme genes that encode chorismate mutase.

5. The method of claim 2, wherein the engineered fungal cell further comprises at least one transcriptional modulation modification in a biosynthetic enzyme gene.

6. The method of claim 1, wherein at least one process parameter of the batch reactor is modifiable to alter a resultant benzylisoquinoline alkaloid product composition, wherein the at least one process parameter that is modifiable comprises at least one of dissolved oxygen, pH, stirring speed, aeration rate, and cell density.

7. The method of claim 1, wherein the benzylisoquinoline alkaloid product is selected from the group of norcoclaurine, norlaudanosoline, tyramine, 4-hydroxyphenylacetaldehyde, 4-hydroxyphenylpyruvic acid, L-3, 4-dihydroxyphenylalanine, 3,4-dihydroxyphenylacetaldehyde, and dopamine.

8. The method of claim 1, wherein the benzylisoquinoline alkaloid product is a benzylisoquinoline alkaloid that has a structural class that is selected from the group of benzylisoquinolines, protoberberines, protopines, benzophenanthridines, promorphinans, morphinans, secoberbines, phthalideisoquinolines, aporphines, and bisbenzylisoquinolines.

9. The method of claim 1, wherein the product stream does not contain more than 5 ppm of a molecule selected from the group of lignin, pigments, flavonoids, phenanthreoids, latex, rubisco, meconic acid, pseudomorphine, narceine, thebaol, and pollen.

10. The method of claim 1, wherein the product stream does not contain a detectable amount of a substance selected from the group consisting of pesticides, fungicides, or herbicides.

11. The method of claim 2, wherein the engineered fungal cell comprises two or more heterologous coding sequences, wherein the two or more heterologous coding sequences encode at least a first enzyme and a second enzyme that are involved in a metabolic pathway that converts the tyrosine into the benzylisoquinoline alkaloid product, wherein the first enzyme and second enzyme are operably connected along the metabolic pathway.

12. The method of claim 2, wherein the engineered fungal cell comprises three heterologous coding sequences, wherein the three heterologous coding sequences encode a first enzyme, second enzyme, and third enzyme that are involved in a metabolic pathway that converts the tyrosine into the benzylisoquinoline alkaloid product, wherein the first enzyme, second enzyme, and third enzyme are operably connected along the metabolic pathway.

\* \* \* \* \*